US005874299A

United States Patent [19]
Lonberg et al.

[11] Patent Number: 5,874,299
[45] Date of Patent: *Feb. 23, 1999

[54] TRANSGENIC NON-HUMAN ANIMALS CAPABLE OF PRODUCING HETEROLOGOUS ANTIBODIES

[75] Inventors: Nils Lonberg; Robert M. Kay, both of San Francisco, Calif.

[73] Assignee: GenPharm International, Inc., San Jose, Calif.

[ * ] Notice: The term of this patent shall not extend beyond the expiration date of Pat. Nos. 5,545,806, 5,569,825, 5,633,425 and 5,625,126.

[21] Appl. No.: 800,353

[22] Filed: Feb. 14, 1997

Related U.S. Application Data

[63] Continuation of Ser. No. 834,539, Feb. 5, 1992, Pat. No. 5,633,425, which is a continuation-in-part of Ser. No. 575,962, Aug. 31, 1990, abandoned, and Ser. No. 574,748, filed as PCT/US91/06185 Aug. 29, 1991, abandoned.

[51] Int. Cl.$^6$ .......................... C12N 15/00; C12N 15/79; C12N 15/11
[52] U.S. Cl. .................................. 435/320.1; 435/172.3; 935/34; 536/23.53
[58] Field of Search .............................. 800/2; 435/320.1, 435/7.1, 69.1, 172.3; 935/34, 56, 71; 536/23.1, 23.53

[56] References Cited

U.S. PATENT DOCUMENTS 5,545,807  8/1996  Surani ......................... 800/2

FOREIGN PATENT DOCUMENTS

| 0 315 062 | 5/1989 | European Pat. Off. . |
|---|---|---|
| 90 04026 | 4/1990 | WIPO . |
| 90 12878 | 11/1990 | WIPO . |
| 91 00906 | 1/1991 | WIPO . |
| 91 10741 | 7/1991 | WIPO . |
| 92 03918 | 3/1992 | WIPO . |

OTHER PUBLICATIONS

Alt et al., TIG—Aug. 1985.
Berman et al., EMBO J. 7:727 (1988).
Berton et. al., Proc. Natl. Acad. Sci. USA 86:2829 (1989).
Bollag et al., Annu. Rev. Genet. 23:199 (1989).
Bruggemann et al., Eur. J. Immunol. 21:1323 (1991).
Bruggemann et al., Proc. Natl. Acad. Sci. USA 86:6709 (1989).
Bucchini et al., Nature 326:409 (1987).
Buttin, TIG 3(8) (1987).
Capecchi, TIG 5:70 (1989).
Capecchi, Science 244:1288 (1989).
Coffman et. al., J. Immunol. 136:949 (1986).
Coffman et al., J. Immunol. 139:3685 (1987).
Doetschman et al., Nature 330:576 (1987).
Durdik et al., Proc. Natl. Acad. Sci. USA 86:2346 (1989).
Esser and Radbruch, EMBO J. 8:483 (1989).
Ferrier et al., EMBO J. 9:117 (1990).
Forni, Eur. J. Immunol. 20:983 (1990).
Gerstein et al., Cell 63:537 (1990).
Goodhardt et al., Proc. Natl. Acad. Sci. USA 84:4229 (1987).
Gordon, The Mount Sinai Journal of Medicine 53:223 (1986).
Hagman et al., J. Exp. Med. 169:1911 (1989).
Hofker et al., Proc. Natl. Acad. Sci. USA 86:5567 (1989).
Humphries et al., Nature 331:446 (1988).
Ichihard et al., EMBO J. 7:4141 (1988).
Iglesias et al., Nature 330:482 (1987).
Jaenisch, Science 240:1468 (1988).
James and Bell, J. of Immunol. Methods 100:5 (1987).
Jasin and Berg, Genes & Development 2:1353 (1988).
Kenny et al., J. of Immunol. 142:4466 (1989).
Kitamura et al., Nature 350:423 (1991).
Koller et al., Proc. Natl. Acad. Sci. USA 86:8932 (1989).
Lin et al., Proc. Natl. Acad. Sci. USA 82:1391 (1985).
Linton et al., Cell 59:1049 (1989).
Lo et al., Eur. J. Immunol. 21:1001 (1991).
Lorenz et al., Nucl. Acids Res. 15:9667 (1987).
Lutzker and Alt, Mol. Cell Biol. 8:1849 (1988).
Mansour et al., Nature 336:348 (1988).
Miller et al., Nature 295:428 (1982).
Mills et.al., Nucl. Acids. Res. 18:7305 (1991).
Mills et al., Nature 306:809 (1983).
Mowatt et. al., J.Immunol. 136:2674 (1986).
Muller et al., Eur. J. Immunol. 19:923 (1989).
Murray & Szostak, Nature 305:189 (1983).
Neuberger et al., Nature 338:350 (1989).
Nikaido et al., J. Biol. Chem. 257:7322 (1982).
Nikaido et al., Nature 292:845 (1981).

(List continued on next page.)

*Primary Examiner*—Jasemine C. Chambers
*Assistant Examiner*—Karen M. Hauda
*Attorney, Agent, or Firm*—Townsend & Townsend & Crew

[57] ABSTRACT

The invention relates to transgenic non-human animals capable of producing heterologous antibodies, i.e., antibodies encoded by immunoglobulin heavy and light chain genes not normally found in the genome of that species of non-human animal. In one aspect of the invention, transgenes encoding unrearranged heterologous human immunoglobulin heavy and light chains are introduced into a non-human animal thereby forming a transgenic animal capable of producing antibodies encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous antibody. The invention also relates to heavy and light chain immunoglobulin transgenes for making such transgenic non-human animals as well as methods and vectors for disrupting endogenous immunoglobulin loci in the transgenic animal. The invention also includes methods to generate a synthetic immunoglobulin variable region gene segment repertoire used in transgene construction and methods to induce heterologous antibody production using animals containing heterologous rearranged or unrearranged heavy and light chain immunoglobulin transgenes.

7 Claims, 36 Drawing Sheets

OTHER PUBLICATIONS

Nussenzweig et al., J. Exp. Med. 167:1969 (1988).
Oettinger et al., Science 248:1517 (1990).
Petters, Vet. Immunol. Immunopath. 17:267 (1987).
Pettersson et al., Nature 344:165 (1990).
Rabbits et. al., Nucl. Acids Res. 9:4509 (1981).
Rath et al., J. of Immunol. 146:2841 (1991).
Rath et al., J. of Immunol. 143:2074 (1989).
Ravetch et al., Proc. Natl. Acad. Sci. USA 77:6734 (1980).
Reid et al., Proc. Natl. Acad. Sci. USA 86:840 (1989).
Ritchie et al., Nature 312:517 (1984).
Rothman et al., Intl. Immunol. 2:621 (1990).
Rusconi et al., Nature 314:330 (1985).
Sato et al., Biochem. Biophys. Res. Comm. 154:264 (1988).
Scanos and Bieberich, Advances in Genetics 24:285 (1987).
Sevidy and Sharp, Proc. Natl. Acad. Sci. USA 86:227 (1989).
Shimizu et al., Proc. Natl. Acad. Sci. USA 86:8020 (1989).
Shimizu et al., J. Exp. Med. 173:1385 (1991).
Sideras et. al., Intl. Immunol. 1:631 (1989).
Siebenlist et al., Nature 294:631 (1981).
Smithies et al., Nature 317:230 (1985).
Snapper et. al., Science 236:944 (1987).
Song et al., Proc. Natl. Acad. Sci. USA 84:6820 (1987).
Soriano et al., Cell 64:693 (1991).
Stavnezer et al., Proc. Natl. Acad Sci. USA 85:7704 (1988).
Stites et al., in Basic and Clinical Immunology, p. 50 (1984).
Storb, In Immunoglobulin Genes, pp. 303–326 (Academic Press, Limited), 1989.
Storb et al., Immunological Reviews 89:85 (1986).
Szurek et al., J. Immunol. 135:620 (1985).
Tahara et al., Immunogenetics 32:351 (1990).
Tanaka et al., J. Exp. Med. 175:597 (1992).
Taussig et al., Immunology Today 10:143 (1989).
Thomas and Capecchi, Cell 51:503 (1987).
Thomas et al., Cell 44:419 (1986).
Uhlmann and Peyman, Chemical Reviews 90:544 (1990).
Vlasov et al., Chemical Abstracts, p. 28, 112:229433X (1990).
Weaver et al., Cell 42:117 (1985).
Yamamura et al., Proc. Natl. Acad. Sci. USA 83:2152 (1986).
Yancopoulos and Alt, Ann. Rev. Immunol. 4:339 (1986).
Yancopoulos and Alt, Cell 40:271 (1985).
Yasui et al., Eur. J. Immunol. 19:1399 (1989).
Zijustra et al., Nature 342:435 (1989).
Zimmer and Gruss, Nature 338:150 (1989).

SYNTHETIC HEAVY CHAIN VARIABLE REGION

TRANSGENIC NON-HUMAN ANIMALS CAPABLE OF PRODUCING HETEROLOGOUS ANTIBODIES

This application is a continuation of U.S. patent application Ser. No. 07/834,539, filed Feb. 5, 1992, U.S. Pat. No. 5,633,425 which is a continuation-in-part of U.S. patent application Ser. No. 07/575,962, filed Aug. 31, 1990, now abandoned, and U.S. patent application Ser. No. 07/574,748, filed Aug. 29, 1990, now abandoned, all of which are incorporated herein by reference. This application also claims benefit from PCT/US91/06185, filed Aug. 28, 1991.

TECHNICAL FIELD

The invention relates to transgenic non-human animals capable of producing heterologous antibodies, transgenes used to produce such transgenic animals, immortalized B-cells capable of producing heterologous antibodies, methods and vectors for disrupting endogenous immunoglobin loci, methods to generate a synthetic immunoglobulin variable region gene segment repertoire, and methods to induce heterologous antibody production.

BACKGROUND OF THE INVENTION

One of the major impediments facing the development of in vivo applications for monoclonal antibodies in humans is the intrinsic immunogenicity of non-human immunoglobulins. Patients respond to therapeutic doses of rodent monoclonal antibodies by making antibodies against the rodent immunoglobulin sequences. These human anti-mouse antibodies (HAMA) neutralize the therapeutic antibodies and can cause acute toxicity. The HAMA response is less dramatic in immunodeficient patients. Therefore, intrinsic immunogenicity has not prevented the use of rodent monoclonal antibodies for the treatment of graft rejection, which involves the temporary attenuation of the patient's immune response. Rodent antibodies may also be useful for treating certain lymphomas that involve immunodeficiencies. However, even immunodeficient patients can mount a HAMA response which leads to a reduction in safety and efficacy.

The present technology for generating monoclonal antibodies involves pre-exposing, or priming, an animal (usually a rat or mouse) with antigen. This pre-exposure leads to the formation of splenic B-cells that secrete immunoglobulin molecules with high affinity for the antigen. Spleen cells from a primed animal are then fused with myeloma cells to form immortal, antibody secreting, hybridoma cells. Individual hybridoma clones are screened to identify those cells producing immunoglobulins directed against a particular antigen.

The genetic engineering of individual antibody genes has been proposed. Two genetic engineering approaches have been reported: chimeric antibodies and complementarity-determining-region (CDR) grafting. The simplest approach, chimeric antibodies, takes advantage of the fact that the variable and constant portions of an antibody molecule are encoded on separate exons. By simply fusing the variable region exons of a rearranged mouse antibody gene with a human constant region exons, a hybrid antibody gene can be obtained (Morrison, S. L., et al. (1984), Proc. Natl. Acad. Sci. USA, 81, 6851–6855). The major problem with this approach is that while the highly immunogenic mouse Fc region is eliminated, the remaining mouse Fab sequences are still immunogenic (Bruggemann, et al. (1989), J. Exp. Med., 170, 2153–2157). The CDR grafting approach uses computer modeling to generate a completely artificial antibody in which the only mouse sequences are those involved in antigen binding (Riechmann, L., et al. (1988), Nature, 332, 323–327). Each of these approaches requires the prior characterization of a rodent monoclonal antibody directed against the antigen of interest, and both require the generation of a stable transfected cell line that produces high levels of the engineered antibody.

Another approach to the production of human antibodies is a proposal involving the construction of bacterial expression libraries containing immunoglobulin cDNA sequences (Orlandi, et al. (1989), Proc. Natl. Acad. Sci. USA, 86, 3833–3837, and Huse, et al. (1989), Science, 246, 1275–1281). This technique reportedly has only been used to generate antibody fragments derived from mouse cDNA sequences.

A number of experiments have reported the use of transfected cell lines to determine the specific DNA sequences required for Ig gene rearrangement (reviewed by Lewis and Gellert (1989), Cell, 59, 585–588). Such reports have identified putative sequences and concluded that the accessibility of these sequences to the recombinase enzymes used for rearrangement is modulated by transcription (Yancopoulos and Alt (1985), Cell, 40, 271–281). The sequences for V(D)J joining are reportedly a highly conserved, near-palindromic heptamer and a less well conserved AT-rich nanomer separated by a spacer of either 12 or 23 bp (Tonegawa (1983), Nature, 302, 575–581; Hesse, et al. (1989), Genes in Dev., 3, 1053–1061). Efficient recombination reportedly occurs only between sites containing recombination signal sequences with different length spacer regions.

The production of transgenic mice containing various forms of immunoglobulin genes has also been reported. Rearranged mouse immunoglobulin heavy or light chain genes have been used to produce transgenic mice. Such transgenes reportedly are capable of excluding the rearrangement of endogenous Ig genes. See e.g. Weaver et al. (1985), Cell, 42, 117–127; Iglesias, et al. (1987), Nature, 330, 482–484; Storb et al. (1985), Banbury Reports, 20, 197–207; Neuberger et al. (1989), Nature, 338, 350–352; Hagman et al. (1989), J. Exp. Med., 169, 1911–1929; and Storb (1989) in Immunoglobulin Genes, Academic Press, T. Honjo, F. W. Alt and T. H. Rabbitts eds. pp. 303–326. In addition, functionally rearranged human Ig genes including the $\mu$ or $\gamma 1$ constant region have been expressed in transgenic mice. Yamamura, et al. (1986), Proc. Natl. Acad. Sci. USA, 83, 2152–2156; Nussenzweig, et al. (1987), Science, 236, 816–819. In the case of the $\mu$ rearranged heavy chain gene, allelic exclusion of endogenous immunoglobulin gene loci was reported.

Allelic exclusion, however, does not always occur in all transgenic B-cells. See e.g. Rath, et al. (1989), J. Immunol., 143, 2074–2080 (rearranged $\mu$ gene construct); Manz, et al. (1988), J. Exp. Med., 168, 1363–1381 ($\mu$ transgenes lacking transmembrane exons did not prevent rearrangement of the endogenous genes); Ritchie, et al. (1984), Nature, 312, 517–520 and Storb, et al. (1986), Immunol. Rev., 89, 85–102 (transgenic mice expressing rearranged n transgene capable of forming stable heavy/light chain complex only rearrange endogenous κ genes in B-cells that fail to correctly rearrange endogenous heavy chain gene); and Manz, et al. (1988), J. Exp. Med., 168, 1363–1381 (transgenic mice containing κ gene encoding light chain incapable of combining with heavy chains, show only a low level of allelic exclusion). See also Nussenzweig, et al. (1988), Nature, 336, 446–450); Durdik, et al. (1989), Proc. Natl. Acad. Sci. USA, 86, 2346–2350; and Shimizu, et al. (1989), Proc. Natl. Acad. Sci. USA, 86, 8020–8023.

Somatic mutation has also been reported in a 15 kb mouse κ gene construct in hyperimmunized transgenic mice (O'Brien, et al. (1987), *Nature*, 326, 405–409; Storb (1989) in Immunoglobulin Genes, Academic Press, T. Honjo, F. W. Alt, and T. H. Rabbitts, eds. pp. 303–326) and in the variable portion of a μ heavy chain transgene (Durdik, et al. (1989), *Proc. Natl. Acad. Sci. USA*, 86, 2346–2350).

Ig gene rearrangement, though studied in tissue culture cells, has not been extensively examined in transgenic mice. Only a handful of reports have been published describing rearrangement test constructs introduced into mice [Buchini, et al. (1987), *Nature*, 326, 409–411 (unrearranged chicken λ transgene); Goodhart, et al. (1987), *Proc. Natl. Acad. Sci. USA*, 84, 4229–4233) (unrearranged rabbit κ gene); and Bruggemann, et al. (1989), *Proc. Natl. Acad. Sci. USA*, 86, 6709–6713 (hybrid mouse-human heavy chain)]. The results of such experiments, however, have been variable, in some cases, producing incomplete or minimal rearrangement of the transgene.

Based on the foregoing, it is clear that a need exists for heterologous monoclonal antibodies, e.g. antibodies of human origin, derived from a species other than human. Thus, it is an object of the invention herein to provide a source of monoclonal antibodies that may be used therapeutically in the particular species for which they are designed.

In accordance with the foregoing object transgenic non-human animals are provided which are capable of producing a heterologous antibody, such as a human antibody.

Further, it is an object to provide B-cells from such transgenic animals which are capable of expressing heterologous antibodies wherein such B-cells are immortalized to provide a source of a monoclonal antibody specific for a particular antigen.

In accordance with this foregoing object, it is a further object of the invention to provide hybridoma cells that are capable of producing such heterologous monoclonal antibodies.

Still further, it is an object herein to provide heterologous unrearranged and rearranged immunoglobulin heavy and light chain transgenes useful for producing the aforementioned non-human transgenic animals.

Still further, it is an object herein to provide methods to disrupt endogenous immunoglobulin loci in the transgenic animals.

Still further, it is an object herein to provide methods to induce heterologous antibody production in the aforementioned transgenic non-human animal.

A further object of the invention is to provide methods to generate an immunoglobulin variable region gene segment repertoire that is used to construct one or more transgenes of the invention.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

In accordance with the foregoing objects, in one aspect of the invention, transgenic non-human animals are provided that contain rearranged, unrearranged or a combination of rearranged and unrearranged heterologous immunoglobulin heavy and light chain transgenes in the germline of the transgenic animal. For each of the foregoing animals, functionally rearranged heterologous heavy and light chain immunoglobulin transgenes are found in the B-cells of the transgenic animal.

Heterologous heavy and/or light unrearranged immunoglobulin transgenes are introduced into a host non-human animal to produce a transgenic non-human animal containing a heavy and a light heterologous immunoglobulin gene or an intermediate animal containing one or the other transgene. When incorporated into the germline of such intermediate animals, crosses between one containing a heavy chain transgene and one containing a light chain transgene produces a transgenic non-human animal containing both heavy and light heterologous immunoglobulin transgenes.

The transgenes of the invention include a heavy chain transgene comprising DNA encoding at least one variable gene segment, one diversity gene segment, one joining gene segment and one constant region gene segment. The immunoglobulin light chain transgene comprises DNA encoding at least one variable gene segment, one joining gene segment and one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes permit recombination of the gene segments (functional rearrangement) and somatic mutation of the resultant rearranged immunoglobulin heavy and/or light chains within the transgenic non-human animal when exposed to antigen.

In one aspect of the invention, heterologous heavy and light immunoglobulin transgenes comprise relatively large fragments of unrearranged heterologous DNA. Such fragments typically comprise a substantial portion of the C, J (and in the case of heavy chain, D) segments from a heterologous immunoglobulin locus. In addition, such fragments also comprise a substantial portion of the variable gene segments.

In an alternate embodiment, HP LaserJet Series IIH-PLASEII.PRSegments. In such transgene constructs, the various regulatory sequences, e.g. promoters, enhancers, class switch regions, recombination signals and the like, comprise corresponding sequences derived from the heterologous DNA. Alternatively, such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse.

In a method of the invention, a transgenic non-human animal containing germline unrearranged light and heavy immunoglobulin transgenes—that undergo VDJ joining during D-cell differentiation—is contacted with an antigen to induce production of a heterologous antibody in a secondary repertoire B-cell. Such induction causes somatic mutation in the rearranged heavy and/or light chain transgenes contained in primary repertoire B-cells to produce a heterologous antibody having high affinity and specificity for the antigen.

Such antibody producing B-cells may be immortalized by transforming with a virus, or with an oncogene containing DNA construct, or alternatively, immortalized by fusing with a myeloma cell line to form antibody secreting hybridomas. In each instance, clones having sufficient affinity and specificity for a particular antigen are selected to provide a source of monoclonal antibody having low immunogenicity in the species from which the immunoglobulin gene segments of the transgenes are derived.

Also included in the invention are vectors and methods to disrupt the endogenous immunoglobulin loci in the non-human animal to be used in the invention. Such vectors and methods utilize a transgene, preferably positive-negative selection vector, which is constructed such that it targets the functional disruption of a class of gene segments encoding a heavy and/or light immunoglobulin chain endogenous to the non-human animal used in the invention. Such endogenous gene segments include diversity, joining and constant region gene segments. In this aspect of the invention, the positive-negative selection vector is contacted with at least one embryonic stem cell of a non-human animal after which cells are selected wherein the positive-negative selection vector has integrated into the genome of the non-human animal by way of homologous recombination. After transplantation, the resultant transgenic non-human animal is substantially incapable of mounting an immunoglobulin-mediated immune response as a result of homologous integration of the vector. Such immune deficient non-human animals may thereafter be used for study of immune deficiencies or used as the recipient of heterologous immunoglobulin heavy and light chain transgenes.

The invention also includes methods for generating a synthetic variable region gene segment repertoire to be used in the transgenes of the invention. The method comprises generating a population of immunoglobulin V segment DNAs wherein each of the V segment DNAs encodes an immunoglobulin V segment and contains at each end a cleavage recognition site of a restriction endonuclease. The population of immunoglobulin V segment DNAs is thereafter concatenated to form the synthetic immunoglobulin V segment repertoire.

Another aspect of the invention includes transgenic non-human animals that contain functionally rearranged heterologous heavy and light chain immunoglobulin transgenes in the germline of the transgenic animal. Such animals contain primary repertoire B-cells that express such rearranged heavy and light transgenes. Such B-cells are capable of undergoing somatic mutation when contacted with an antigen to form a heterologous antibody having high affinity and specificity for the antigen.

The invention also includes transgenic animals containing germ line cells having a heavy and light transgene wherein one of the said transgenes contains rearranged gene segments with the other containing unrearranged gene segments. In the preferred embodiments, the rearranged transgene is a light chain immunoglobulin transgene and the unrearranged transgene is a heavy chain immunoglobulin transgene.

The invention also includes methods for producing heterologous antibodies in a transgenic animal containing primary repertoire B-cells having rearranged heavy and light heterologous immunoglobulin transgenes. Such transgenic animals may be obtained from any of the aforementioned transgenic animals. Thus, the transgenic animal containing unrearranged heavy and light transgenes, the transgenic animal containing rearranged heavy and light transgenes or the animal containing one rearranged and one unrearranged transgene in the germline of the animal, each contain primary repertoire B-cells having rearranged, heterologous heavy and light immunoglobulin transgenes. In the method of the invention, a desired first heterologous antibody is produced which is capable of binding a first antigen. The rearranged immunoglobulin heavy and light transgenes in the primary repertoire B-cells of such animals are known to produce primary repertoire antibodies having sufficient affinity for a second known antigen. In this method, the transgenic non-human animal is contacted, sequentially or simultaneously, with the first and second antigen to induce production of the first heterologous antibody by somatic mutation of the rearranged transgenes. The secondary repertoire B-cells so produced are then manipulated as previously described to immortalize the production of the desired monoclonal antibody capable of binding the first antigen.

The present invention also includes plasmids, useful in cloning large DNA fragments (e.g., immunoglobulin genomic fragments), that have an origin of replication (ORI), a copy control region (e.g., ROP, or the copy control region of pACYC177, or others known to those skilled in the art), and a cloning site. The plasmids also include a transcription terminator (e.g., trpR or others known to those skilled in the art) downstream of endogenous plasmid-derived promoters such as that of the ampicillin resistance gene ($amp^R$). The transcription termination is located upstream of the cloning site so that transcripts originating at the promoter are terminated upstream of the cloning site. In a preferred embodiment, the cloning site is flanked by rare restriction sites, which are sites consisting of seven, eight, or more nucleotides, instead of the six or fewer nucleotides that make up more common restriction sites; e.g., Not I, Sfi I, and Pac I. Rare restriction sites also include sites that contain nucleotide sequences occurring rarely in natural DNA sequences; i.e., less frequently than about once in every 8,000–10,000 nucleotides.

BRIEF DESCRIPTION OF THE FIGURES

FIGS. 26a through f depict the structure of a mouse heavy chain targeting vector.

Figure 1:
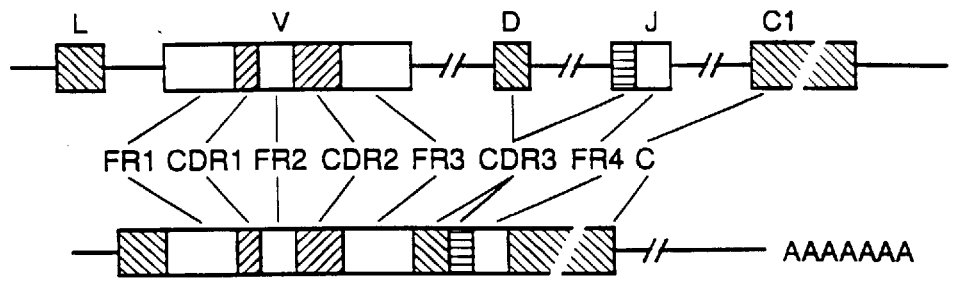
FIG. 1 depicts the complementarity determining regions CDR1, CDR2 and CDR3 and framework regions FR1, FR2, FR3 and FR4 in unrearranged genomic DNA and mRNA expressed from a rearranged immunoglobulin heavy chain gene.

Table 1 depicts the sequence of vector pGPe.

Table 2 depicts the sequence of gene $V_H 49.8$.

DETAILED DESCRIPTION

The design of a transgenic non-human animal that responds to foreign antigen stimulation with a heterologous antibody repertoire, requires that the heterologous immunoglobulin transgenes contained within the transgenic animal function correctly throughout the pathway of B-cell development. Accordingly, the transgenes in one aspect of the invention are constructed so as to produce one or all of the following: (1) high level and cell-type specific expression, (2) functional gene rearrangement, (3) activation of and response to allelic exclusion, (4) expression of a sufficient primary repertoire, (5) signal transduction, (6) class switching, (7) somatic hypermutation, and (8) domination of the transgene antibody locus during the immune response.

As will be apparent from the following disclosure, not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, New York.

The Structure and Generation of Antibodies

Immunoglobulins, also known as antibodies, are a group of glycoproteins present in the serum and tissue fluids of all mammals. They are produced in large amounts by plasma cells (also referred to herein as "secondary repertoire B-cells") which develop from precursor B lymphocytes (referred to herein as "primary repertoire B-cells"). Such primary repertoire B-cells carry membrane-bound immunoglobulin which is similar to that produced by the fully differentiated secondary repertoire B-cell. Contact between primary repertoire B-cells and foreign antigen is required for the induction of antibody formation.

The basic structure of all immunoglobulins is based upon a unit consisting of two identical light polypeptide chains and two identical heavy polypeptide chains linked together by disulfide bonds. Each light chain comprises two regions known as the variable light chain region and the constant light chain region. Similarly, the immunoglobulin heavy chain comprises two regions designated the variable heavy chain region and the constant heavy chain region. The constant region for the heavy or light chain is encoded by genomic sequences referred to as heavy or light constant region gene segments. The use of a particular heavy chain gene segment defines the class of immunoglobulin. For example, in humans, the $\mu$ constant region gene segments define the IgM class of antibody whereas the use of a γ, γ2, γ3 or γ4 constant region gene segment defines the IgG class of antibodies as well as the IgG subclasses IgG1 through IgG4.

The variable regions of the heavy and light immunoglobulin chains together contain the antigen binding domain of the antibody. Because of the need for diversity in this region of the antibody to permit binding to a wide range of antigens, the DNA encoding the initial or primary repertoire variable region comprises a number of different DNA segments derived from families of specific variable region gene segments. In the case of the light chain variable region, such families comprise variable (V) gene segments and joining (J) gene segments. Thus, the initial variable region of the light chain is encoded by one V gene segment and one J gene segment each selected from the family of V and J gene segments contained in the genomic DNA of the organism. In the case of the heavy chain variable region, the DNA encoding the initial or primary repertoire variable region of the heavy chain comprises one heavy chain V gene segment, one heavy chain diversity (D) gene segment and one J gene segment, each selected from the appropriate V, D and J families of immunoglobulin gene segments in genomic DNA.

The Primary Repertoire

The process for generating DNA encoding the heavy and light chain immunoglobulin genes occurs primarily in developing B-cells. Prior to the joining of various immunoglobulin gene segments, the V, D, J and constant (C) gene segments are found, for the most part, in clusters of V, D, J and C gene segments in the precursors of primary repertoire B-cells. Generally, all of the gene segments for a heavy or light chain are located in relatively close proximity on a single chromosome. Such genomic DNA prior to recombination of the various immunoglobulin gene segments is referred to herein as "unrearranged" genomic DNA. During B-cell differentiation, one of each of the appropriate family members of the V, D, J (or only V and J in the case of light chain genes) gene segments are recombined to form functionally rearranged heavy and light immunoglobulin genes. Such functional rearrangement is of the variable region segments to form DNA encoding a functional variable region. This gene segment rearrangement process appears to be sequential. First, heavy chain D-to-J joints are made, followed by heavy chain V-to-DJ joints and light chain V-to-J joints. The DNA encoding this initial form of a functional variable region in a light and/or heavy chain is referred to as "functionally rearranged DNA" or "rearranged DNA". In the case of the heavy chain, such DNA is referred to as "rearranged heavy chain DNA" and in the case of the light chain, such DNA is referred to as "rearranged light chain DNA". Similar language is used to describe the functional rearrangement of the transgenes of the invention.

The recombination of variable region gene segments to form functional heavy and light chain variable regions is mediated by recombination signal sequences (RSS's) that flank recombinationally competent V, D and J segments. RSS's necessary and sufficient to direct recombination, comprise a dyad-symmetric heptamer, an AT-rich nonamer and an intervening spacer region of either 12 or 23 base pairs. These signals are conserved among the different loci and species that carry out D-J (or V-J) recombination and are functionally interchangeable. See Oettinger, et al. (1990), Science, 248, 1517–1523 and references cited therein. The heptamer comprises the sequence CACAGTG or its analogue followed by a spacer of unconserved sequence and then a nonamer having the sequence ACAAAAACC or its analogue. These sequences are found on the J, or downstream side, of each V and D gene segment. Immediately preceding the germline D and J segments are again two recombination signal sequences, first the nonamer and then the heptamer again separated by an unconserved sequence. The heptameric and nonameric sequences following a $V_L$, $V_H$ or D segment are complementary to those preceding the $J_L$, D or $J_H$ segments with which they recombine. The spacers between the heptameric and nonameric sequences are either 12 base pairs long or between 22 and 24 base pairs long.

In addition to the rearrangement of V, D and J segments, further diversity is generated in the primary repertoire of immunoglobulin heavy and light chain by way of variable recombination between the V and J segments in the light chain and between the D and J segments of the heavy chain. Such variable recombination is generated by variation in the exact place at which such segments are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity.

After VJ and/or VDJ rearrangement, transcription of the rearranged variable region and one or more constant region gene segments located downstream from the rearranged variable region produces a primary RNA transcript which upon appropriate RNA splicing results in an mRNA which encodes a full length heavy or light immunoglobulin chain. Such heavy and light chains include a leader signal sequence to effect secretion through and/or insertion of the immunoglobulin into the transmembrane region of the B-cell. The DNA encoding this signal sequence is contained within the first exon of the V segment used to form the variable region of the heavy or light immunoglobulin chain. Appropriate regulatory sequences are also present in the mRNA to control translation of the mRNA to produce the encoded heavy and light immunoglobulin polypeptides which upon proper association with each other form an antibody molecule.

The net effect of such rearrangements in the variable region gene segments and the variable recombination which may occur during such joining, is the production of a primary antibody repertoire. Generally, each B-cell which has differentiated to this stage, produces a single primary repertoire antibody. During this differentiation process, cellular events occur which suppress the functional rearrangement of gene segments other than those contained within the functionally rearranged Ig gene. The process by which diploid B-cells maintain such mono-specificity is termed allelic exclusion.

The Secondary Repertoire

B-cell clones expressing immunoglobulins from within the set of sequences comprising the primary repertoire are immediately available to respond to foreign antigens. Because of the limited diversity generated by simple VJ and VDJ joining, the antibodies produced by the so-called primary response are of relatively low affinity. Two different types of B-cells make up this initial response: precursors of primary antibody-forming cells and precursors of secondary repertoire B-cells (Linton, et al. (1989), Cell, 59, 1049–1059). The first type of B-cell matures into IgM-secreting plasma cells in response to certain antigens. The other B-cells respond to initial exposure to antigen by entering a T-cell dependent maturation pathway. It is during this T-cell dependent maturation of B-cells that a second level of diversity is generated by a process termed somatic mutation (sometimes also referred to as hypermutation). These primary repertoire B-cells use the immunoglobulin molecules on their surfaces to bind and internalize the foreign antigen. If the foreign antigen is a protein or is physically linked to another protein antigen, that protein antigen is then processed and presented on the cell surface by a major histocompatibility complex (MHC) molecule to a helper T-cell which in turn induces maturation of the B-cell. Lanzavecchia (1985), Nature, 314, 537. This overall maturation of the B-cell is known as the secondary response.

During the T-cell dependent maturation of antigen stimulated B-cell clones, the structure of the antibody molecule on the cell surface changes in two ways: the constant region switches to a non-IgM subtype and the sequence of the variable region is modified by multiple single amino acid substitutions to produce a higher affinity antibody molecule. It is this process of somatic mutation, followed by the selection of higher affinity clones, that generates highly specific and tightly binding immunoglobulins characterized by the Ig mediated immune response.

As previously indicated, each variable region of a heavy or light Ig chain contains an antigen binding domain. It has been determined by amino acid and nucleic acid sequencing that somatic mutation during the secondary response occurs throughout the V region including the three complementary determining regions (CDR1, CDR2 and CDR3) also referred to as hypervariable regions 1, 2 and 3. The CDR1 and CDR2 are located within the variable gene segment whereas the CDR3 is largely the result of recombination between V and J gene segments or V, D and J gene segments. Those portions of the variable region which do not consist of CDR1, 2 or 3 are commonly referred to as framework regions designated FR1, FR2, FR3 and FR4. See FIG. 1. During hypermutation, the rearranged DNA is mutated to give rise to new clones with altered Ig molecules. Those clones with higher affinities for the foreign antigen are selectively expanded by helper T-cells, giving rise to affinity maturation of the expressed antibody. Clonal selection typically results in expression of clones containing new mutation within the CDR1, 2 and/or 3 regions. However, mutations outside these regions also occur which influence the specificity and affinity of the antigen binding domain.

Transgenic Non-Human Animals Capable of Producing Heterologous Antibody

Transgenic non-human animals in one aspect of the invention are produced by introducing at least one of the immunoglobulin transgenes of the invention (discussed hereinafter) into a zygote or early embryo of a non-human animal. The non-human animals which are used in the invention generally comprise any mammal which is capable of rearranging immunoglobulin gene segments to produce a primary antibody response and, which, in addition, are capable of mounting a secondary response by way of somatic mutation of such rearranged Ig genes. A particularly preferred non-human animal is the mouse or other members of the rodent family. Mice are particularly useful since their immune system has been extensively studied, including the genomic organization of the mouse heavy and light immunoglobulin loci. See e.g. Immunoglobulin Genes, Academic Press, T. Honjo, F. W. Alt and T. H. Rabbitts, eds. (1989).

However, the invention is not limited to the use of mice. Rather, any non-human mammal which is capable of mounting a primary and secondary antibody response may be used. Such animals include non-human primates, such as chimpanzee, bovine, ovine and porcine species, other members of the rodent family, e.g. rat, as well as rabbit and guinea pig. Particular preferred animals are mouse, rat, rabbit and guinea pig, most preferably mouse.

As used herein, the term "antibody" refers to a glycoprotein comprising at least two identical light polypeptide chains and two identical heavy polypeptide chains linked together by disulfide bonds. Each of the heavy and light polypeptide chains contains a variable region (generally the amino terminal portion of the polypeptide chain) which contains a binding domain which interacts with antigen. Each of the heavy and light polypeptide chains also comprises a constant region of the polypeptide chains (generally the carboxyl terminal portion) some of which sequences mediate the binding of the immunoglobulin to host tissues including various cells of the immune system, some phagocytic cells and the first component (C1q) of the classical complement system.

As used herein, a "heterologous antibody" is defined in relation to the transgenic non-human organism producing such an antibody. It is defined as an antibody having an amino acid sequence or an encoding DNA sequence corresponding to that found in an organism not consisting of the transgenic non-human animal. Thus, prior to rearrangement of a transgene containing various heavy or light chain gene segments, such gene segments may be readily identified, e.g. by hybridization or DNA sequencing, as being from a species of organism other than the transgenic animal. For example, in one embodiment of the invention, various gene segments from the human genome are used in heavy and light chain transgenes in an unrearranged form. In this embodiment, such transgenes are introduced into mice. The unrearranged gene segments of the light and/or heavy chain transgene have DNA sequences unique to the human species which are distinguishable from the endogenous immunoglobulin gene segments in the mouse genome. They may be readily detected in unrearranged form in the germ line and somatic cells not consisting of B-cells and in rearranged form in B-cells.

In an alternate embodiment of the invention, the transgenes comprise rearranged heavy and/or light immunoglobulin transgenes. Specific segments of such transgenes corresponding to functionally rearranged VDJ or VJ segments, contain immunoglobulin DNA sequences which are also clearly distinguishable from the endogenous immunoglobulin gene segments in the mouse.

Such differences in DNA sequence are also reflected in the amino acid sequence encoded by such human immunoglobulin transgenes as compared to those encoded by mouse B-cells. Thus, human immunoglobulin amino acid sequences may be detected in the transgenic non-human animals of the invention with antibodies specific for immunoglobulin epitopes encoded by human immunoglobulin gene segments.

Transgenic B-cells containing unrearranged transgenes from human or other species functionally recombine the appropriate gene segments to form functionally rearranged light and heavy chain variable regions. It is to be understood that the DNA of such rearranged transgenes for the most part will not correspond exactly to the DNA sequence of the gene segments from which such rearranged transgenes were obtained. This is due primarily to the variations introduced during variable recombination and because of mutations introduced by hypermutation during the secondary response. Notwithstanding such modifications in DNA (as well as in amino acid) sequence, it will be readily apparent that the antibody encoded by such rearranged transgenes has a DNA and/or amino acid sequence which is heterologous to that normally encountered in the non-human animal used to practice the invention.

The term "substantial identity", when referring to polypeptides, indicates that the polypeptide or protein in question exhibits at least about 30% identity with an entire naturally occurring protein or a portion thereof, usually at least about 70% identity, and preferably at least about 95% identity. As used herein, the terms "isolated", "substantially pure" and "substantially homogenous" are used interchangeably herein and describe a polypeptide protein which has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially pure protein will typically comprise over about 85 to 90% of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification utilized. A polypeptide is substantially free of naturally-associated components when it is separated from the native contaminants which accompany it in its natural state. Thus, a polypeptide which is synthesized in a cellular system different from the cell from which it naturally originates will be substantially free from its naturally-associated components.

Unrearranged Transgenes

As used herein, an "unrearranged immunoglobulin heavy chain transgene" comprises DNA encoding at least one variable gene segment, one diversity gene segment, one joining gene segment and one constant region gene segment. Each of the gene segments of said heavy chain transgene are derived from, or has a sequence corresponding to, DNA encoding immunoglobulin heavy chain gene segments from a species not consisting of the non-human animal into which said transgene is introduced. Similarly, as used herein, an "unrearranged immunoglobulin light chain transgene" comprises DNA encoding at least one variable gene segment, one joining gene segment and at least one constant region gene segment wherein each gene segment of said light chain transgene is derived from, or has a sequence corresponding to, DNA encoding immunoglobulin light chain gene segments from a species not consisting of the non-human animal into which said light chain transgene is introduced.

Such heavy and light chain transgenes in this aspect of the invention contain the above-identified gene segments in an unrearranged form. Thus, interposed between the V, D and J segments in the heavy chain transgene and between the V and J segments on the light chain transgene are appropriate recombination signal sequences (RSS's). In addition, such transgenes also include appropriate RNA splicing signals to join a constant region gene segment with the VJ or VDJ rearranged variable region.

To the extent that the heavy chain transgene contains more than one C region gene segment, e.g. C$\mu$ and C$\gamma$1 from the human genome, as explained below "switch regions" are incorporated upstream from each of the constant region gene segments and downstream from the variable region gene segments to permit recombination between such constant regions to allow for immunoglobulin class switching, e.g. from IgM to IgG. Such heavy and light immunoglobulin transgenes also contain transcription control sequences including promoter regions situated upstream from the variable region gene segments which contain OCTA and TATA motifs.

In addition to promoters, other regulatory sequences which function primarily in B-lineage cells are used. Thus, for example, a light chain enhancer sequence situated preferably between the J and constant region gene segments on the light chain transgene is used to enhance transgene expression, thereby facilitating allelic exclusion. In the case of the heavy chain transgene, regulatory enhancers and also employed.

Although the foregoing promoter and enhancer regulatory control sequences have been generically described, such regulatory sequences may be heterologous to the nonhuman animal being derived from the genomic DNA from which the heterologous transgene immunoglobulin gene segments are obtained. Alternately, such regulatory gene segments are derived from the corresponding regulatory sequences in the genome of the non-human animal, or closely related species, which contains the heavy and light transgene. Such regulatory sequences are used to maximize the transcription and translation of the transgene so as to induce allelic exclusion and to provide relatively high levels of transgene expression.

In the preferred embodiments, each of the immunoglobulin gene segments contained on the heavy and light Ig transgenes are derived from, or have sequences corresponding to, genomic DNA, cDNA or portions thereof from a species or individual which is heterologous to the non-human animal into which the transgene is to be introduced. As a consequence, when such gene segments are functionally rearranged and hypermutated in the transgenic non-human animal, the heterologous antibody encoded by such heavy and light transgenes will have an amino acid sequence and overall secondary and terteriary structure which provides specific utility against a desired antigen when used therapeutically in the organism from which the Ig gene segments are derived. In addition, such antibodies demonstrate substantially reduced immunogenicity as compared to antibodies which are "foreign" to the organism treated.

For example, in the preferred embodiments, gene segments are derived from human beings. The transgenic non-human animals harboring such heavy and light transgenes are capable of mounting an Ig-mediated immune response to a specific antigen administered to such an animal. B-cells are produced within such an animal which are capable of producing heterologous human antibody. After immortalization, and the selection for an appropriate monoclonal antibody (Mab), e.g. a hybridoma, a source of therapeutic human monoclonal antibody is provided. Such human Mabs have significantly reduced immunogenicity when therapeutically administered to humans.

Examples of antigens which may be used to generate heterologous antibodies in the transgenic animals of the invention containing human immunoglobulin transgenes include bacterial, viral and tumor antigen as well as particular human B- and T-cell antigens associated with graft rejection or autoimmunity.

Although the preferred embodiments disclose the construction of heavy and light transgenes containing human gene segments, the invention is not so limited. In this regard, it is to be understood that the teachings described herein may be readily adapted to utilize immunoglobulin gene segments from a species other than human beings. For example, in addition to the therapeutic treatment of humans with the antibodies of the invention, therapeutic antibodies encoded by appropriate gene segments may be utilized to generate monoclonal antibodies for use in the veterinary sciences. For example, the treatment of livestock and domestic animals with species-related monoclonal antibodies is also contemplated by the invention. Such antibodies may be similarly generated by using transgenes containing immunoglobulin gene segments from species such as bovine, ovine, porcine, equine, canine, feline and the like.

Class Switching

The use of $\mu$ or $\delta$ constant regions is largely determined by alternate splicing, permitting IgM and IgD to be coexpressed in a single cell. The other heavy chain isotypes ($\gamma$, $\alpha$, and $\epsilon$) are only expressed natively after a gene rearrangement event deletes the C$\mu$ and C$\delta$ exons. This gene rearrangement process, termed class switching, occurs by recombination between so called switch segments located immediately upstream of each heavy chain gene (except $\delta$). The individual switch segments are between 2 and 10 kb in length, and consist primarily of short repeated sequences. The exact point of recombination differs for individual class switching events.

The ability of a transgene construction to switch isotypes during B-cell maturation has not been directly tested in transgenic mice; however, transgenes should carry out this function. Durdik et al. (1989) *Proc. Natl. Acad. Sci. USA*, 86, 2346–2350) microinjected a rearranged mouse $\mu$ heavy chain gene construct and found that in four independent mouse lines, a high proportion of the transgenic B-cells expressed the transgene-encoded variable region associated with IgG rather than IgM. Thus, isotype switching appears to have taken place between the transgene and the endogenous $\gamma$ constant region on another chromosome.

As used herein, the term switch sequence thus refers to those DNA sequences responsible for switch recombination. A "switch donor" sequence, typically a $\mu$ switch region, will be 5' (i.e., upstream) of the construct region to be deleted during the switch recombination. The "switch acceptor" region will be between the construct region to be deleted and the replacement constant region (e.g., $\gamma$, $\epsilon$, etc.). As there is no specific site where recombination always occurs, the final gene sequence will typically not be predictable from the construct.

The switch (S) region of the $\mu$ gene, $S_\mu$, is located about 1 to 2 kb 5' to the coding sequence and is composed of numerous tandem repeats of sequences of the form (GAGCT)$_n$(GGGGT), where n is usually 2 to 5 but can range as high as 17. (See T. Nikaido, et al. (1981): *Nature*, 292:845–848.)

Similar internally repetitive switch sequences spanning several kilobases have been found 5' of the other $C_H$ genes. The Sα region has been sequenced and found to consist of tandemly repeated 80-bp homology units, whereas $S_{\gamma 2a}$, $S_{\gamma 2b}$, and $S_{\gamma 3}$ all contain repeated 49-bp homology units very similar to each other. (See, P. Szurek, et al. (1985): *J. Immunol*, 135:620–626 and T. Nikaido, et al. (1982): *J. Biol. Chem.*, 257:7322–7329.) All the sequenced S regions include numerous occurrences of the pentamers GAGCT and GGGGT that are the basic repeated elements of the $S_\mu$ gene (T. Nikaido, et al. (1982): *J. Biol. Chem.*, 257:7322–7329); in the other S regions these pentamers are not precisely tandemly repeated as in $S_\mu$, but instead are embedded in larger repeat units.

The $S_{\gamma 1}$ region has an additional higher-order structure: two direct repeat sequences flank each of two clusters of 49-bp tandem repeats. (See M. R. Mowatt, et al (1986): *J. Immunol.*, 136:2674–2683). Switch regions of human H chain genes have been found very similar to their mouse homologs. Generally, unlike the enzymatic machinery of V-J recombination, the switch machinery can apparently accommodate different alignments of the repeated homologous regions of germline S precursors and then join the sequences at different positions within the alignment. (See, T. H. Rabbits, et al. (1981): *Nucleic Acids Res.*, 9:4509–4524 and J. Ravetch, et al. (1980): *Proc. Natl. Acad. Sci. USA*, 77:6734–6738.)

Induction of class switching appears to be associated with sterile transcripts that initiate upstream of the switch segments (Lutzker et al., 1988 *Mol. Cell. Biol.*, 8, 1849; Stavnezer et al. 1988 *Proc. Natl. Acad. Sci. USA*, 85, 7704; Esser and Radbruch 1989 *EMBO J.*, 8, 483; Berton et al. 1989 *Proc. Natl. Acad. Sci. USA*, 86, 2829; Rothman et al. 1990 *Int. Immunol.* 2, 621). For example, the observed induction of the γ1 sterile transcript by IL-4 and inhibition by IFN-γ correlates with the observation that IL-4 promotes class switching to γ1 in B-cells in culture, while IFN-γ inhibits γ1 expression. Ideally then, transgene constructs that are intended to undergo class switching should include all of the cis-acting sequences necessary to regulate these sterile transcripts. An alternative method for obtaining class switching in transgenic mice (σμ and εμ) involves the inclusion of the 400 bp direct repeat sequences that flank the human μ gene (Yasui et al. 1989 *Eur. J. Immunol.*, 19, 1399). Homologous recombination between these two sequences deletes the μ gene in IgD-only B-cells.

Monoclonal Antibodies

Monoclonal antibodies can be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.*, 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Various techniques useful in these arts are discussed, for example, in Harlow and Lane, *Antibodies: A Laboratory Manual*, Cold Spring Harbor, N.Y. (1988) including: immunization of animals to produce immunoglobulins; production of monoclonal antibodies; labeling immunoglobulins for use as probes; immunoaffinity purification; and immunoassays.

The Transgenic Primary Repertoire

A. The Human Immunoglobulin Loci

An important requirement for transgene function is the generation of a primary antibody repertoire that is diverse enough to trigger a secondary immune response for a wide range of antigens. The size of the human immunoglobulin loci encoding the various gene segments for heavy and light chains is quite large. For example, in the human genome the three separate loci for the λ light chain locus, the κ light chain locus and the heavy chain locus together occupy over 5 Mb of DNA or almost 0.2% of the entire genome. Each locus consists of multiple variable segments that recombine during B-cell development with a joining region segment (and, the heavy chain locus with diversity region segments) to form complete V region exons. Such rearranged light chain genes consist of three exons: a signal peptide exon, a variable region exon and a constant region exon. The rearranged heavy chain gene is somewhat more complex. It consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

Figure 2:
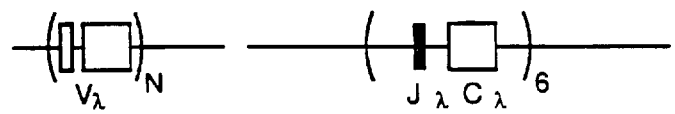
FIG. 2 depicts the human λ chain locus.

Approximately 40% of human serum antibody molecules contain λ light chains. The structure of this locus, which maps to chromosome 22, is the least well characterized (FIG. 2). It consists of an unknown number of V segments upstream of a tandem array of six constant region genes, each of which is linked to a single J segment. In addition, two more constant region segments with associated J segments have been isolated, although their linkage with the rest of the λ cluster has not been established, and it is not known if they are used. E. Selsing, et al., "Immunoglobulin Genes", Academic Press, T. Honjo, F. W. Alt and T. H. Rabbitts, eds. (1989).

Figure 3:
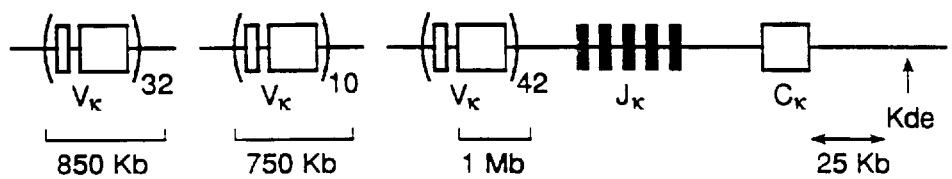
FIG. 3 depicts the human κ chain locus.

The κ light chain locus is spread out over three clusters on chromosome 2 (FIG. 3). The first two clusters, covering 850 and 250 kb respectively contain only variable region gene segments. The third cluster, covering about 1 Mb, contains approximately 40 V gene segments upstream of a cluster of 5 J segments followed by a single constant region gene segment. A total of 84 V gene segments have been identified, and approximately half of these are thought to be pseudogenes (Zachau (1989) in Immunoglobulin Genes, Academic Press, T. Honjo, F. W. Alt, and T. H. Rabbitts, eds. pp. 91–110). Approximately 25 kb downstream of the CK region there is a "k deleting element" (κde). The κde sequence recombines with upstream sequences, causing the deletion of the κ constant region in λ light chain expressing B-cells. This leads to isotopic exclusion in cells that successfully rearrange both κ and λ genes.

Figure 4:
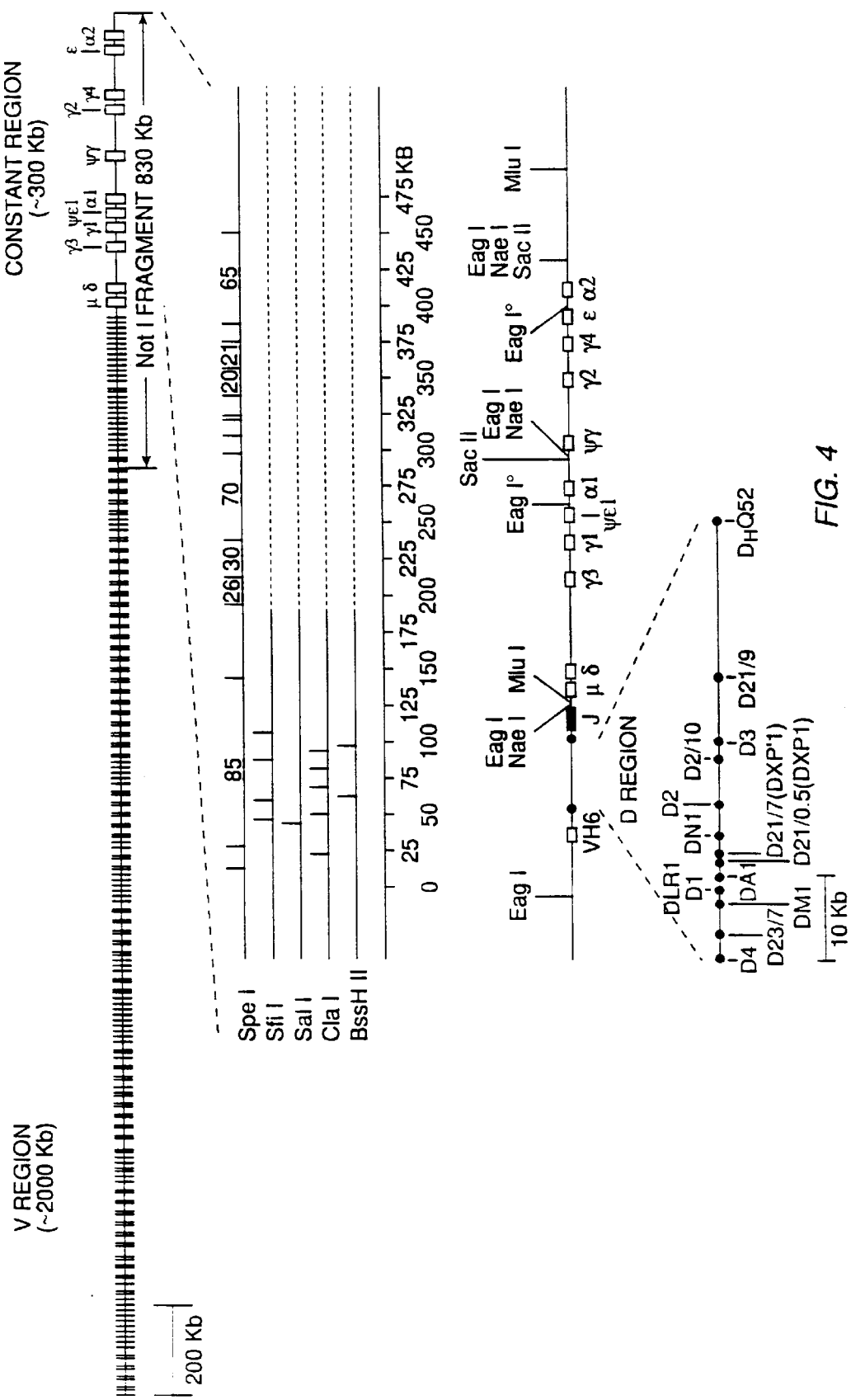
FIG. 4 depicts the human heavy chain locus.

The human heavy chain locus is the largest and most diverse. It consists of approximately 200 V gene segments spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14 (FIG. 4). The heavy chain V segments can be grouped into six families on the basis of sequence similarity. There are approximately 60 members of the $V_H1$ family, 30 $V_H2$ segments, 80 $V_H3$ segments, 30 $V_H4$ segments, three $V_H5$ segments, and one $V_H6$ segment. Berman, J. E., et al. (1988), *EMBO J.*, 7, 727–738. In the human heavy chain locus, the members of individual V families are intermingled, unlike the mouse locus where related V segments are clustered. The single member of the VH6 family is the most proximal of the V segments, mapping to within 90 kb of the constant region gene segments. Sato, T., et al. (1988), *Biochem. Biophys. Res. Comm.*, 154, 265–271. All of the functional D and J segments appear to lie in this 90 kb region (Siebenlist, et al. (1981), *Nature*, 294, 631–635; Matsuda, et al. (1988), *EMBO J.*, 7, 1047–1051; Buluwela, et al. (1988), *EMBO J.*, 7, 2003–2010; Ichihara, et al. (1988), *EMBO J.*, 7, 4141–4150; Berman, et al. (1988), *EMBO J.*, 7, 727–738).

B. Gene Fragment Transgenes

1. Heavy Chain Transgene

In a preferred embodiment, immunoglobulin heavy and light chain transgenes comprise unrearranged genomic DNA from humans. In the case of the heavy chain, a preferred transgene comprises a NotI fragment having a length between 670 to 830 kb. The length of this fragment is ambiguous because the 3' restriction site has not been accurately mapped. It is known, however, to reside between the α1 and ψα gene segments (see FIG. 4). This fragment contains members of all six of the known $V_H$ families, the D and J gene segments, as well as the $\mu$, $\delta$, $\gamma3$, $\gamma1$ and α1 constant regions. Berman, et al. (1988), *EMBO J.*, 7, 727–738. A transgenic mouse line containing this transgene correctly expresses all of the heavy chain classes required for B-cell development as well as a large enough repertoire of variable regions to trigger a secondary response for most antigens.

2. Light Chain Transgene

A genomic fragment containing all of the necessary gene segments and regulatory sequences from a human light chain locus may be similarly constructed. Such a construct is described in the Examples.

C. Transgenes Generated Intracellularly by In Vivo Recombination

It is not necessary to isolate the all or part of the heavy chain locus on a single DNA fragment. Thus, for example, the 670–830 kb NotI fragment from the human immunoglobulin heavy chain locus may be formed in vivo in the non-human animal during transgenesis. Such in vivo transgene construction is produced by introducing two or more overlapping DNA fragments into an embryonic nucleus of the non-human animal. The overlapping portions of the DNA fragments have DNA sequences which are substantially homologous. Upon exposure to the recombinases contained within the embryonic nucleus, the overlapping DNA fragments homologously recombined in proper orientation to form the 670–830 kb NotI heavy chain fragment.

It is to be understood, however, that in vivo transgene construction can be used to form any number of immunoglobulin transgenes which because of their size are otherwise difficult, or impossible, to make or manipulate by present technology. Thus, in vivo transgene construction is useful to generate immunoglobulin transgenes which are larger than DNA fragments which may be manipulated by YAC vectors (Murray and Szostak (1983), *Nature*, 305, 189–193). Such in vivo transgene construction may be used to introduce into a non-human animal substantially the entire immunoglobulin loci from a species not consisting of the transgenic non-human animal. Thus, although several groups have successfully constructed libraries containing 50–200 kb of DNA fragments in YAC vectors (Burke, et al. (1987), *Science*, 236, 806–812; Traver, et al. (1989), *Proc. Natl. Acad. Sci. USA*, 86, 5898–5902) and used polyamine condensation to produce YAC libraries ranging in size from 200 to approximately 1000 kb (McCormick, et al. (1989), *Proc. Natl. Acad. Sci USA*, 86, 9991–9995), multiple overlapping fragments covering substantially more than the 670–830 kb NotI fragment of the human constant region immunoglobulin loci are expected to readily produce larger transgenes by the methods disclosed herein.

In addition to forming genomic immunoglobulin transgenes, in vivo homologous recombination may also be utilized to form "mini-locus" transgenes as described in the Examples.

In the preferred embodiments utilizing in vivo transgene construction, each overlapping DNA fragment preferably has an overlapping substantially homologous DNA sequence between the end portion of one DNA fragment and the end portion of a second DNA fragment. Such overlapping portions of the DNA fragments preferably comprise about 500 bp to about 2000 bp, most preferably 1.0 kb to 2.0 kb. Homologous recombination of overlapping DNA fragments to form transgenes in vivo is further described in commonly assigned U.S. Patent Application entitled "Intracellular Generation of DNA by Homologous Recombination of DNA Fragments" filed Aug. 29, 1990, under U.S. Ser. No. 07/574,747.

D. Minilocus Transgenes

As used herein, the term "immunoglobulin minilocus" refers to a DNA sequence (which may be within a longer sequence), usually of less than about 150 kb, typically between about 25 and 100 kb, containing at least one each of the following: a functional variable (V) gene segment, a functional joining (J) region segment, a functional constant (C) region gene segment, and—if it is a heavy chain minilocus—a functional diversity (D) region segment, such that said DNA sequence contains at least one substantial discontinuity (e.g., a deletion, usually of at least about 2 to 5 kb, preferably 10–25 kb or more, relative to the homologous genomic DNA sequence). A light chain minilocus transgene will be at least 25 kb in length, typically 50 to 60 kb. A heavy chain transgene will typically be about 70 to 80 kb in length, preferably at least about 60 kb with two constant regions operably linked to switch regions, versus at least about 30 kb with a single constant region and incomplete switch regions. Furthermore, the individual elements of the minilocus are preferably in the germline configuration and capable of undergoing gene rearrangement in the pre-B cell of a transgenic animal so as to express functional antibody molecules with diverse antigen specificities encoded entirely by the elements of the minilocus.

In an alternate preferred embodiment, immunoglobulin heavy and light chain transgenes comprise one or more of each of the V, D, J and C gene segments. At least one of each appropriate type gene segment is incorporated into the minilocus transgene. With regard to the C segments for the heavy chain transgene, it is preferred that the transgene contain at least one $\mu$ gene segment and at least one other constant region gene segment, more preferably a $\gamma$ gene segment, and most preferably $\gamma3$ or $\gamma1$. This preference is to allow for class switching between IgM and IgG forms of the encoded immunoglobulin to provide for somatic mutation and the production of a secretable form of high affinity non-IgM immunoglobulin. Other constant region gene segments may also be used such as those which encode for the production of IgD, IgA and IgE.

The heavy chain J region segments in the human comprise six functional J segments and three pseudo genes clustered in a 3 kb stretch of DNA. Given its relatively compact size and the ability to isolate these segments together with the $\mu$ gene and the 5' portion of the $\delta$ gene on a single 23 kb SFiI/SpeI fragment (Sado, et al. (1988), *Biochem. Bioshys. Res. Comm.*, 154, 264271), it is preferred that all of the J region gene segments be used in the mini-locus construct. Since this fragment spans the region between the $\mu$ and $\delta$ genes, it is likely to contain all of the 3' cis-linked regulatory elements required for $\mu$ expression. Furthermore, because this fragment includes the entire J region, it contains the heavy chain enhancer and the $\mu$ switch region (Mills, et al. (1983), *Nature*, 306, 809; Yancopoulos and Alt (1986), *Ann. Rev. Immunol.*, 4, 339–368). It also contains the transcription start sites which trigger VDJ joining to form primary repertoire B-cells (Yancopoulos and Alt (1985), *Cell*, 40, 271–281). Alternatively, a 36 kb BssHII/SpeII fragment, which includes part on the D region, may be used in place of the 23 kb SfiI/SpeI1 fragment. The use of such a fragment increases the amount of 5' flanking sequence to facilitate efficient D-to-J joining.

The human D region consists of 4 or 5 homologous 9 kb subregions, linked in tandem (Siebenlist, et al. (1981), *Nature*, 294, 631–635). Each subregion contains up to 10 individual D segments. Some of these segments have been mapped and are shown in FIG. 4. Two different strategies are used to generate a mini-locus D region. The first strategy involves using only those D segments located in a short contiguous stretch of DNA that includes one or two of the repeated D subregions. A candidate is a single 15 kb fragment that contains 12 individual D segments. This piece of DNA consists of 2 contiguous EcoRI fragments and has been completely sequenced (Ichihara, et al. (1988), *EMBO J.*, 7, 4141–4150). Twelve D segments should be sufficient for a primary repertoire. However, given the dispersed nature of the D region, an alternative strategy is to ligate together several non-contiguous D-segment containing fragments, to produce a smaller piece of DNA with a greater number of segments.

At least one, and preferably more than one V gene segment is used to construct the heavy chain minilocus transgene. A 10–15 kb piece of DNA containing one or two unrearranged V segments together with flanking sequences is isolated. A clone containing such DNA is selected using a probe generated from unique 5' sequences determined from the transcribed V region of a characterized human hybridoma such as that which produces anti-cytomegalovirus antibody (Newkirk et al. (1988) *J. Clin. Invest.*, 81, 1511–1518). The 5' untranslated sequence of the heavy chain mRNA is used to construct a unique nucleotide probe (preferably about 40 nucleotides in length) for isolating the original germline V segment that generated this antibody. Using a V segment that is known to be incorporated in an antibody against a known antigen not only insures that this V segment is functional, but aids in the analysis of transgene participation in secondary immune responses. This V segment is fused with the minilocus D region and constant region fragments, discussed previously, to produce a mini-locus heavy chain transgene.

Alternatively, a large, contiguous stretch of DNA containing multiple V region segments is isolated from a YAC library. Different sized pieces of DNA, containing different numbers of V region segments, are tested for their ability to provide a human antibody repertoire in the minilocus transgene construct. It is also possible to build one large fragment from several non-contiguous V segment containing fragments using YAC vectors (Murray and Szostak (1983), *Nature*, 305, 189–193), F factor-based plasmids (O'Conner, et al. (1989), *Science*, 244, 1307–1312) or the aforementioned in vivo construction using recombination of overlapping fragments. Alternatively, a synthetic V region repertoire (described hereinafter) may be used.

A minilocus light chain transgene may be similarly constructed from the human $\lambda$ or $\kappa$ immunoglobulin locus. Construction of a $\kappa$ light chain mini-locus is very similar to construction of the heavy chain mini-locus, except that it is much simpler because of its smaller size and lower complexity. The human $\kappa$ locus contains only one constant region segment; and this segment, together with 5' and 3' enhancers, and all 5 of the functional J segments, can be isolated on a single 10 kb DNA fragment. This fragment is co-injected together with a minilocus V region constructed as described for the heavy chain minilocus.

Thus, for example, an immunoglobulin heavy chain minilocus transgene construct, e.g., of about 75 kb, encoding V, D, J and constant region sequences can be formed from a plurality of DNA fragments, at least two, three or four of which each are either a V region sequence, a D region sequence, a J and constant region sequence, a D and J and constant region sequence or a constant region sequence, with each sequence being substantially homologous to human gene sequences. Preferably, the sequences are operably linked to transcription regulatory sequences and are capable of undergoing rearrangement. With two or more appropriately placed constant region sequences (e.g., $\mu$ and $\gamma$) and switch regions, switch recombination also occurs. An exemplary light chain transgene construct similarly formed from a plurality of DNA fragments, substantially homologous to human DNA and capable of undergoing rearrangement will include at least two, three or four DNA fragments, encoding V, D and constant regions, each fragment comprising either a V region sequence, J and constant region sequence or a constant region sequence.

E. Methods for Determining Functional V Gene Segments and for Generating Synthetic V Segment Repertoire Of the various families of gene segments, i.e., V, D, J and C region gene segments, the number of V gene segments generally far surpasses the number of corresponding gene segments for the D, J and C region gene segments. By analogy to the rabbit system wherein a single V gene segments is utilized by approximately 90% of the antibodies produced (Knight and Becker (1990), *Cell*, 60, 963–970), it is possible to produce heavy and light transgenes containing a limited number of V region gene segments, and as few as one V region gene segments. Therefore, it is desirable to have a method to determine which V region gene segments are utilized by a particular organism, such as the human being, when mounting an immunoglobulin-mediated immune response. According to this approach, a single V gene segment when combining with the J or DJ gene segments is capable of providing sufficient diversity at CDR3 for the generation of a primary repertoire which upon somatic mutation is able to provide further diversity throughout the variable region, e.g. at CDR1 and CDR2 for the production of high affinity antibodies.

In this aspect of the invention, methods and vectors are provided for determining which V gene segments are commonly utilized by an organism during an immune response. This method is based on determining which V segments are found in cDNA synthesized from B-cell polyA+ RNA. Such methods and vectors may also be used to facilitate the construction of a synthetic V segment repertoire.

Figure 5:
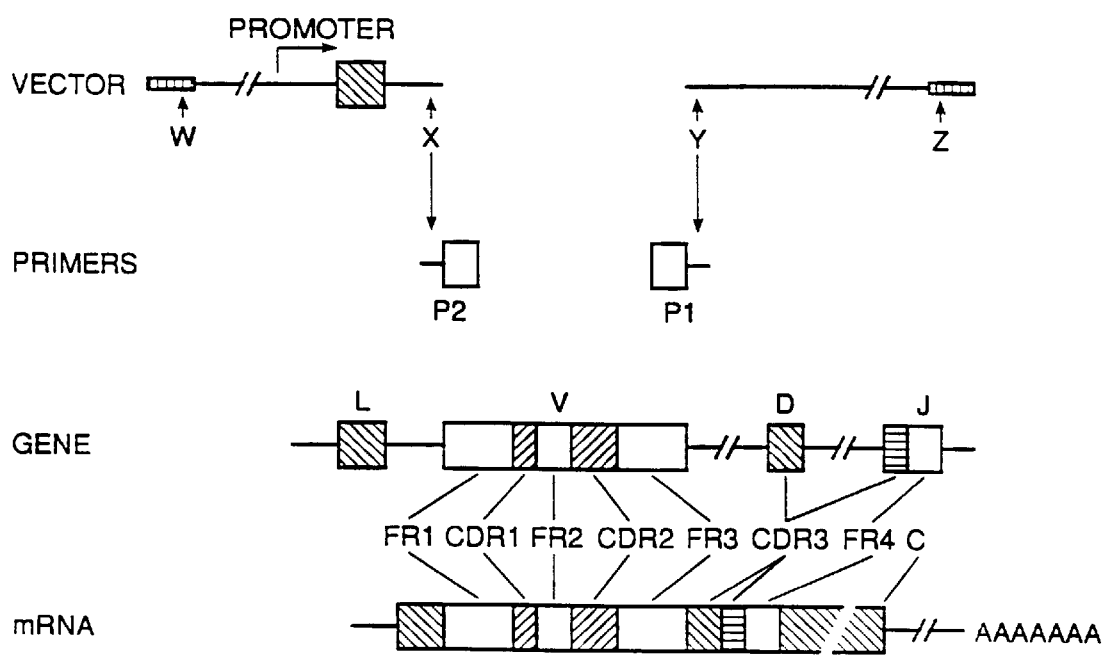
FIGS. 5 and 6 depict the strategy for generating a synthetic V segment repertoire.
Figure 6:
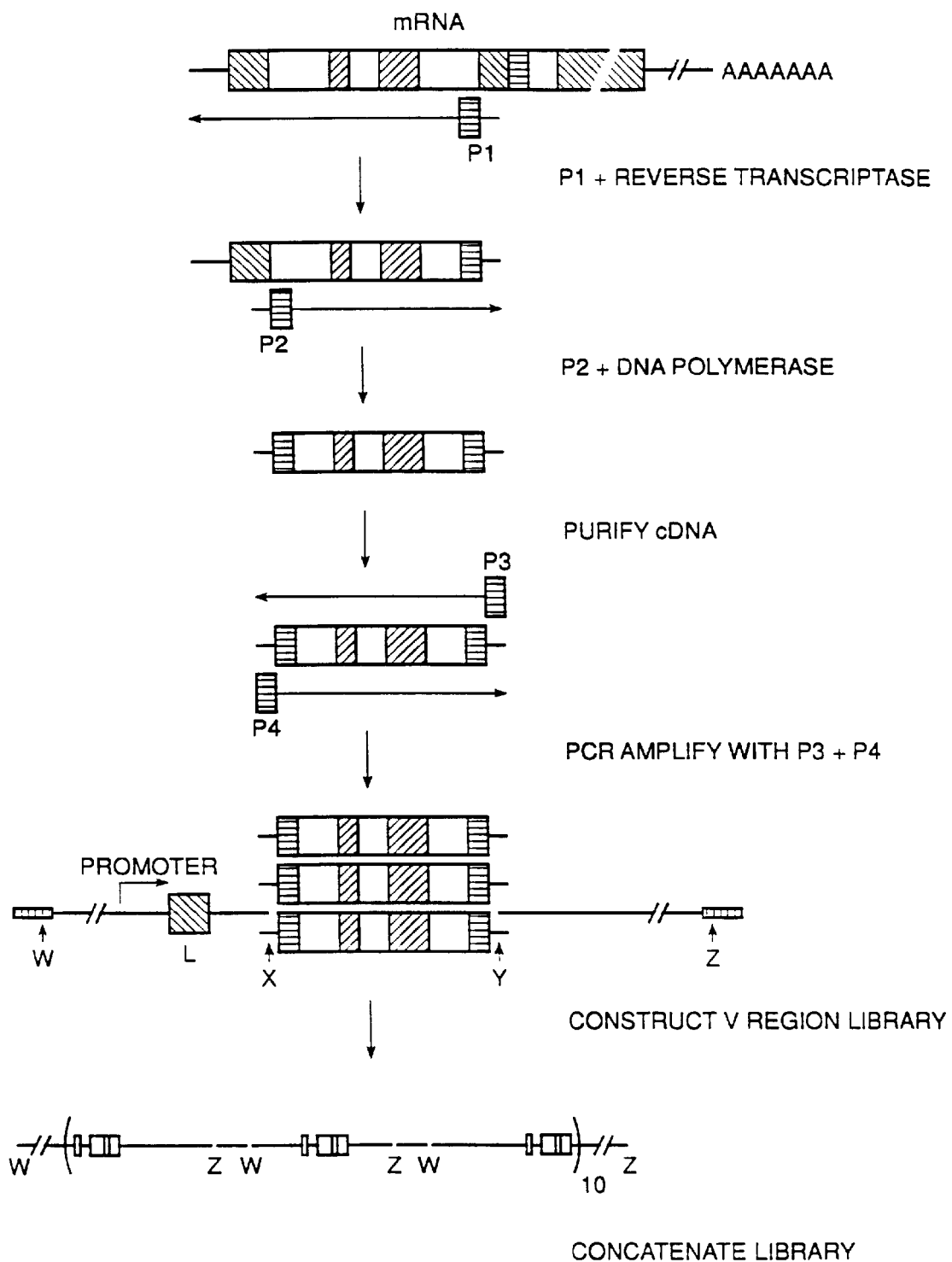

The outline of this strategy for identifying heavy chain V segments and for generating a synthetic V segment repertoire is depicted in FIGS. 5 and 6. It is similarly applicable for identifying light chain V segments with appropriate modification. The first step is the construction of a cloning vector. The preferred starting material is a DNA fragment (approximately 2 kb) containing an unrearranged V segment together with 5' and 3' flanking sequences. This fragment is cloned into a plasmid such as pGP1 or pGP2 described hereinafter containing a polylinker site flanked by the rare cutting restriction sites designated "w" and "z" in the FIGS. 5 and 6 (the polylinkers and restriction sites of pGP1 and pGP2 are described in the Examples). Oligonucleotide directed mutagenesis is then used to introduce two new restriction sites, "x" and "y" (generally each about 6 nucleotides in length). Restriction site "x" is placed approximately 20 nucleotides from the 3' end of the intron between the signal and V segment exon. Restriction site "y" is placed approximately 20 nucleotides 3' of the V segment junction, within the 23 bp spacer between the heptamer and nonomer recombination signal sequences. Cutting the resulting plasmid with enzymes "x" and "y" removes the second exon (V segment), leaving the 5' flanking sequences, the V region promoter, the signal peptide exon, the intron, a gap flanked by "x" and "y" ends, the outside half of the recombination signal sequence, and the 3' flanking sequences. This plasmid is called pVH1.

The second step is the synthesis of four sets of oligonucleotide primers, P1 through P4. P1 and P2 are non-unique oligomers having approximately 50 nucleotides each which are used to prime double stranded cDNA synthesis. P1 starts (going 5' to 3') with about 20 nucleotides of sequence homologous to the antisense strand of the recombination signal sequence in pVH1 (including the recognition sequence of restriction enzyme "y"), and continues with approximately 30 nucleotides of antisense sequence hybridizing with about the last 30 nucleotides of the VH framework region 3 (FR3). Random bases are incorporated over about the last 30 nucleotides so as to generate a set of primers that hybridize with all of the different VH families. The second oligonucleotide, P2, is in the sense orientation, and is homologous to the approximately 50 nucleotides beginning with the restriction site "x" in pVH1. This includes the "x" restriction site, about the last 20 nucleotides of the intron, and about the first 30 nucleotides of FR1. Again, about the last 30 nucleotides are non-unique so as to accommodate different VH region segments. Oligonucleotides P3 and P4 are homologous to about the first 20 nucleotides of P1 and P2 respectively. These oligos are unique so as to avoid introducing new mutations into the V segments and are used to amplify double stranded cDNA by way of the polymerase chain reaction (PCR).

The 3' terminal portions of primers P1 and P2 which are capable of hybridizing to and priming the synthesis of the variable segments of the heavy or light immunoglobulin locus may be readily determined by one skilled in the art. For example, the nucleotide sequence for a number of human VH genes have been published, see e.g. Berman, J. E., et al. (1988), *EMBO J.*, 7, 727–738 and Kabat, E. A., et al. (1987), *Sequences of Protein of Immunological interests*, U.S. Dept. Health & Human Services, Washington, D.C. Similarly, when used to identify and/or generate V segments of the human light immunoglobulin locus, the appropriate 3' sequence portions of primers P1 and P2 may readily be determined from published sequences. See e.g Kabat, E. A., et al., supra. In general, those nucleotide positions which are conserved amongst various V segments are also conserved in the 3' portion of the P1 and P2 primers. For those nucleotide positions wherein variation is observed amongst variable segments, such nucleotide positions in the corresponding P1 and P2 primers are similarly varied to provide P1 and P2 primers which comprise a pool of primers which are capable of hybridizing to different VH or VL segments.

The next step is to use these oligonucleotide primers to generate a library of human heavy-chain V-region cDNA sequences in the vector pHV1. P1 is used to prime first strand cDNA synthesis from human B-cell polyA+ RNA. The RNA is base hydrolyzed, and second strand synthesis primed with P2. Full length, double stranded cDNA is then purified on an acrylamide gel, electroeluted, and used as template for polymerase chain reaction (PCR) amplification using oligonucleotide primers P3 and P4. Alternatively, cDNA is first synthesized by conventional methods and this cDNA is used as a template for the P1 primed reactor. The amplified product (approximately 0.3 kb) is then gel purified, cleaved with restriction enzymes "x" and "y", and cloned into pHV1.

The resulting cDNA library represents a synthetic genomic library of variable region segments and offers three advantages over a conventional genomic library of variable segments. First, this library contains no pseudogenes, while a conventional library would contain up to 50% pseudogene sequences. Second, the synthetic library is more compact than a conventional library, containing one functional V segment per 2 kb of DNA, as opposed to one functional segment per 20 kb. Finally, this approach leaves the V segment promoter sequences accessible to manipulation.

Such a cDNA library may be biased towards particular germline V segments because of differential expression. The two sources of bias are: (i) differential rates of V segment recombination, and (ii) differential selection of V segment expressing B-cell clones. The first source of bias is dealt with in two ways. First, fetal tissue is avoided as a source of B-cell RNA, as the bias is most pronounced in the fetal immunoglobulin repertoire. Second, the semi-random primers, P1 and P2, are divided into pools, each of which selectively cross-hybridizes with different V segment families. These primers are then used to generate 4 to 6 separate libraries, thus insuring that all of the V region families are represented. The second source of bias, differential selection of B-cell clones, is also dealt with in two analogous ways. First, a source of RNA that includes the minimum fraction of antigen selected B-cells is used. Lymph nodes and spleen are avoided. Adult bone marrow is one source of unselected B-cells. However, it may contain a high proportion of transcribed pseudogene sequences from pre-B-cells. Another source of RNA is whole blood. Ninety percent of circulating B-cells are immature $\mu$ or $\mu$, $\delta$ expressing cells, and are recent bone marrow immigrants. However, the level of antigen selected IgG expressing cells can vary depending on the immune state of the individual. Therefore, isolated polyA+ RNA is checked for selected B-cell sequences by northern blot hybridization with $\gamma$ specific probes. If it is more practical to use spleen RNA, and if this RNA contains a high fraction of IgG sequences, a second approach is used to minimize selection bias. The first strand of cDNA synthesis is primed with about a 40 nucleotide constant-region exon 2 primer that is specific for IgM transcripts. Second strand syntheses is then primed with P2, and a third round of synthesis primed with P1. The cDNA from this third round of synthesis provides the template for PCR amplification using P3 and P4.

Once the variable region library has been generated, the V segments used therein may by identified by standard techniques, e.g. by way of sequencing and/or hybridization with family specific or segment specific oligonucleotides as well as differential amplification by PCR methods. Such characterization of the V segment library provides information as to the frequency and distribution of V segment utilization in a particular organism and as a consequence, the identification of V segments which may be used in the construction of the various transgenes of the invention. Thus, one or more predominant V gene segments may be used in the above described mini-locus transgene construct. Further, selected clones from such a library may be used to identify genomic fragments containing frequently used V segments to facilitate identification of genomic fragments containing a particular desired V segment.

In addition, a synthetic V segment repertoire may be constructed by concatenation of the library sequences. Large repeating transgene tandem arrays, containing hundreds of copies of the injected sequence, are commonly generated in the production of transgenic mice. These tandem arrays are usually quite stable. However, to ensure the stability of the synthetic V region, blocks of random DNA between each 2 kb V region segment are preferably introduced. These blocks of random DNA are prepared by digesting and then religating genomic DNA, so as to prevent the insertion of dominant regulatory elements. Genomic DNA is preferably digested with four frequent cutting restriction enzymes: AluI, DpnI, HaeIII, and RsaI. This digest produces blunt ended fragments with an average length of 64 nucleotides. Fragments in the size range of 50 to 100 nucleotides are eluted from an acrylamide gel, and religated. The relegated DNA is partially digested with MboI and size fractionated. Fragments in the range of 0.5 to 2 kb are cloned into the BamHI or BglII site of the polylinker of the vector used to generate pVH1.

The random sequence library is combined with the synthetic V segment library to create a synthetic V segment repertoire. Inserts from the random sequence library are released with the enzymes "w" and "z", and purified away from vector sequences. Inserts from the synthetic V segment library are isolated by cutting with "w" and "z". Before purifying the V segment inserts, this DNA is treated with calf-intestinal phosphatase, to prevent self ligation. The V segment inserts are then ligated together with the random inserts to generate an alternating tandem array comprising a synthetic V segment repertoire. This ligation mixture is size selected on a sucrose gradient, and the 50–100 kb fraction microinjected together with, for example, a D-J-constant mini-locus construct. By directly injecting the synthetic V segment repertoire without an intervening cloning step, it is possible to take advantage of the fact that tandem arrays of injected fragments become inserted at a single site. In this case such tandem arrays are not completely redundant but lead to further diversity. Alternatively, the synthetic V segment repertoire may be combined with a D-J-C minilocus to form a heavy chain transgene.

A synthetic light chain immunoglobulin segment repertoire may be similarly constructed using appropriate primers for the light chain locus.

Functional Disruption of Endogenous Immunoglobulin Loci

The expression of successfully rearranged immunoglobulin heavy and light transgenes is expected to have a dominant effect by suppressing the rearrangement of the endogenous immunoglobulin genes in the transgenic nonhuman animal. However, another way to generate a nonhuman that is devoid of endogenous antibodies is by mutating the endogenous immunoglobulin loci. Using embryonic stem cell technology and homologous recombination, the endogenous immunoglobulin repertoire can be readily eliminated. The following describes the functional description of the mouse immunoglobulin loci. The vectors and methods disclosed, however, can be readily adapted for use in other non-human animals.

Briefly, this technology involves the inactivation of a gene, by homologous recombination, in a pluripotent cell line that is capable of differentiating into germ cell tissue. A DNA construct that contains an altered, copy of a mouse immunoglobulin gene is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells entirely derived from the mutant cell line. Therefore, by breeding the chimeric mice it is possible to obtain a new line of mice containing the introduced genetic lesion (reviewed by Capecchi (1989), *Science,* 244, 1288–1292).

Because the mouse λ locus contributes to only 5% of the immunoglobulins, inactivation of the heavy chain and/or κ-light chain loci is sufficient. There are three ways to disrupt each of these loci, deletion of the J region, deletion of the J-C intron enhancer, and disruption of constant region coding sequences by the introduction of a stop codon. The last option is the most straightforward, in terms of DNA construct design. Elimination of the $\mu$ gene disrupts B-cell maturation thereby preventing class switching to any of the functional heavy chain segments. The strategy for knocking out these loci is outlined below.

To disrupt the mouse $\mu$ and κ genes, targeting vectors are used based on the design employed by Jaenisch and co-workers (Zijlstra, et al. (1989), *Nature,* 342, 435–438) for the successful disruption of the mouse β2-microglobulin gene. The neomycin resistance gene (neo), from the plasmid pMCIneo is inserted into the coding region of the target gene. The pMCIneo insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zijlstra, et al., supra.).

Figure 7:
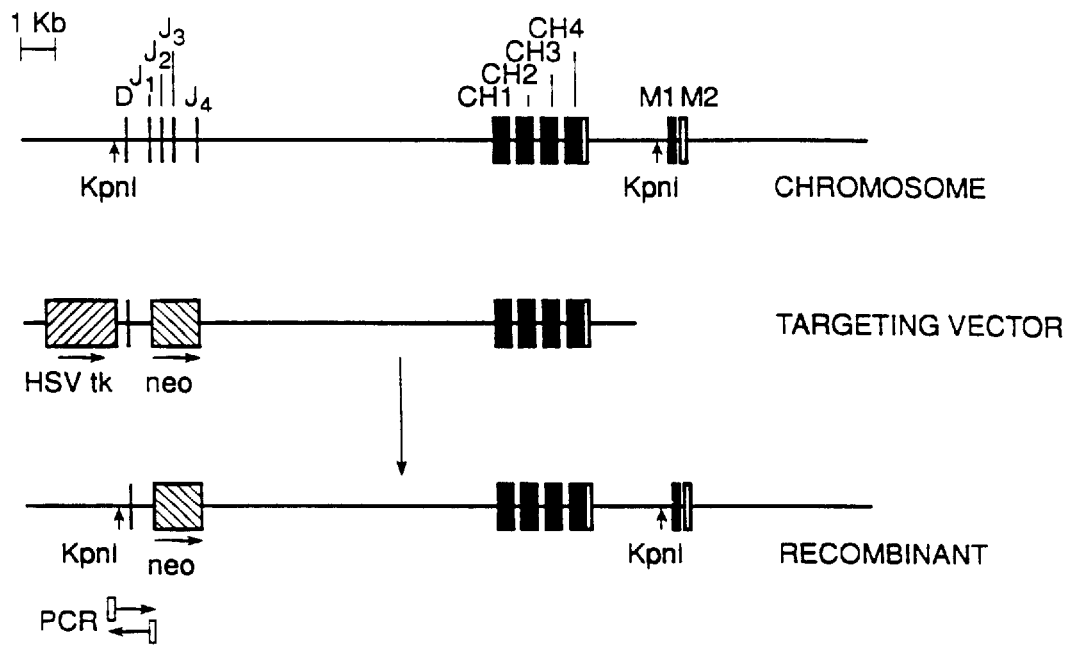
FIG. 7 depicts the strategy for functional disruption of endogenous immunoglobulin loci.

The targeting vectors for disrupting the heavy chain locus are illustrated in FIG. 7. The primary strategy for disrupting the heavy chain locus is the elimination of the J region. This region is fairly compact in the mouse, spanning only 1.3 kb. To construct a gene targeting vector, a 15 kb KpnI fragment containing all of the secreted A constant region exons from mouse genomic library is isolated. The 1.3 kb J region is replaced with the 1.1 kb insert from pMCIneo. The HSV tk gene is then added to the 5' end of the KpnI fragment. Correct integration of this construct, via homologous recombination, will result in the replacement of the mouse $J_H$ region with the neo gene (FIG. 7). Recombinants are screened by PCR, using a primer based on the neo gene and a primer homologous to mouse sequences 5' of the KpnI site in the D region.

Alternatively, the heavy-chain locus is knocked out by disrupting the coding region of the $\mu$ gene. This approach involves the same 15 kb KpnI fragment used in the previous approach. The 1.1 kb insert from pMCIneo is inserted at a unique BamHI site in exon II, and the HSV tk gene added to the 3' KpnI end. Double crossover events on either side of the neo insert, that eliminate the tk gene, are then selected for. These are detected from pools of selected clones by PCR amplification. One of the PCR primers is derived from neo sequences and the other from mouse sequences outside of the targeting vector. The functional disruption of the mouse immunoglobulin loci is presented in the Examples.

Transgenic Non-Human Animals Containing Rearranged Immunoglobulin Heavy and Light Transgenes A premise underlying the previously discussed transgenic animals containing unrearranged mini-locus Ig transgenes is that it is possible to generate a complete antibody repertoire without including all of the variable gene segments found in the natural immunoglobulin locus. Theoretically, it is possible to reduce the number of different sequences that contribute to the primary repertoire without reducing the secondary repertoire. As long as there is enough diversity in the primary repertoire to trigger a T-cell dependent response for any given antigen, somatic hypermutation should be capable of delivering a high affinity antibody against that antigen.

This concept is taken a step further in this aspect of the invention wherein a full heterologous antibody repertoire is generated entirely by somatic mutation. The antigen combining site is created by the interface between the amino-terminal heavy chain domain and the amino-terminal light chain domain. The CDR1, 2 and 3 residues within each of these domains that interact with the antigen are located on three different loops that connect β strands. As previously described, these regions have the greatest sequence diversity between different antibody molecules recognizing different antigens. Thus, the antibody repertoire is determined by sequence diversity at CDR1, 2, and 3. The diversity at CDR1, 2, and 3 that gives rise to a complete antibody repertoire comes from three sources: recombinational diversity, junctional diversity, and somatic mutation. Recombinational diversity at CDR1 and 2 comes from the choice of different V segments containing different CDR1 and 2 sequences. Recombinational diversity at CDR 3 comes from the choice of different D and J segments. Junctional diversity contributes only to CDR3 diversity, while somatic mutation, acting across the entire V region, contributes to diversity at all three complimentarity determining regions. Recombinational and junctional diversity together constitute the diversity of the primary repertoire (FIG. 1). Thus VDJ joining generates a set of IgM expressing primary B-cells.

Figure 8:
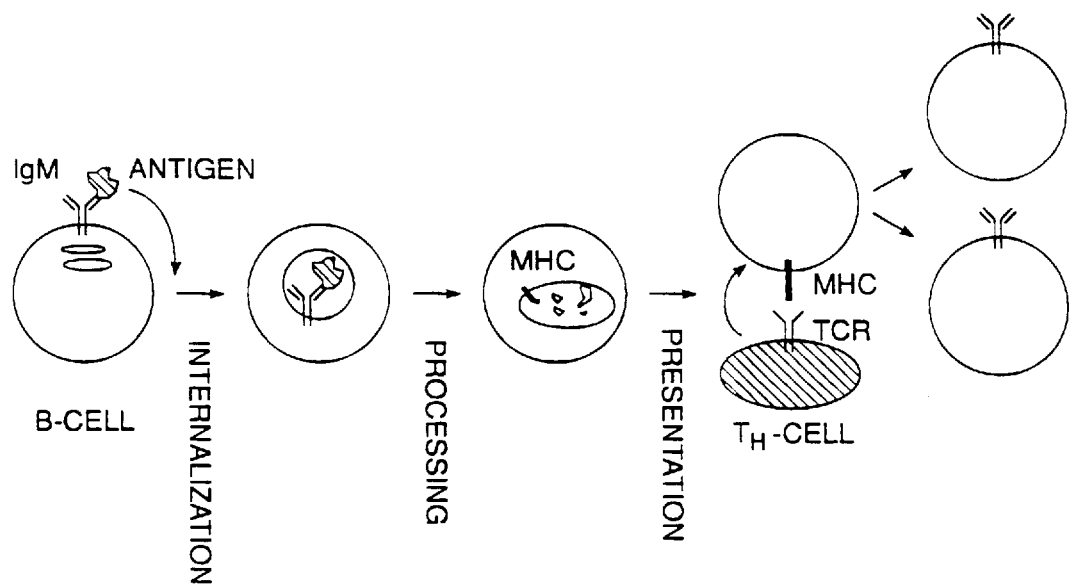
FIG. 8 depicts the T-cell mediated secondary response leading to maturation of the B-cell.

Any primary repertoire B-cell that expresses a cell surface IgM molecule with a certain minimal affinity for a foreign antigen, internalizes that antigen as IgM and cycle off the cell surface. The antigen is then processed and associated peptides are presented on the cell surface by class II MHC molecules. If enough foreign antigen is presented at the cell surface this, triggers a T-cell response that in turn triggers the T-cell dependent maturation of the B-cell. This is the so-called secondary response (FIG. 8). Part of this response involves the hypermutation of the variable portion of the immunoglobulin genes. Thus a B-cell clone undergoing a secondary response constantly gives rise to new clones with altered immunoglobulin molecules. Those clones with higher affinities for the foreign antigen are selectively expanded by helper T-cells, giving rise to affinity maturation of the expressed antibody. Because somatic hypermutation takes place across the entire V region, there is no theoretical limit to the process of affinity maturation.

Figure 9:
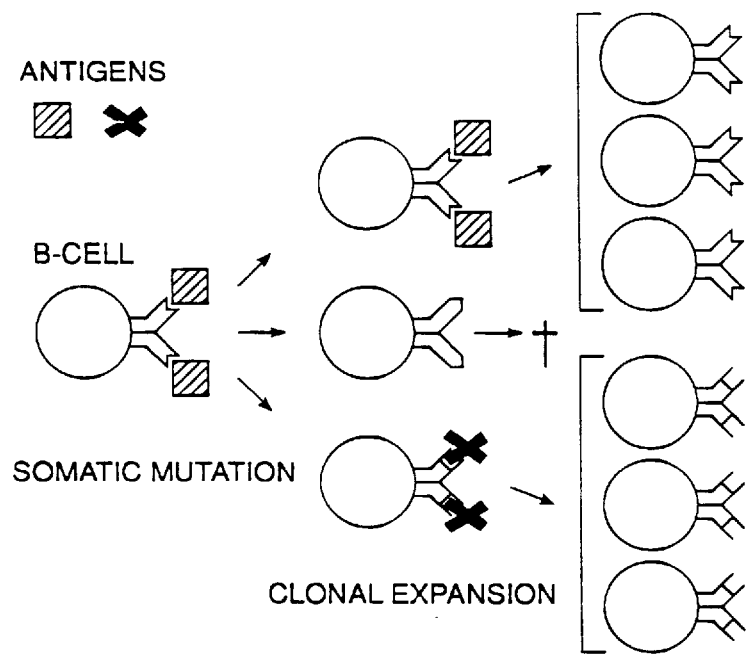
FIG. 9 depicts somatic mutation and clonal expansion of B-cells in response to two different antigens.

In this aspect of the invention, CDR1 and 2 diversity is not necessary for generating a complete antibody response. Rather, diversity at CDR3, created by VJ and VDJ joining provides sufficient minimal affinity to trigger the T-cell dependent maturation to give rise to high affinity antibodies for a large number of different antigens. Thus, methods and transgenic animals are provided for generating a broad antibody repertoire without primary diversity. Such diversity relies on somatic mutation for the generation of antibody diversity. During the process of affinity maturation, somatic mutation gives rise to a large number of clones with lower, rather than higher, affinities for the stimulating antigen. Most of these clones are not selected for and die off. However, if one of these clones has affinity for a new antigen that is also present, this clone expands and undergoes affinity maturation for the new antigen (FIG. 9). In this aspect of the invention, a transgenic non-human animal, such as a mouse, with rearranged human heavy and light chains combine to form an antibody that has a low affinity for a known antigen. If this animal is injected with the known antigen, its B-cells undergo a secondary response leading to the production of high affinity antibodies for that antigen. However, if this mouse is first injected with a mixture of the known antigen and a new antigen, and then subsequently challenged with the new antigen alone, high affinity antibodies against the new antigen are produced by the branching process described above. This approach has two major advantages: first the transgene constructs are easy to generate; and second, the rearranged transgenes are capable of allelicly and isotypically excluding the rearrangement of the endogenous mouse genes, thus making it unnecessary to eliminate those genes by homologous recombination as previously described.

The first step in this embodiment of the invention is the isolation of rearranged heavy and light chain genes from a human hybridoma that expresses an IgM antibody directed against a known antigen. The ideal hybridoma recognizes a readily available antigen that is capable of generating a good mouse T-cell response. There are a number of such human hybridomas in existence, including several that react with promising antigens such as tetanus toxoid, pseudomonas, or gram negative bacteria (reviewed by James and Bourla (1987), *J. Immunol. Methods.,* 100, 5–40). The entire rearranged heavy chain gene is isolated on a single piece of DNA (approximately 20 kb) while the rearranged κ light chain gene, including the 3' enhancer, is isolated on a second DNA fragment (about 20 kb). Each of these fragments are pieced together from clones isolated from a phage λ library made from DNA isolated from the hybridoma. Two constructs are generated, a heavy chain construct and a light chain construct.

Figure 10:
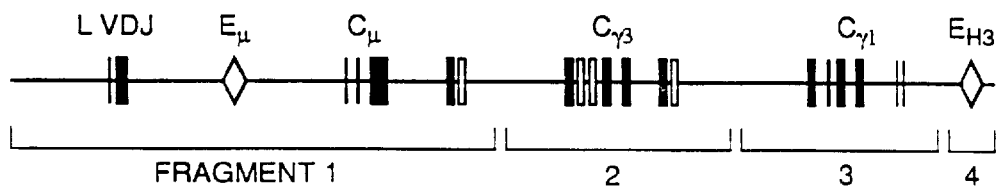
FIG. 10 depicts a transgene construct containing a rearranged IgM gene ligated to a 25 kb fragment that contains human γ3 and γ1 constant regions followed by a 700 bp fragment containing the rat chain 3' enhancer sequence.

The heavy chain construct (FIG. 10) consists of the 20 kb hybridoma fragment, containing the rearranged IgM gene, ligated to a 25 kb fragment that contains the human γ3 and γ1 constant regions followed by a 700 bp fragment containing the rat heavy chain 3' enhancer (Pettersson, et al. (1990), *Nature,* 344, 165–168). The light chain construct consists of the intact 20 kb piece of DNA containing the rearranged κ chain and 3' enhancer. These two constructs are coinjected so that they are integrated at a single site in the mouse genome. Transgenic mice are tested by Northern blot analysis for expression of the transgene mRNA. FACS analysis is then carried-out on tail blood samples to detect cell surface expression of the transgene encoded protein. Mice are then immunized with the antigen recognized by the original hybridoma. ELISA and FACS analysis are carried out on tail blood to detect class switching. Finally, the mice are tested for their ability to respond to a number of different antigens by co-injecting a panel of antigens together with the original antigen. Tail blood are analyzed by ELISA to detect the production of high affinity human IgG antibodies directed against individual antigens.

To use this transgenic mouse to generate human antibodies directed against a given antigen, that antigen preferably is first coinjected together with the antigen associated with the hybridoma from which the genes were isolated. This hybridoma associated antigen is referred to as the co-antigen (sometimes as a second antigen), and the new antigen simply as the antigen (or first antigen). If possible, the second antigen is chemically cross-linked to the first antigen prior to injection. This causes the first antigen to be internalized and presented by the primary transgene presenting B-cells, thus ensuring the existence of a pool of activated helper T-cells that recognize the first antigen. A typical immunization schedule is as follows. Day 1: Mice are injected ip with first antigen mixed with, or cross-linked to, second antigen in complete Freunds adjuvant. Day 14: first antigen (without second antigen) is injected ip in incomplete Freunds adjuvant. Day 35: repeat injection with first antigen in incomplete Freunds. Day 45: Test for antibody response by ELISA on tail blood samples. Day 56: repeat injection of good responders with antigen in incomplete Freunds. Day 59: Fuse spleens of good responders.

In an alternate aspect of this invention, the antigen recognized by the hybridoma from which the Ig genes were isolated, is used as an immunogen. New transgenic hybridomas are then isolated from the immunized animal that express somatically mutated versions of the original antibody. These new antibodies will have a higher affinity for the original antigen. This antibody "sharpening" procedure can also be applied to antibody genes generated by CDR grafting (E.P. Pub. No. 239400, published Sep. 30, 1987) or isolated from bacterial (W. D. Huse et al. (1989) *Science*, 246, 1275) or phage (T. Clackson et al. (1991) *Nature*, 352, 624) expression libraries.

Transgenic Non-Human Animals Containing Rearranged and Unrearranged Immunoglobulin Heavy and/or Light Transgene The previous embodiments described the use of fully rearranged or fully unrearranged heavy and light immunoglobulin transgenes to produce transgenic non-human animals capable of producing a heterologous antibody. In a further aspect of the invention, transgenic animals contain at least one rearranged and at least one unrearranged immunoglobulin transgene are produced by utilizing any of the aforementioned unrearranged and rearranged transgenes in combination to provide heavy and light transgenes in the transgenic animal. In this regard, the unrearranged transgene may comprise a heavy or light genomic or mini-locus transgene construct with the rearranged transgene comprising an appropriate rearranged transgene. For example, if a unrearranged mini-locus light chain transgene is used, the appropriate other transgene is a fully rearranged heavy chain transgene. It is preferred, however, that the rearranged transgene comprise a rearranged immunoglobulin light chain transgene and that the unrearranged transgene comprise an immunoglobulin heavy chain genomic or mini-locus transgene, most preferably an unrearranged heavy chain transgene with associated A and y constant regions.

The combination of rearranged and unrearranged transgene provides an intermediate level of diversity within the primary repertoire B-cells. Thus, although primary diversity at CD1, CD2 and CD3 in the rearranged transgene is fixed in the primary repertoire B-cell, the primary diversity at the CDR1, CDR2 and CDR3 produced by the rearrangement of the unrearranged transgene provides a population of primary repertoire of B-cells having greater potential diversity than the B-cell clone obtained when rearranged heavy and light transgenes are used. Such primary diversity provides broadened secondary diversity when such cells respond to foreign antigen by way of somatic mutation.

Nucleic Acids

The nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98 to 99.5% of the nucleotides. Alternatively, substantial homology exists when the segments will hybridize under selective hybridization conditions, to the complement of the strand. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley-Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

Specific Preferred Embodiments

A preferred embodiment of the invention is an animal containing a single copy of the transgene described in Example 14 (pHC2) bred with an animal containing a single copy of the transgene described in Example 16, and the offspring bred with the JH deleted animal described in Examples 9 and 12. Animals are bred to homozygosity for each of these three traits. Such animals have the following genotype: a single copy (per haploid set of chromosomes) of a human heavy chain unrearranged mini-locus (described in Example 14), a single copy (per haploid set of chromosomes) of a rearranged human κ light chain construct (described in Example 16), and a deletion at each endogenous mouse heavy chain locus that removes all of the functional JH segments (described in Examples 9 and 12). Such animals are bred with mice that are homozygous for the deletion of the JH segments (Examples 9 and 12) to produce offspring that are homozygous for the JH deletion and hemizygous for the human heavy and light chain constructs. The resultant animals are injected with antigens and used for production of human monoclonal antibodies against these antigens.

B cells isolated from such an animal are monospecific with regards to the human heavy and light chains because they contain only a single copy of each gene. Furthermore, they will be monospecific with regards to human or mouse heavy chains because both endogenous mouse heavy chain gene copies are nonfunctional by virtue of the deletion spanning the JH region introduced as described in Example 9 and 12. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and lambda chain genes in a significant fraction of B-cells.

The transgenic mouse of the preferred embodiment will exhibit immunoglobulin production with a significant repertoire, ideally substantially similar to that of a native mouse. Thus, for example, when the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. Of course, the IgG to IgM ratio will be much lower in the immature mouse. In general, greater than about 10%, preferably 40 to 80% of the spleen and lymph node B cells express exclusively human IgG protein.

The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, including, but not limited to: pigeon cytochrome C, chicken lysozyme, pokeweed mitogen, bovine serum albumin, keyhole limpit hemocyanin, influenza hemagglutinin, staphylococcus protein A, sperm whale myoglobin, influenza neuraminidase, and lambda repressor protein. Some of the immunoglobulins will exhibit an affinity for preselected antigens of at least about $10^{-7}M^{-1}$, preferably $10^{-8}M^{-1}$ to $10^{-9}M^{-1}$ or greater.

Although the foregoing describes a preferred embodiment of the transgenic animal of the invention, other embodiments are defined by the disclosure herein and more particularly by the transgenes described in the Examples. Four categories of transgenic animal may be defined:

I. Transgenic animals containing an unrearranged heavy and rearranged light immunoglobulin transgene.

II. Transgenic animals containing an unrearranged heavy and unrearranged light immunoglobulin transgene III. Transgenic animal containing rearranged heavy and an unrearranged light immunoglobulin transgene, and IV. Transgenic animals containing rearranged heavy and rearranged light immunoglobulin transgenes.

Of these categories of transgenic animal, the preferred order of preference is as follows I>II>III>IV.

Within each of these categories of the transgenic animal, a number of possible combinations are preferred. Such preferred embodiments comprise the following:

Category I (a) Example 1 and 2 or 19 and 20 animal bred with Example 7 or 16 animal.
(b) Example 1 or 19 fragment coinjected with Example 7 or 16 fragment.
(c) Example 5 (H, I or J) or 14, 17 or 21 animal bred with Example 7 or 16 animal.
(d) Example 5(H) or 14 construct coinjected with example 7 or 16 construct.
(e) All of the above bred with the animal of Example or 11, 12 or 13. Particularly preferred embodiments are all of the above bred the with animal of Example 9 or 12 or 13.

Category II (a) Example 1, 2, 19 or 20 animal bred with Example 6, 3, 4, 16, 22 or 23 animal.
(b) Fragment in Example 1 or 19 coinjected with fragment in Example 2 or 20.
(c) Example 5 (H, I or J) or 14, 17 or 21 animal bred with Example 6(B, C or D) or 16 animal.
(d) Construct 5(H) or 14 coinjected with construct 6(B) or 16.
(e) Animal of Example 1, 2, 19 or 20 bred with animal of Example 6(B, C or D) or 16.
(f) Animal of Example 3, 4, 22 or 23 bred with animal of Example 5(H, I or J) or 14, 17 or 21.
(g) All of the above bred with animal of Example 9, 10, 11, 12 or 13.

Category III (a) Example 3, 4, 22 or 23 animal bred with Example 8 or 15 animal.
(b) Example 3 or 23 fragment coinjected with Example 8 or 15 fragment.
(C) Example 6(B, C or D) or 16 animal bred with Example 8 or 15 animal.
(d) Example 6(B) or 15 construct coinjected with Example 8 or 15 construct.
(e) All of the above bred with animal of Example 9 to 13.

Category IV (a) Animal of Example 7 or 16, bred with animal of Example 8 or 15.
(b) Construct of Example 7 or 16 coinjected with construct of Example 8 or 15.
(c) All of the above bred with animal of Example 9 to 13.

The following is presented by way of example and is not to be construed as a limitation to the scope of the claims.

METHODS AND MATERIALS

Transgenic mice are derived according to Hogan, et al., "Manipulating the Mouse Embryo: A Laboratory Manual", Cold Spring Harbor Laboratory.

Embryonic stem cells are manipulated according to published procedures (Teratocarcinomas and embryonic stem cells: a practical approach, E. J. Robertson, ed., IRL Press, Washington, D.C., 1987; Zjilstra, et al. (1989), *Nature*, 4, 435–438; and Schwartzberg, P., et al. (1989), *Science*, 246, 799–803).

DNA cloning procedures are carried out according to J. Sambrook, et al. in Molecular Cloning: A Laboratory Manual, 2d ed., 1989, Cold Spring Harbor Laboratory Press, Cold Spring Harbor, N.Y.

Oligonucleotides are synthesized on an Applied Bio Systems oligonucleotide synthesizer according to specifications provided by the manufacturer.

Hybridoma cells and antibodies are manipulated according to "Antibodies: A Laboratory Manual", Ed Harlow and David Lane, Cold Spring Harbor Laboratory (1988).

EXAMPLE 1

Genomic Heavy Chain Human Ig Transgene

This Example describes the cloning and microinjection of a human genomic heavy chain immunoglobulin transgene which is microinjected into a murine zygote.

Nuclei are isolated from fresh human placental tissue as described by Marzluff, W. F., et al. (1985), "Transcription and Translation: A Practical Approach", B. D. Hammes and S. J. Higgins, eds., pp. 89–129, IRL Press, Oxford). The isolated nuclei (or PBS washed human spermatocytes) are embedded in a low melting point agarose matrix and lysed with EDTA and proteinase κ to expose high molecular weight DNA, which is then digested in the agarose with the restriction enzyme NotI as described by M. Finney in Current Protocols in Molecular Biology (F. Ausubel, et al., eds. John Wiley & Sons, Supp. 4, 1988, Section 2.5.1).

The NotI digested DNA is then fractionated by pulsed field gel electrophoresis as described by Anand, R., et al. (1989), *Nucl. Acids Res.*, 17, 3425–3433. Fractions enriched for the NotI fragment are assayed by Southern hybridization to detect one or more of the sequences encoded by this fragment. Such sequences include the heavy chain D segments, J segments, $\mu$ and $\gamma 1$ constant regions together with representatives of all 6 VH families (although this fragment is identified as 670 kb fragment from HeLa cells by Berman, et al. (1988), supra., we have found it to be as 830 kb fragment from human placental an sperm DNA). Those fractions containing this NotI fragment (see FIG. 4) are pooled and cloned into the NotI site of the vector pYACNN in Yeast cells. Plasmid pYACNN is prepared by digestion of pYAC-4 Neo (Cook, H., et al. (1988), *Nucleic Acids Res.*, 16, 11817) with EcoRI and ligation in the presence of the oligonucleotide 5'-AAT TGC GGC CGC-3' SEQ. ID NO:1).

YAC clones containing the heavy chain NotI fragment are isolated as described by Brownstein, et al. (1989), *Science*, 244, 1348–1351, and Green, E., et al. (1990), *Proc. Natl. Acad. Sci. USA*, 87, 1213–1217. The cloned NotI insert is isolated from high molecular weight yeast DNA by pulse field gel electrophoresis as described by M. Finney, opcit. The DNA is condensed by the addition of 1 mM spermine and microinjected directly into the nucleus of single cell embryos previously described.

EXAMPLE 2

Discontinuous Genomic Heavy Chain Ig Transgene

A 110 kb SpeI fragment of human genomic DNA containing VH6, D segments, J segments, the $\mu$ constant region and part of the $\gamma$ constant region (see FIG. 4) is isolated by YAC cloning as described in Example 1.

A 570 kb NotI fragment upstream of the 670–830 kb NotI fragment described above containing multiple copies of VI through V5 is isolated as described. (Berman, et al. (1988), supra detected two 570 kb NotI fragments. Each of those contain multiple V segments.)

The two fragments are coinjected into the nucleus of a mouse single cell embryo as described in Example 1.

Coinjection of two different DNA fragments will usually result in the integration of both fragments at the same insertion site within the chromosome. Therefore, approximately 50% of the resulting transgenic animals that contain at least one copy of each of the two fragments will have the V segment fragment inserted upstream of the constant region containing fragment. Of these animals, 50% will carry out V to DJ joining by DNA inversion and 50% by deletion, depending on the orientation of the 570 kb NotI fragment relative to the position of the 110 kb SpeI fragment. DNA is isolated from resultant transgenic animals and those animals found to be containing both transgenes by Southern blot hybridization (specifically, those animals containing both multiple human V segments and human constant region genes) are tested for their ability to express human immunoglobulin molecules.

EXAMPLE 3

Figure 11:
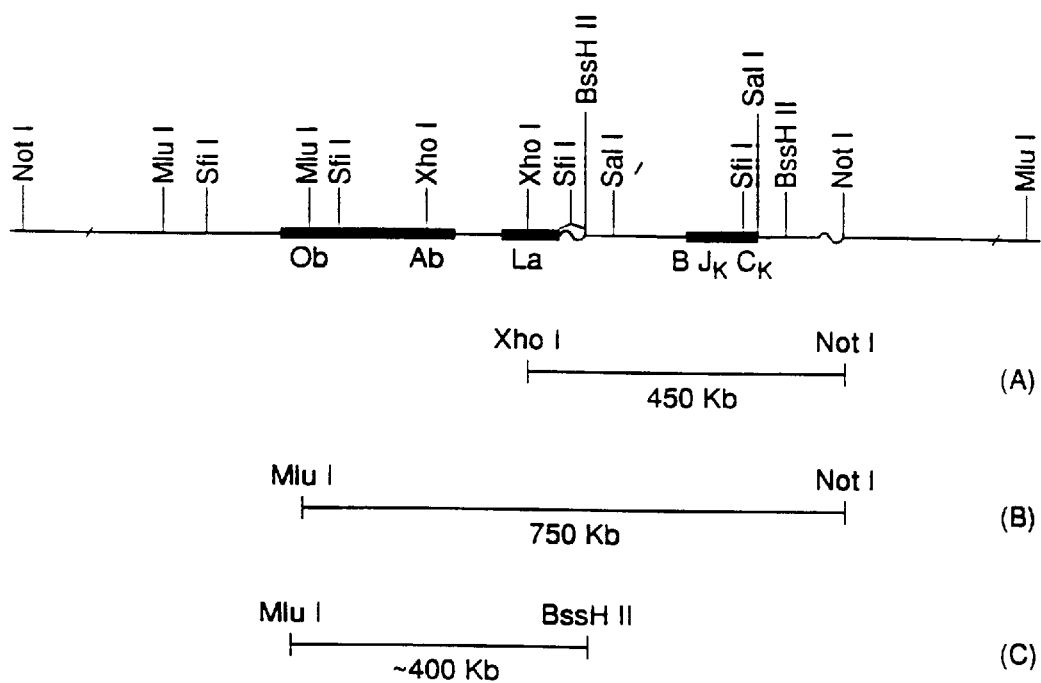
FIG. 11 is a restriction map of the human κ chain locus depicting the fragments to be used to form a light chain transgene by way of in vivo homologous recombination.
Figure 12:
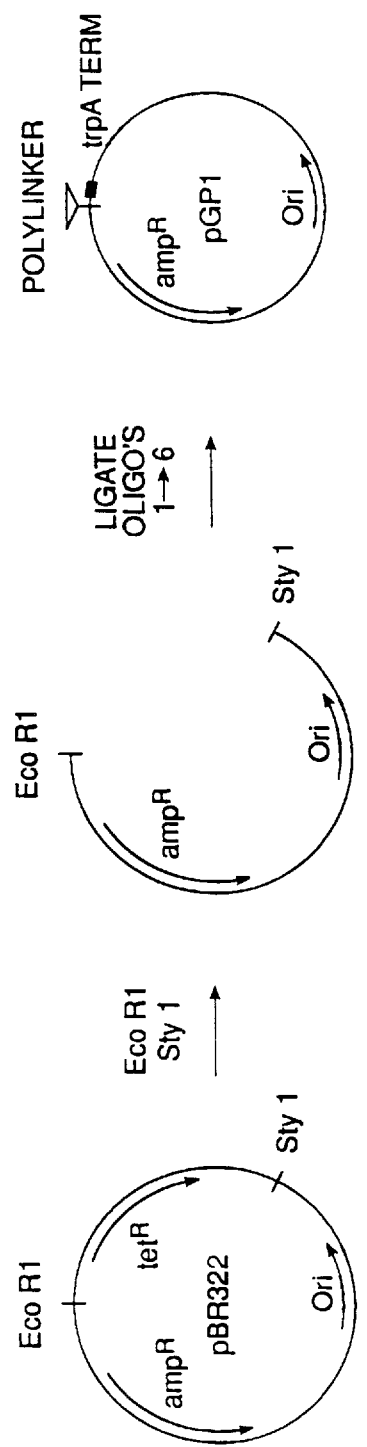
FIG. 12 depicts the construction of pGP1.

Genomic κ Light Chain Human Ig Transgene Formed by In Vivo Homologous Recombination A map of the human κ light chain has been described in Lorenz, W., et al. (1987), *Nucl. Acids Res.*, 15, 9667–9677 and is depicted in FIG. 11.

A 450 kb XhoI to NotI fragment that includes all of Ck, the 3' enhancer, all J segments, and at least five different V segments (a) is isolated and microinjected into the nucleus of single cell embryos as described in Example 1.

EXAMPLE 4

Genomic κ Light Chain Human Ig Transgene Formed by In Vivo Homologous Recombination A 750 kb MluI to NotI fragment that includes all of the above plus at least 20 more V segments (b) is isolated as described in Example 1 (see FIG. 11) and digested with BssHII to produce a fragment of about 400 kb (c).

The 450 kb XhoI to NotI fragment (a) plus the approximately 400 kb MluI to BssHII fragment (c) have sequence overlap defined by the BssHII and XhoI restriction sites shown in FIG. 11. Homologous recombination of these two fragments upon microinjection of a mouse zygote results in a transgene containing at least an additional 15–20 V segments over that found in the 450 kb XhoI/NotI fragment (Example 3).

EXAMPLE 5

Figure 13:
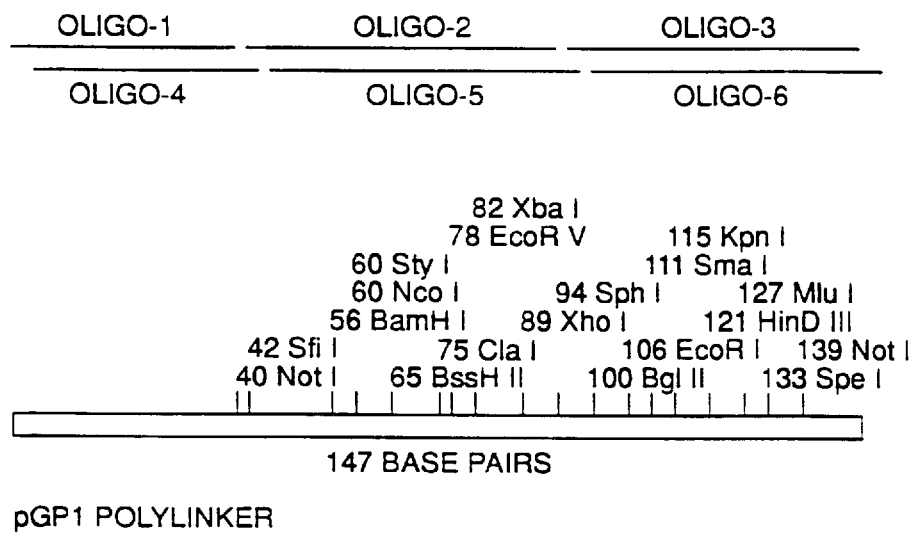
FIG. 13 depicts the construction of the polylinker contained in pGP1.

Construction of Heavy Chain Mini-Locus
A. Construction of pGP1 and pGP2 pBR322 is digested with EcoRI and StyI and ligated with the following oligonucleotides to generate pGP1 which contains a 147 base pair insert containing the restriction sites shown in FIG. 13. The general overlapping of these oligos is also shown in FIG. 13.

The oligonucleotides are:

oligo-1 5'-CTT GAG CCC GCC TAA TGA GCG GGC TTT
        TTT TTG CAT ACT GCG GCC -3' (SEQ. ID NO: 2)

oligo-2 5'-GCA ATG GCC TGG ATC CAT GGC GCG CTA
        GCA TCG ATA TCT AGA GCT CGA GCA -3'
                                    (SEQ. ID NO: 3)

oligo-3 5'-TGC AGA TCT GAA TTC CCG GGT ACC AAG
        CTT ACG CGT ACT AGT GCG GCC GCT -3'
                                    (SEQ. ID NO: 4)

oligo-4 5'-AAT TAG CGG CCG CAC TAG TAC GCG TAA
        GCT TGG TAC CCG GGA ATT -3' (SEQ. ID NO: 5)

oligo-5 5'-CAG ATC TGC ATG CTC GAG CTC TAG ATA
        TCG ATG CTA GCG CGC CAT GGA TCC -3'
                                    (SEQ. ID NO: 6)

oligo-6 5'-AGG CCA TTG CGG CCG CAG TAT GCA AAA
        AAA AGC CCG CTC ATT AGG CGG GCT -3'
                                    (SEQ. ID NO: 7)

This plasmid contains a large polylinker flanked by rare cutting NotI sites for building large inserts that can be isolated from vector sequences for microinjection. The plasmid is based on pBR322 which is relatively low copy compared to the pUC based plasmids (pGP1 retains the pBR322 copy number control region near the origin of replication). Low copy number reduces the potential toxicity of insert sequences. In addition, pGP1 contains a strong transcription terminator sequence derived from trpA (Christie, G. E., et al. (1981), *Proc. Natl. Acad. Sci. USA*) inserted between the ampicillin resistance gene and the polylinker. This further reduces the toxicity associated with certain inserts by preventing readthrough transcription coming from the ampicillin promoters.

Plasmid pGP2 is derived from pGP1 to introduce an additional restriction site (SfiI) in the polylinker. pGP1 is digested with MluI and SpeI to cut the recognition sequences in the polylinker portion of the plasmid.

The following adapter oligonucleotides are ligated to the thus digested pGP1 to form pGP2.

```
5'CGC GTG GCC GCA ATG GCC A 3' (SEQ. ID NO: 8)

5'CTA GTG GCC ATT GCG GCC A 3' (SEQ. ID NO: 9)
``` pGP2 is identical to pGP1 except that it contains an additional Sfi I site located between the MluI and SpeI sites. This allows inserts to be completely excised with SfiI as well as with NotI.

B. Construction of pRE3 (rat enhancer 3')

An enhancer sequence located downstream of the rat constant region is included in the heavy chain constructs.

The heavy chain region 3' enhancer described by S. Pettersson, et al. (1990), *Nature*, 344, 165–168) is isolated and cloned. The rat IGH 3' enhancer sequence is PCR amplified by using the following oligonucleotides:

```
5' CAG GAT CCA GAT ATC AGT ACC TGA AAC AGG GCT TGC 3' (SEQ. ID NO: 10)

5' GAG CAT GCA CAG GAC CTG GAG CAC ACA CAG CCT TCC 3' (SEQ. ID NO: 11)
```

The thus formed double stranded DNA encoding the 3' enhancer is cut with BamHI and SphI and clone into BamHI/SphI cut pGP2 to yield pRE3 (rat enhancer 3').

C. Cloning of Human J-$\mu$ Region

A substantial portion of this region is cloned by combining two or more fragments isolated from phage lambda inserts. See FIG. 14.

A 6.3 kb BamHI/HindIII fragment that includes all human J segments (Matsuda, et al. (1988), *EMBO J.*, 7, 1047–1051; Ravetech, et al. (1981), *Cell*, 27, 583–591) is isolated from human genomic DNA library using the oligonucleotide GGA CTG TGT CCC TGT GTG ATG CTT TTG ATG TCT GGG GCC AAG (SEQ. ID NO:12).

An adjacent 10 kb HindIII/BamII fragment that contains enhancer, switch and constant region coding exons (Yasui, et al. (1989), *Eur. J. Immunol.*, 19, 1399–1403) is similarly isolated using the oligonucleotide: CAC CAA GTT GAC CTG CCT GGT CAC AGA CCT GAC CAC CTA TGA (SEQ. ID NO:13).

An adjacent 3' 1.5 kb BamHI fragment is similarly isolated using clone pMUM insert as probe (pMUM is 4 kb EcoRI/HindIII fragment isolated from human genomic DNA library with oligonucleotide:

```
CCT GTG GAC CAC CGC CTC CAC CTT CAT
CGT CCT CTT CCT CCT (SEQ. ID NO: 14)
``` mu membrane exon 1) and cloned into pUC19.

pGP1 is digested with BamHI and BglII followed by treatment with calf intestinal alkaline phosphatase.

Figure 14:
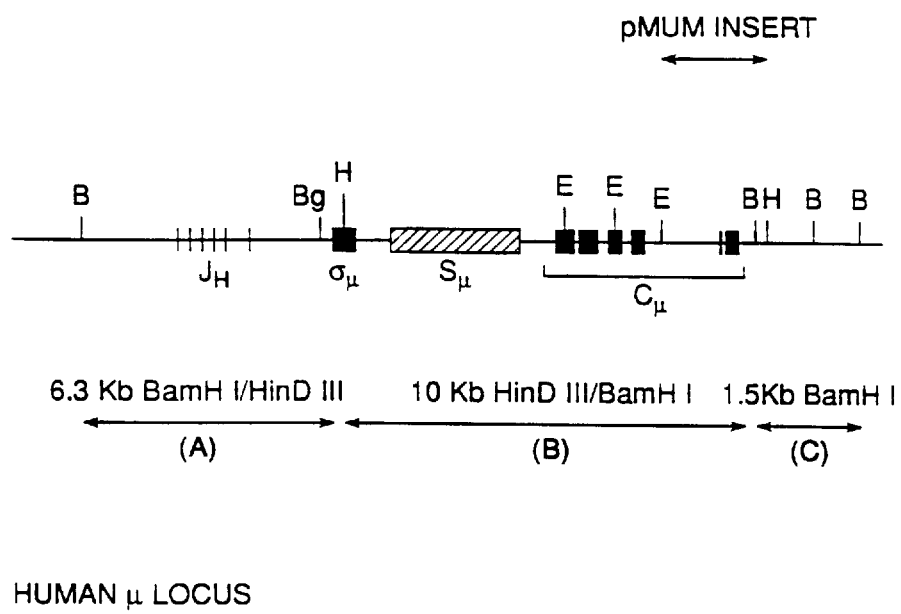
FIG. 14 depicts the fragments used to construct a human heavy chain transgene of the invention.

Fragments (a) and (b) from FIG. 14 are cloned in the digested pGP1. A clone is then isolated which is oriented such that 5' BamHI site is destroyed by BamHI/Bgl fusion. It is identified as pMU (see FIG. 15). pMU is digested with BamHI and fragment (c) from FIG. 14 is inserted. The orientation is checked with HindIII digest. The resultant plasmid pHIG1 (FIG. 15) contains an 18 kb insert encoding J and C$\mu$ segments.

D. Cloning of C$\mu$ Region pGP1 is digested with BamHI and HindIII is followed by treatment with calf intestinal alkaline phosphatase (FIG. 14). The so treated fragment (b) of FIG. 14 and fragment (c) of FIG. 14 are cloned into the BamHI/HindIII cut pGP1. Proper orientation of fragment (c) is checked by HindIII digestion to form pCON1 containing a 12 kb insert encoding the C$\mu$ region.

Whereas pHIG1 contains J segments, switch and $\mu$ sequences in its 18 kb insert with an SfiI 3' site and a SpeI 5' site in a polylinker flanked by NotI sites, will be used for rearranged VDJ segments. pCON1 is identical except that it lacks the J region and contains only a 12 kb insert. The use of pCON1 in the construction of fragment containing rearranged VDJ segments will be described hereinafter.

E. Cloning of $\gamma$-1 Constant Region (pREG2)

Figure 16:
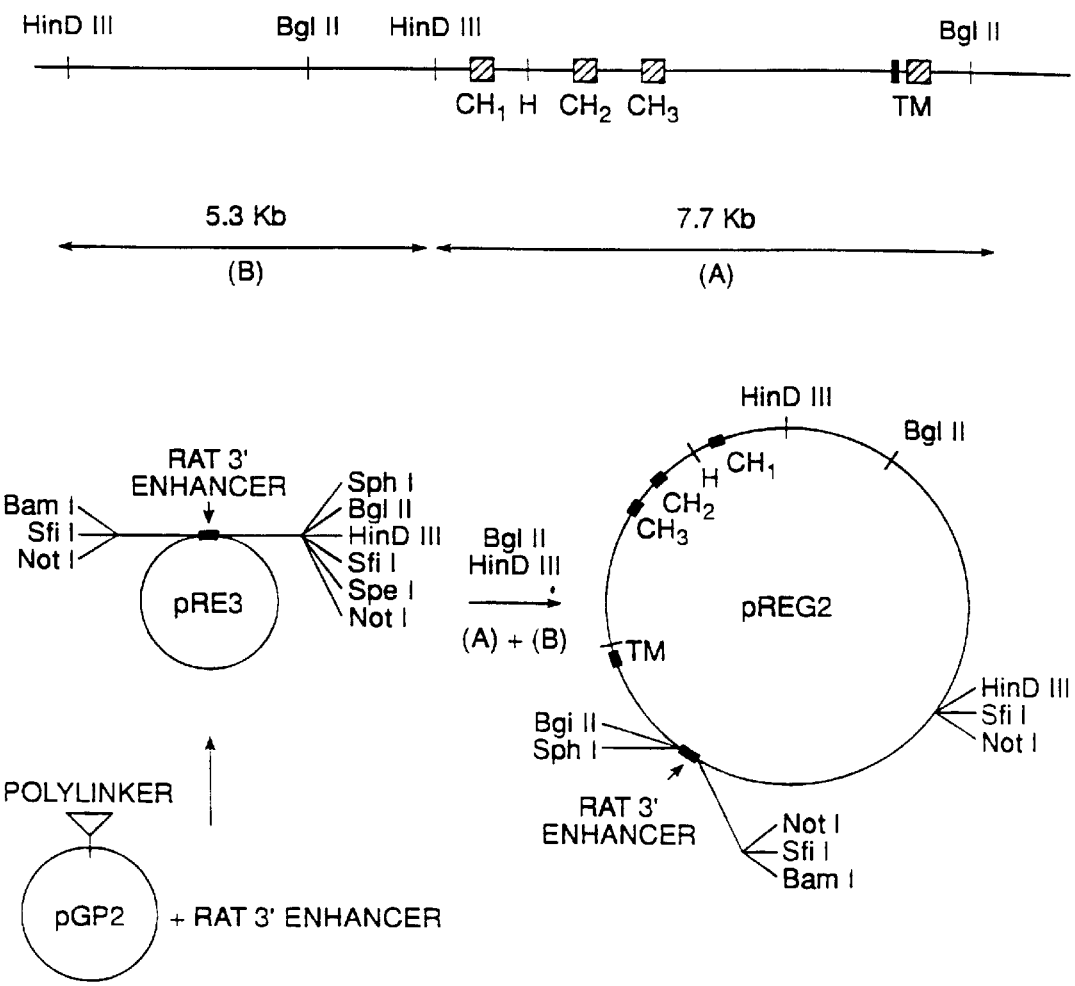
FIG. 16 depicts the human Cγ1 fragments which are inserted into pRE3 (rat enhancer 3') to form pREG2.

The cloning of the human $\gamma$-1 region is depicted in FIG. 16.

Yamamura, et al. (1986), *Proc. Natl. Acad. Sci. USA*, 83, 2152–2156 reported the expression of membrane bound human $\gamma$-1 from a transgene construct that had been partially deleted on integration. Their results indicate that the 3' BamHI site delineates a sequence that includes the transmembrane rearranged and switched copy of the gamma gene with a V-C intron of less than 5 kb. Therefore, in the unrearranged, unswitched gene, the entire switch region is included in a sequence beginning less than 5 kb from the 5' end of the first $\gamma$-1 constant exon. Therefore it is included in the 5' 5.3 kb HindIII fragment (Ellison, J. W., et al. (1982), *Nucleic Acids Res.*, 10, 4071–4079). Takahashi, et al. (1982), *Cell*, 29, 671–679 also reports that this fragment contains the switch sequence, and this fragment together with the 7.7 kb HindIII to BamHI fragment must include all of the sequences we need for the transgene construct.

Phage clones containing the $\gamma$-1 region are identified and isolated using the following oligonucleotide which is specific for the third exon of $\gamma$-I (CH3).

```
5' TGA GCC ACG AAG ACC CTG AGG
   TCA AGT TCA ACT GGT ACG TGG 3'
   (SEQ. ID NO: 15)
```

A 7.7 kb HindIII to BglII fragment (fragment (a) in FIG. 16) is cloned into HindIII/BglII cut pRE3 to form pREG1. The upstream 5.3 kb HindIII fragment (fragment (b) in FIG. 16) is cloned into HindIII digested pREG1 to form pREG2. Correct orientation is confirmed by BamHI/SpeI digestion.

F. Combining C$\gamma$ and C$\mu$

Figure 15:
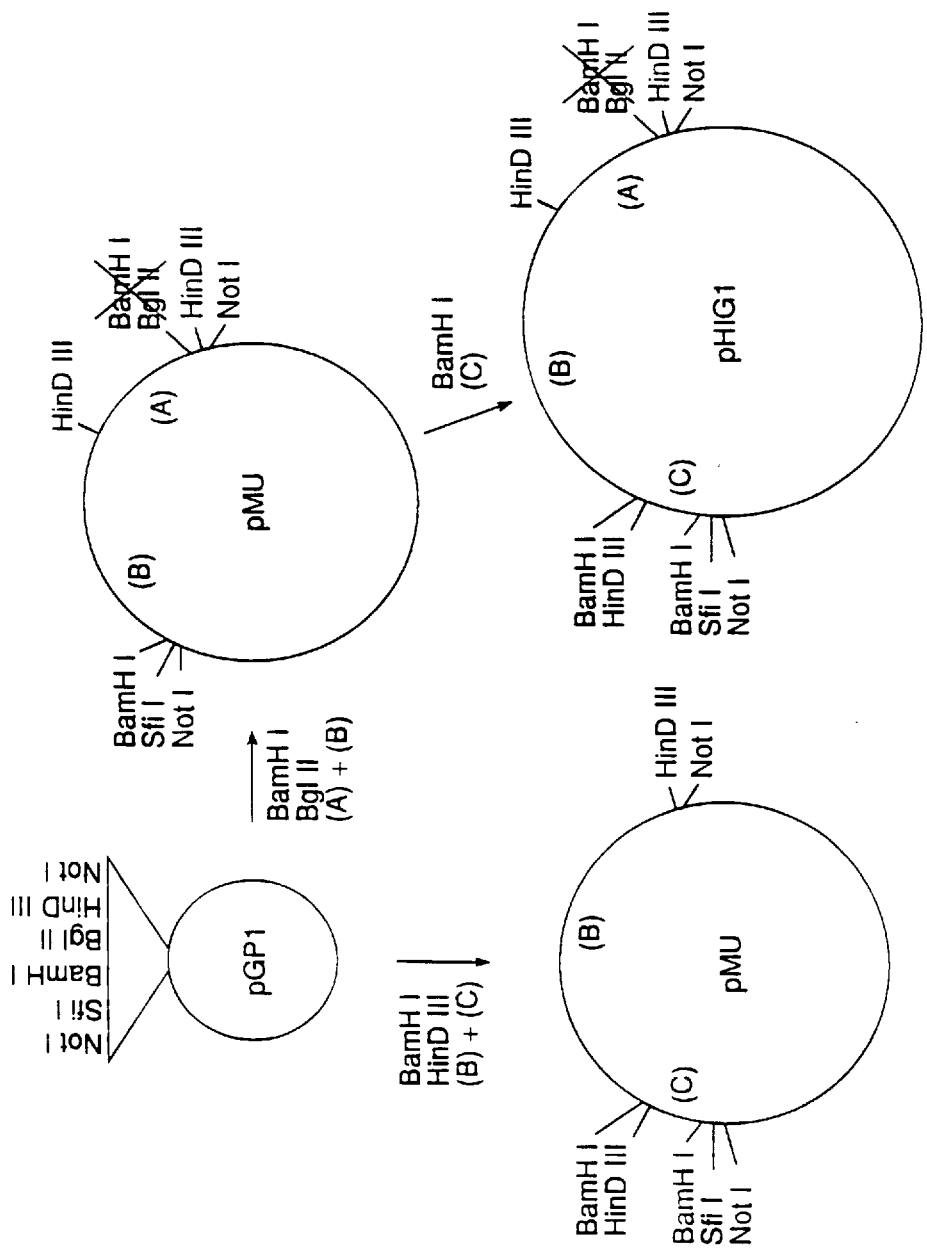
FIG. 15 depicts the construction of pHIG1 and pCON1.
Figure 17:
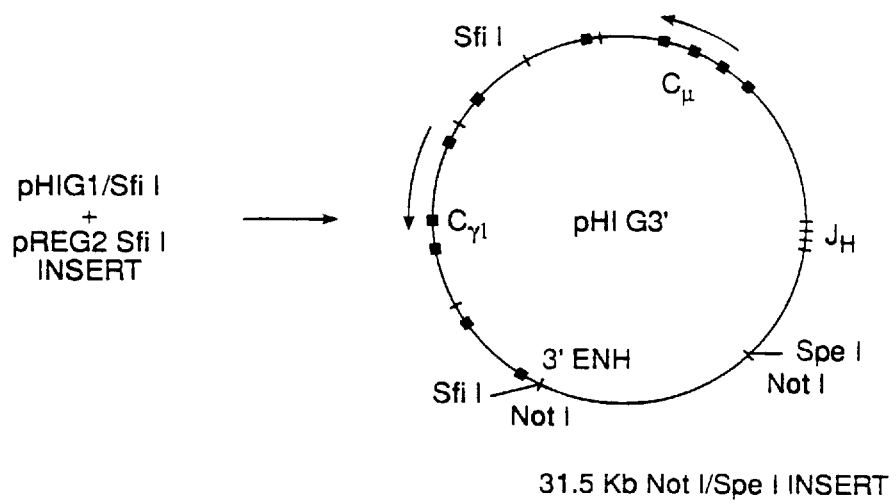
FIG. 17 depicts the construction of pHIG3' and PCON.
Figure 17:
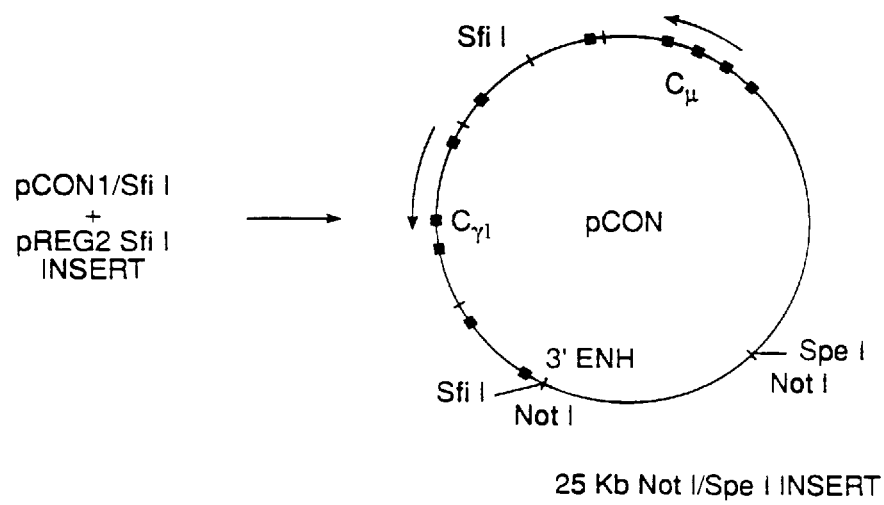

The previously described plasmid pHIG1 contains human J segments and the C$\mu$ constant region exons. To provide a transgene containing the C$\mu$ constant region gene segments, pHIG1 was digested with SfiI (FIG. 15). The plasmid pREG2 was also digested with SfiI to produce a 13.5 kb insert containing human C$\gamma$ exons and the rat 3' enhancer sequence. These sequences were combined to produce the plasmid pHIG3' (FIG. 17) containing the human J segments, the human C$\mu$ constant region, the human C$\gamma$1 constant region and the rat 3' enhancer contained on a 31.5 kb insert.

A second plasmid encoding human Cμ and human Cγ1 without J segments is constructed by digesting pCON1 with SfiI and combining that with the SfiI fragment containing the human Cγ region and the rat 3' enhancer by digesting pREG2 with SfiI. The resultant plasmid, pCON (FIG. 17) contains a 26 kb NotI/SpeI insert containing human Cμ, human γ1 and the rat 3' enhancer sequence.

G. Cloning of D Segment

Figure 18:
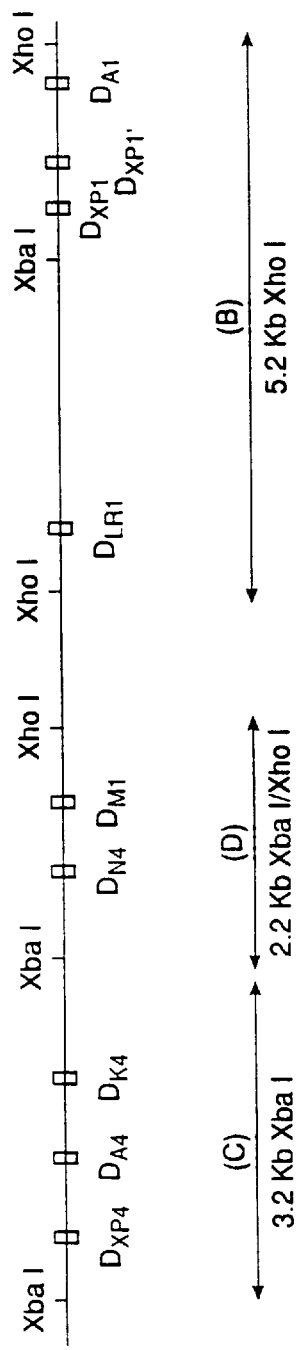
FIG. 18 depicts the fragment containing human D region segments used in construction of the transgenes of the invention.
Figure 19:
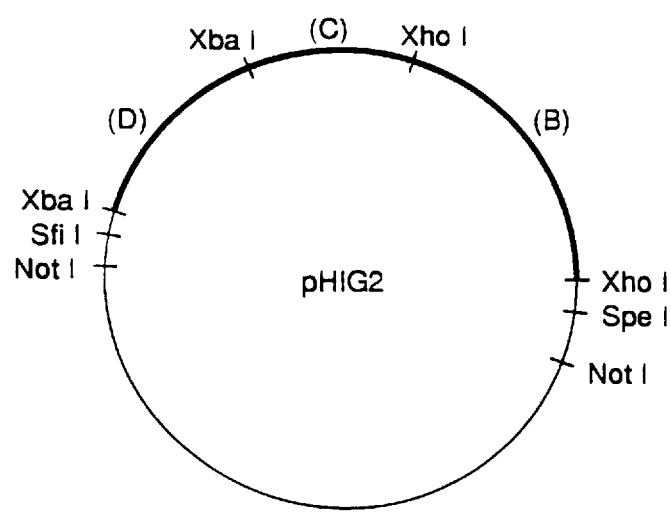
FIG. 19 depicts the construction of pHIG2 (D segment containing plasmid).

The strategy for cloning the human D segments is depicted in FIG. 18. Phage clones from the human genomic library containing D segments are identified and isolated using probes specific for diversity region sequences (Y. Ichihara, et al. (1988), *EMBO J.*, 7, 4141–4150). The following oligonucleotides are used:

```
DXP1: 5'-TGG TAT TAC TAT GGT TCG GGG AGT TAT TAT AAC CAC AGT GTC-3' (SEQ. ID NO: 16)

DXP4: 5'-GCC TGA AAT GGA GCC TCA GGG CAC AGT GGG CAC GGA CAC TGT-3' (SEQ. ID NO: 17)

DN4:  5'-GCA GGG AGG ACA TGT TTA GGA TCT GAG GCC GCA CCT GAC ACC-3' (SEQ. ID NO: 18)
```

A 5.2 kb XhoI fragment (fragment (b) in FIG. 18) containing DLR1, DXP1, DXP'1, and DA1 is isolated from a phage clone identified with oligo DXP1.

A 3.2 kb XbaI fragment (fragment (c) in FIG. 18) containing DXP4, DA4 and DK4 is isolated from a phage clone identified with oligo DXP4.

Fragments (b), (c) and (d) from FIG. 18 are combined and cloned into the XbaI/XhoI site of pGP1 to form pHIG2 which contains a 10.6 kb insert.

This cloning is performed sequentially. First, the 5.2 kb fragment (b) in FIG. 18 and the 2.2 kb fragment (d) of FIG. 18 are treated with calf intestinal alkaline phosphatase and cloned into pGP1 digested with XhoI and XbaI. The resultant clones are screened with the 5.2 and 2.2 kb insert. Half of those clones testing positive with the 5.2 and 2.2 kb inserts have the 5.2 kb insert in the proper orientation as determined by BamHI digestion. The 3.2 kb XbaI fragment from FIG. 18 is then cloned into this intermediate plasmid containing fragments (b) and (d) to form pHIG2 (FIG. 9). This plasmid contains diversity segments cloned into the polylinker with a unique 5' SfiI site and unique 3' SpeI site. The entire polylinker is flanked by NotI sites.

H. Construction of Heavy Chain Minilocus

The following describes the construction of a human heavy chain mini-locus which contain one or more V segments.

An unrearranged V segment corresponding to that identified as the V segment contained in the hybridoma of Newkirk, et al. (1988), *J. Clin. Invest.*, 81, 1511–1518, is isolated using the following oligonucleotide:

```
5'-GAT CCT GGT TTA GTT AAA GAG GAT TTT
   ATT CAC CCC TGT GTC-3' (SEQ. ID NO: 19)
```

A restriction map of the unrearranged V segment is determined to identify unique restriction sites which provide upon digestion a DNA fragment having a length approximately 2 kb containing the unrearranged V segment together with 5' and 3' flanking sequences. The 5' prime sequences will include promoter and other regulatory sequences whereas the 3' flanking sequence provides recombination sequences necessary for V-DJ joining. This approximately 3.0 kb V segment insert is cloned into the polylinker of pGB2 to form pVH1.

pVH1 is digested with SfiI and the resultant fragment is cloned into the SfiI site of pHIG2 to form a pHIG5'. Since pHIG2 contains D segments only, the resultant pHIG5' plasmid contains a single V segment together with D segments. The size of the insert contained in pHIG5 is 10.6 kb plus the size of the V segment insert.

The insert from pHIG5 is excised by digestion with NotI and SpeI and isolated. pHIG3' which contains J, Cμ and cγ1 segments is digested with SpeI and NotI and the 3' kb fragment containing such sequences and the rat 3' enhancer sequence is isolated. These two fragments are combined and ligated into NotI digested pGP1 to produce pHIG which contains insert encoding a V segment, nine D segments, six functional J segments, Cμ, Cγ and the rat 3' enhancer. The size of this insert is approximately 43 kb plus the size of the V segment insert.

I. Construction of Heavy Chain Minilocus by Homologous Recombination

As indicated in the previous section, the insert of pHIG is approximately 43 to 45 kb when a single V segment is employed. This insert size is at or near the limit of that which may be readily cloned into plasmid vectors. In order to provide for the use of a greater number of V segments, the following describes in vivo homologous recombination of overlapping DNA fragments which upon homologous recombination within a zygote or ES cell form a transgene containing the rat 3' enhancer sequence, the human Cμ, the human Cγ1, human J segments, human D segments and a multiplicity of human V segments.

A 6.3 kb BamHI/HindIII fragment containing human J segments (see fragment (a) in FIG. 14) is cloned into MluI/SpeI digested pHIG5' using the following adapters:

```
5' GAT CCA AGC AGT 3' (SEQ. ID NO: 20)

5' CTA GAC TGC TTG 3' (SEQ. ID NO: 21)

5' CGC GTC GAA CTA 3' (SEQ. ID NO: 22)

5' AGC TTA GTT CGA 3' (SEQ. ID NO: 23)
```

The resultant is plasmid designated pHIG5'O (overlap). The insert contained in this plasmid contains human V, D and J segments. When the single V segment from pVH1 is used, the size of this insert is approximately 17 kb plus 2 kb. This insert is isolated and combined with the insert from pHIG3' which contains the human J, Cμ, γ1 and rat 3' enhancer sequences. Both inserts contain human J segments which provide for approximately 6.3 kb of overlap between the two DNA fragments. When coinjected into the mouse zygote, in vivo homologous recombination occurs generating a transgene equivalent to the insert contained in pHIG.

This approach provides for the addition of a multiplicity of V segments into the transgene formed in vivo. For example, instead of incorporating a single V segment into pHIG5', a multiplicity of V segments contained on (1) isolated genomic DNA, (2) ligated DNA derived from genomic DNA, or (3) DNA encoding a synthetic V segment repertoire is cloned into pHIG2 at the SfiI site to generate pHIG5' $V_N$. The J segments fragment (a) of FIG. 14 is then cloned into pHIG5' $V_N$ and the insert isolated. This insert now contains a multiplicity of V segments and J segments which overlap with the J segments contained on the insert isolated from pHIG3'. When cointroduced into the nucleus of a mouse zygote, homologous recombination occurs to generate in vivo the transgene encoding multiple V segments and multiple J segments, multiple D segments, the $C\mu$ region, the $C\gamma1$ region (all from human) and the rat 3' enhancer sequence.

J. Construction of Heavy Chain Mini-Locus by Coinjection of Synthetic VH Region Fragment Together with Heavy Chain DJC Construct Synthetic $V_H$ region fragments are generated and isolated as previously described. These fragments are coinjected with the purified NotI insert of plasmid pHIG (or a version of pHIG that does not contain any V segments). The coinjected DNA fragments are inserted into a single site in the chromosome. Some of the resulting transgenic animals will contain transgene inserts that have synthetic V regions located adjacent and upstream of the sequences in the pHIG construct. These animals will have a larger human heavy chain primary repertoire than the animals described in Example 5(H).

EXAMPLE 6

Construction of Light Chain Minilocus

A. Construction of $pE\mu1$

Figure 21:
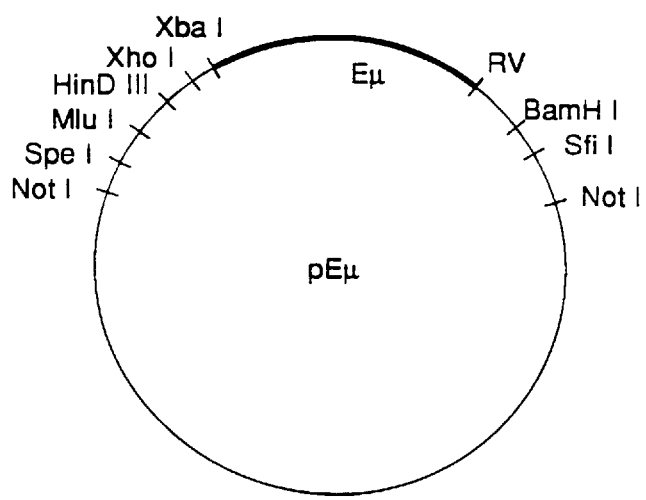
FIG. 21 depicts the structure of pEμ.

The construction of $pE\mu1$ is depicted in FIG. 21. The mouse heavy chain enhancer is isolated on the XbaI to EcoRI 678 bp fragment (J. Banerji, et al. (1983), *Cell*, 33, 729–740) from phage clones using oligo:

```
5' GAA TGG GAG TGA GGC TCT CTC ATA CCC
   TAT TCA GAA CTG ACT 3' (SEQ. ID NO: 24)
```

This $E\mu$ fragment is cloned into EcoRV/XbaI digested pGP1 by blunt end filling in EcoRI site. The resultant plasmid is designated pEmu1.

B. Construction Of κ Light chain Minilocus

The κ construct contains at least one human $V_\kappa$ segment, all five human $J_\kappa$ segments, the human $J\text{-}C_\kappa$ enhancer, human κ constant region exon, and, ideally, the human 3' κ enhancer (K. Meyer, et al. (1989), *EMBO J.*, 8, 1959–1964). The κ enhancer in mouse is 9 kb downstream from $C_\kappa$. However, it is as yet unidentified in the human. In addition, the construct contains a copy of the mouse heavy chain $J\text{-}C\mu$ enhancers.

Figure 20:
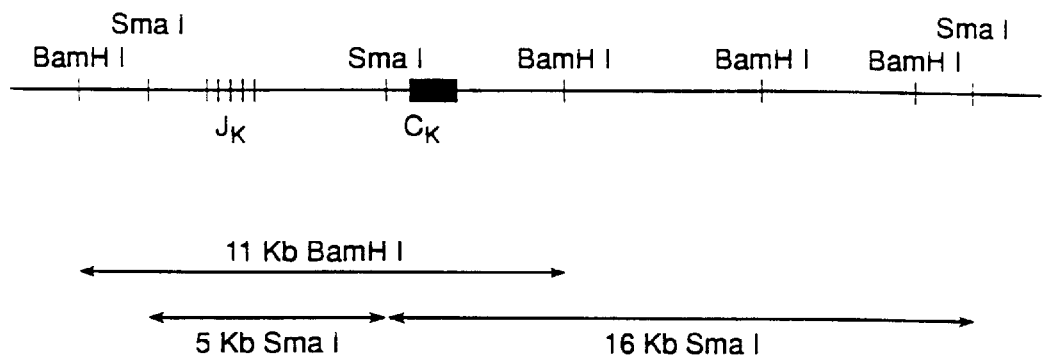
FIG. 20 depicts the fragments covering the human Jκ and human Cκ gene segments used in constructing a transgene of the invention.

The minilocus is constructed from four component fragments:

(a) A 16 kb SmaI fragment that contains the human $C_\kappa$ exon and the 3' human enhancer by analogy with the mouse locus (fragment (a) in FIG. 20);

(b) A 5' adjacent 5 kb SmaI fragment, which contains all five J segments (fragment (b) in FIG. 20);

(c) The mouse heavy chain intronic enhancer isolated from $pE\mu1$ (this sequence is included to induce expression of the light chain construct as early as possible in B-cell development. Because the heavy chain genes are transcribed earlier than the light chain genes, this heavy chain enhancer is presumably active at an earlier stage than the intronic κ enhancer); and (d) A fragment containing one or more V segments.

The preparation of this construct is as follows. Human placental DNA is digested with SmaI and fractionated on agarose gel by electrophoresis. Similarly, human placental DNA is digested with BamHI and fractionated by electrophoresis. The 16 kb fraction is isolated from the SmaI digested gel and the 11 kb region is similarly isolated from the gel containing DNA digested with BamHI.

The 16 kb SmaI fraction is cloned into Lambda FIX II (Stratagene, La Jolla, Calif.) which has been digested with XhoI, treated with klenow fragment DNA polymerase to fill in the XhoI restriction digest product. Ligation of the 16 kb SmaI fraction destroys the SmaI sites and lases XhoI sites in tact.

The 11 kb BamHI fraction is cloned into λ EMBL3 (Strategene, La Jolla, Calif.) which is digested with BamHI prior to cloning.

Clones from each library were probed with the Cκ specific oligo:

```
5' GAA CTG TGG CTG CAC CAT CTG TCT
   TCA TCT TCC CGC CAT CTG 3' (SEQ. ID NO: 25)
```

Figure 22:
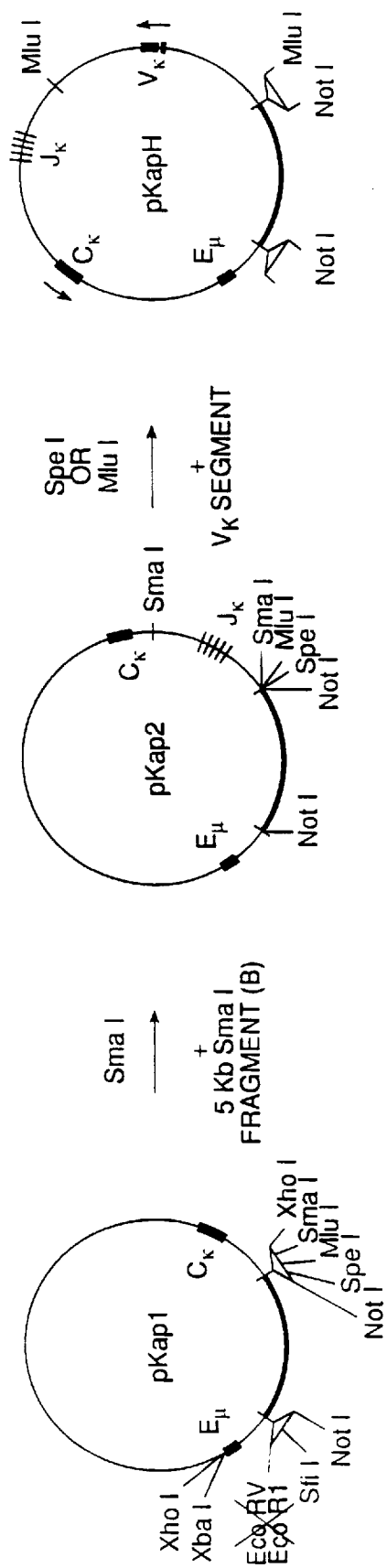
FIG. 22 depicts the construction of pKapH.
Figure 23A:
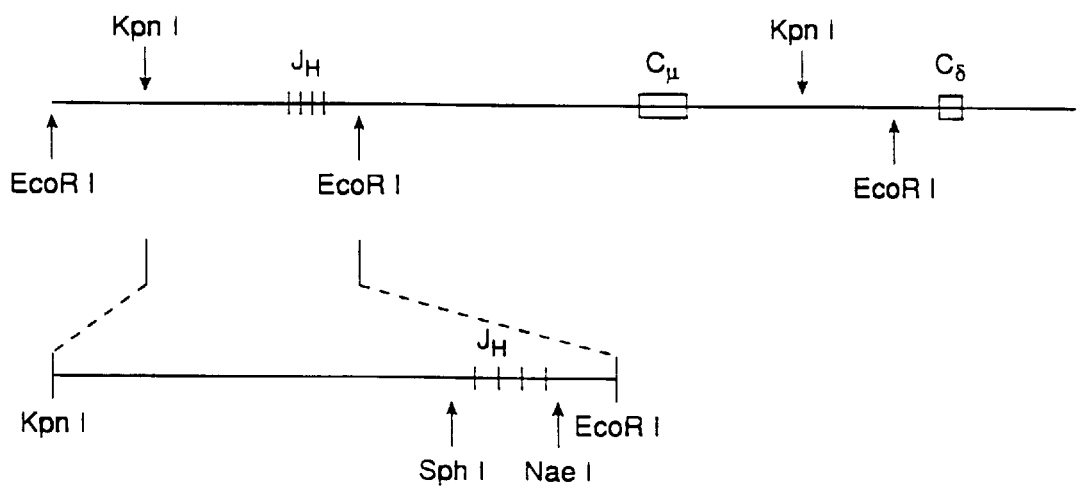
FIGS. 23A through 23D depict the construction of a positive-negative selection vector for functionally disrupting the endogenous heavy chain immunoglobulin locus of mouse.
Figure 23B:
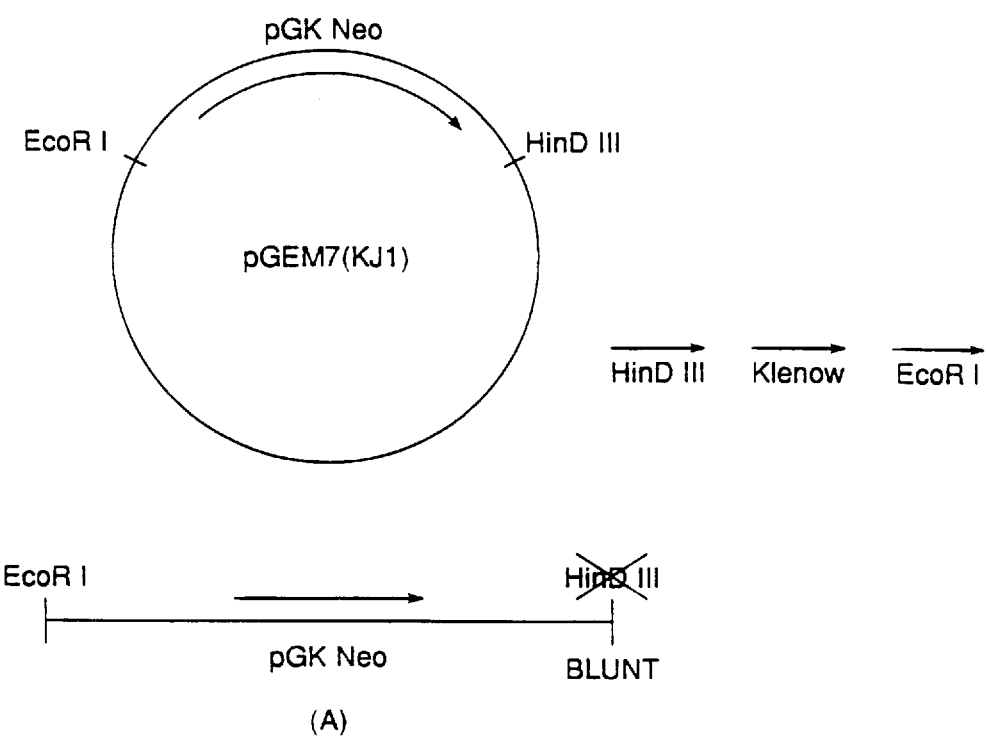
Figure 23C:
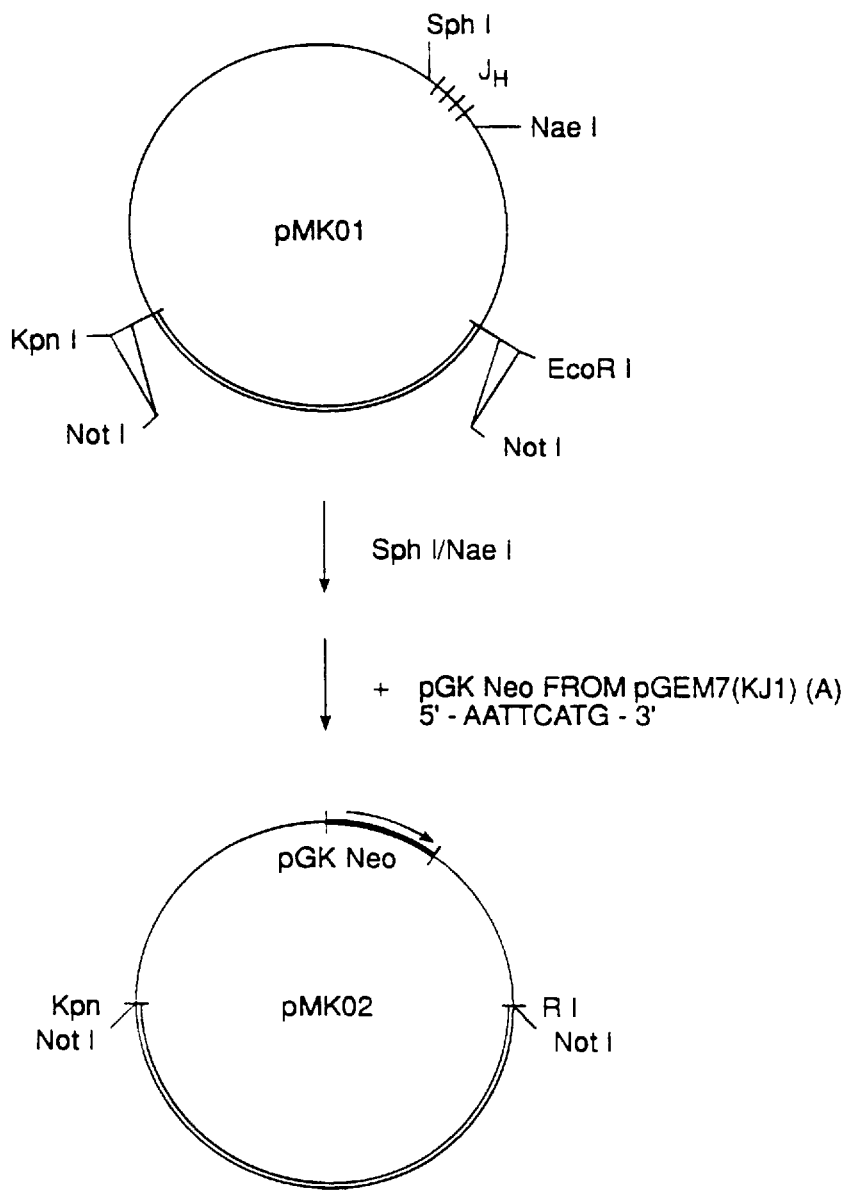
Figure 23D:
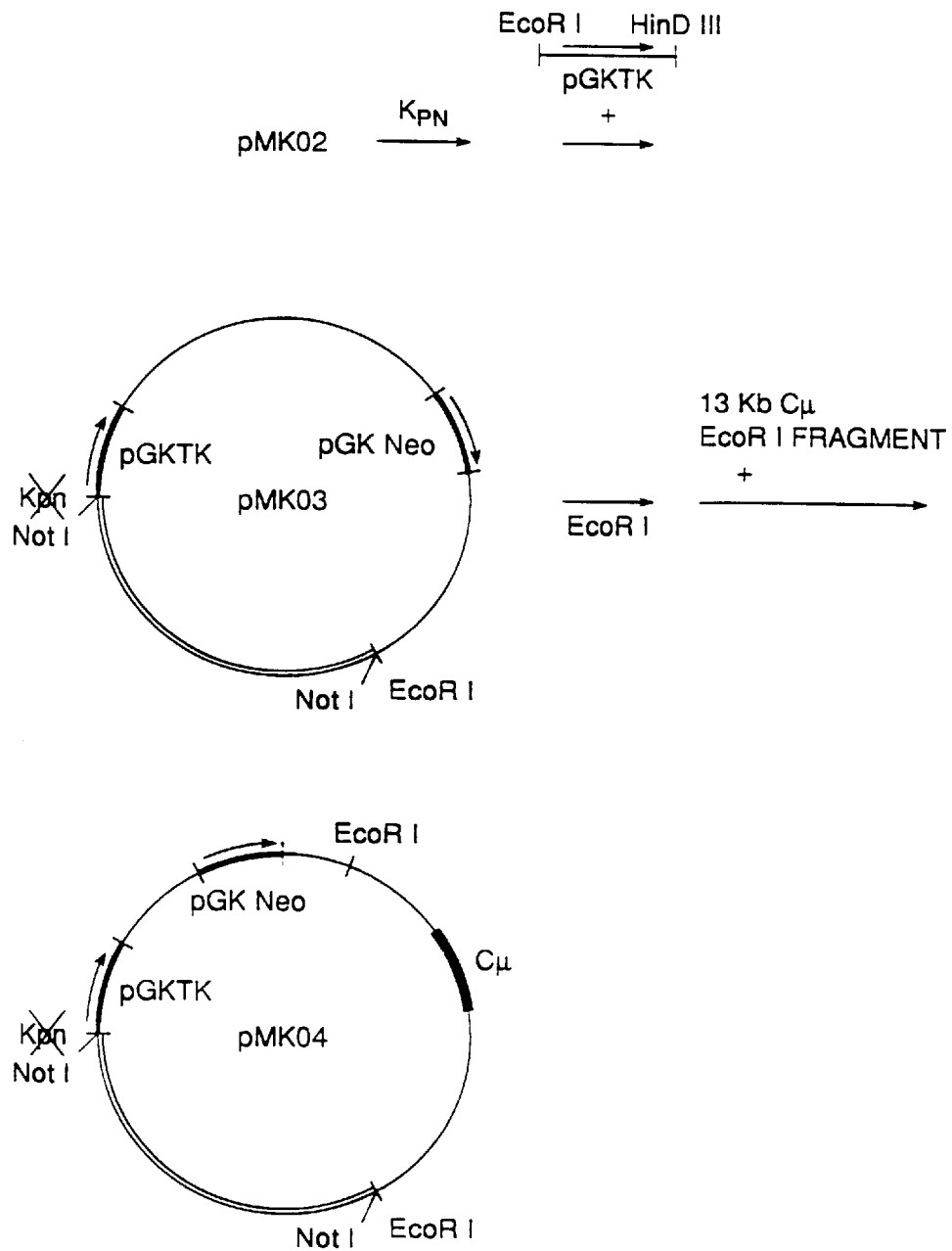
Figure 24A:
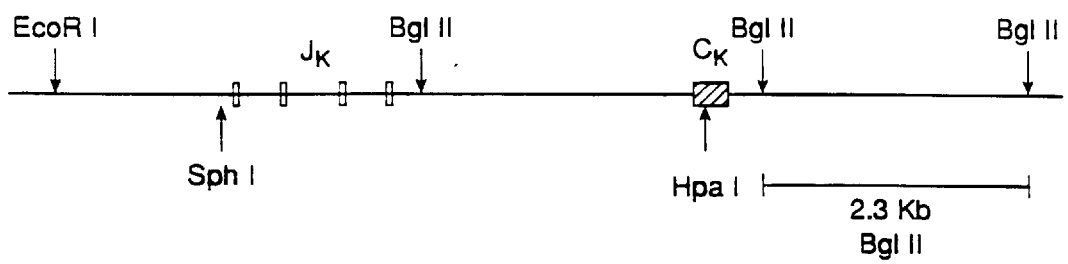
FIGS. 24A through 24C depict the construction of a positive-negative selection vector for functionally disrupting the endogenous immunoglobulin light chain loci in mouse.
Figure 24B:
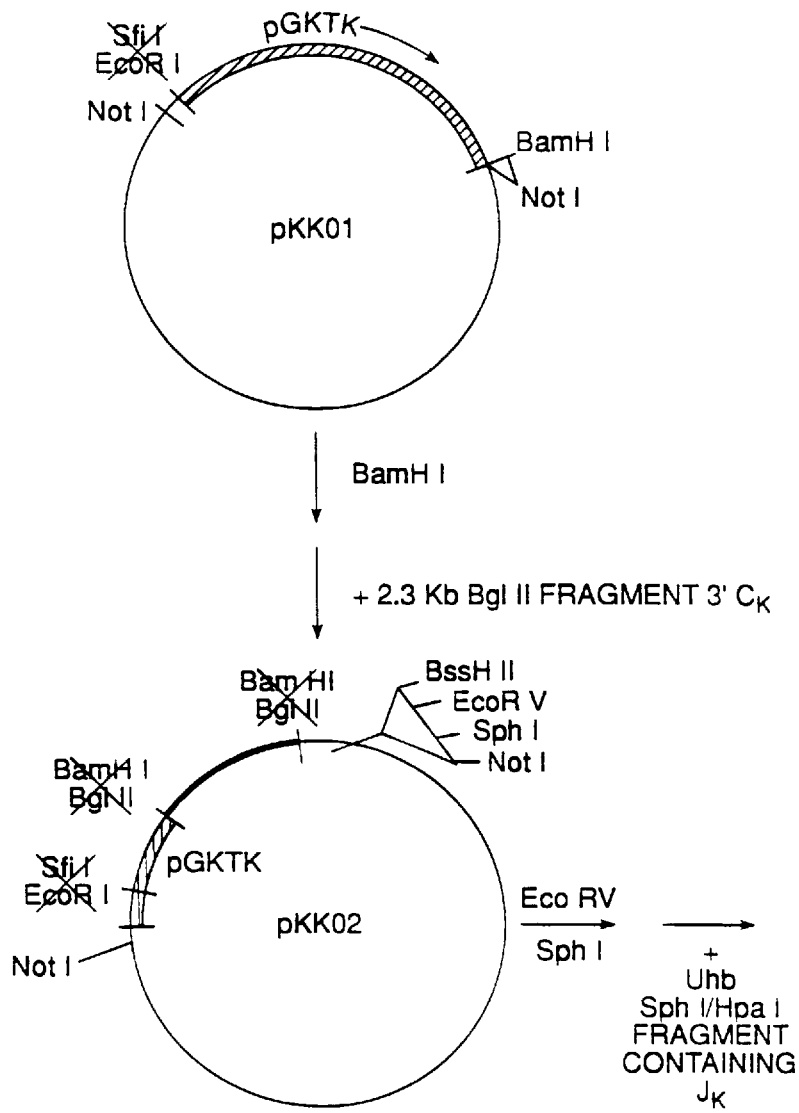
Figure 24C:
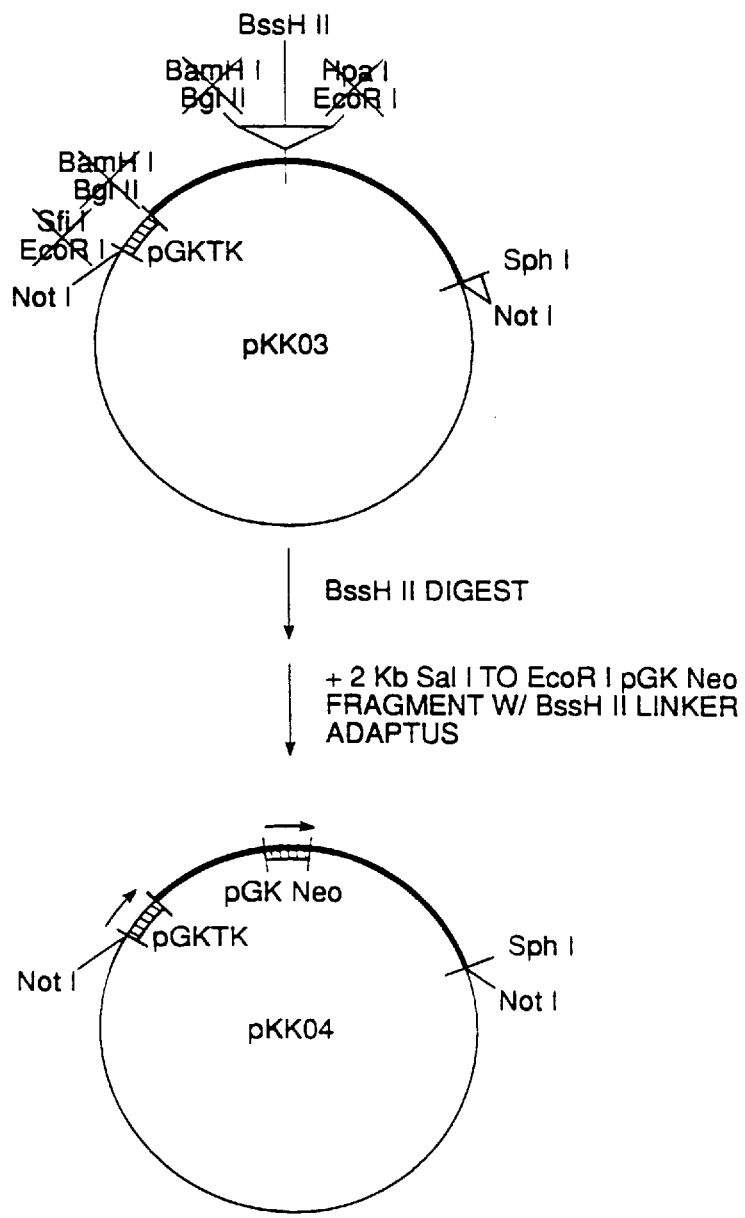

A 16 kb XhoI insert that was subcloned into the XhoI cut pE||1 so that Cκ is adjacent to the SmaI site. The resultant plasmid was designated pKap1. See FIG. 22.

The above Cκ specific oligonucleotide is used to probe the λ EMBL3/BamHI library to identify an 11 kb clone corresponding to fragment (d) of FIG. 20. A 5 kb SmaI fragment (fragment (b) in FIG. 20) is subcloned and subsequently inserted into pKap1 digested with SmaI. Those plasmids containing the correct orientation of J segments, Cκ and the $E\mu$ enhancer are designated pKap2.

One or more Vκ segments are thereafter subcloned into the MluI site of pKap2 to yield the plasmid pKapH which encodes the human Vκ segments, the human Jκ segments, the human Cκ segments and the human $E\mu$ enhancer. This insert is excised by digesting pKapH with NotI and purified by agarose gel electrophoresis. The thus purified insert is microinjected into the pronucleus of a mouse zygote as previously described.

C. Construction of κ Light Chain Minilocus by In Vivo Homologous Recombination

The 11 kb BamHI fragment (fragment (d) in FIG. 20) is cloned into BamHI digested pGP1 such that the 3' end is toward the SfiI site. The resultant plasmid is designated pKAPint. One or more Vκ segments is inserted into the polylinker between the BamHI and SpeI sites in pKAPint to form pKapHV. The insert of pKapHV is excised by digestion with NotI and purified. The insert from pKap2 is excised by digestion with NotI and purified. Each of these fragments contain regions of homology in that the fragment from pKapHV contains a 5 kb sequence of DNA that include the $J_\kappa$ segments which is substantially homologous to the 5 kb SmaI fragment contained in the insert obtained from pKap2. As such, these inserts are capable of homologously recombining when microinjected into a mouse zygote to form a transgene encoding $V_\kappa$, $J_\kappa$ and $C_\kappa$.

D. Construction of κ Light Chain Mini-Locus by Coinjection of Synthetic Vκ Region Fragment Together with Light Chain JC Construct Synthetic Vκ, region fragments are generated and isolated as previously described. These DNA fragments are coinjected with the purified NotI insert of plasmid pKap2 or plasmid pKapH. The coinjected DNA fragments are inserted into a single site in the chromosome. Some of the resulting transgenics will contain transgene inserts that have synthetic V regions located adjacent and upstream of the sequences in the pKap2 or pKapH construct. These animals will have a larger human κ light chain primary repertoire than those described in Example 6(B).

EXAMPLE 7

Isolation of Genomic Clones Corresponding to Rearranged and Expressed Copies of Immunoglobulin κ Light Chain Genes This example describes the cloning of immunoglobulin κ light chain genes from cultured cells that express an immunoglobulin of interest. Such cells may contain multiple alleles of a given immunoglobulin gene. For example, a hybridoma might contain four copies of the κ light chain gene, two copies from the fusion partner cell line and two copies from the original B-cell expressing the immunoglobulin of interest. Of these four copies, only one encodes the immunoglobulin of interest, despite the fact that several of them may be rearranged. The procedure described in this example allows for the selective cloning of the expressed copy of the κ light chain.

A. Double Stranded cDNA

Cells from human hybridoma, or lymphoma, or other cell line that synthesizes either cell surface or secreted or both forms of IgM with a κ light chain are used for the isolation of polyA+ RNA. The RNA is then used for the synthesis of oligo dT primed cDNA using the enzyme reverse transcriptase. The single stranded cDNA is then isolated and G residues are added to the 3' end using the enzyme polynucleotide terminal transferase. The Gtailed single-stranded cDNA is then purified and used as template for second strand synthesis (catalyzed by the enzyme DNA polymerase) using the following oligonucleotide as a primer:

5' - GAG GTA CAC TGA CAT ACT GGC ATG CCC
CCC CCC CCC - 3' (SEQ. ID NO: 26)

The double stranded cDNA is isolated and used for determining the nucleotide sequence of the 5' end of the mRNAs encoding the heavy and light chains of the expressed immunoglobulin molecule. Genomic clones of these expressed genes are then isolated. The procedure for cloning the expressed light chain gene is outlined in part B below.

B. Light Chain

The double stranded cDNA described in part A is denatured and used as a template for a third round of DNA synthesis using the following oligonucleotide primer:

5' - GTA CGC CAT ATC AGC TGG ATG AAG TCA TCA GAT
GGC GGG AAG ATG AAG ACA GAT GGT GCA - 3'

(SEQ. ID NO: 27)

This primer contains sequences specific for the constant portion of the κ light chain message (TCA TCA GAT GGC GGG AAG ATG AAG ACA GAT GGT GCA) (SEQ. ID NO:28) as well as unique sequences that can be used as a primer for the PCR amplification of the newly synthesized DNA strand (GTA CGC CAT ATC AGC TGG ATG AAG) (SEQ. ID NO:29). The sequence is amplified by PCR using the following two oligonucleotide primers:

5' - GAG GTA CAC TGA CAT ACT GGC ATG -3' (SEQ. ID NO: 30)
5' - GTA CGC CAT ATC AGC TGG ATG AAG -3'

The PCR amplified sequence is then purified by gel electrophoresis and used as template for dideoxy sequencing reactions using the following oligonucleotide as a primer:

5'-GAG GTA CAC TGA CAT ACT GGC ATG-3' (SEQ. ID NO:30)

The first 42 nucleotides of sequence will then be used to synthesize a unique probe for isolating the gene from which immunoglobulin message was transcribed. This synthetic 42 nucleotide segment of DNA will be referred to below as o-kappa.

A Southern blot of DNA, isolated from the Ig expressing cell line and digested individually and in pairwise combinations with several different restriction endonucleases including SmaI, is then probed with the 32-P labelled unique oligonucleotide o-kappa. A unique restriction endonuclease site is identified upstream of the rearranged V segment.

DNA from the Ig expressing cell line is then cut with SmaI and second enzyme (or BamHI or KpnI if there is SmaI site inside V segment). Any resulting non-blunted ends are treated with the enzyme T4 DNA polymerase to give blunt ended DNA molecules. Then add restriction site encoding linkers (BamHI, EcoRI or XhoI depending on what site does not exist in fragment) and cut with the corresponding linker enzyme to give DNA fragments with BamHI, EcoRI or XhoI ends. The DNA is then size fractionated by agarose gel electrophoresis, and the fraction including the DNA fragment covering the expressed V segment is cloned into lambda EMBL3 or Lambda FIX (Stratagene, La Jolla, Calif.). V segment containing clones are isolated using the unique probe o-kappa. DNA is isolated from positive clones and subcloned into the polylinker of pKap1. The resulting clone is called pRKL.

EXAMPLE 8

Isolation of Genomic Clones Corresponding to Rearranged Expressed Copies of Immunoglobuling Heavy Chain μ Genes This example describes the cloning of immunoglobulin heavy chain μ genes from cultured cells of expressed and immunoglobulin of interest. The procedure described in this example allows for the selective cloning of the expressed copy of a μ heavy chain gene.

Double-stranded cDNA is prepared and isolated as described in part μ of Example 7. The double-stranded cDNA is denatured and used as a template for a third round of DNA synthesis using the following oligonucleotide primer:

5' - GTA CGC CAT ATC AGC TGG ATG AAG ACA GGA GAC
GAG GGG GAA AAG GGT TGG GGC GGA TGC - 3'

(SEQ. ID NO: 31)

This primer contains sequences specific for the constant portion of the μ heavy chain message (ACA GGA GAC GAG GGG GAA AAG GGT TGG GGC GGA TGC) (SEQ. ID NO:32) as well as unique sequences that can be used as a primer for the PCR amplification of the newly synthesized DNA strand (GTA CGC CAT ATC AGC TGG ATG AAG) (SEQ. ID NO:29). The sequence is amplified by PCR using the following two oligonucleotide primers: 5'-GAG GTA CAC TGA CAT ACT GGC ATG-3' (SEQ. ID NO:30)

5'-GTA CTC CAT ATC AGC TGG ATG AAG-3' (SEQ. ID NO:33)

The PCR amplified sequence is then purified by gel electrophoresis and used as template for dideoxy sequencing reactions using the following oligonucleotide as a primer:

5'-GAG GTA CAC TGA CAT ACT GGC ATG-3' (SEQ. ID NO:30)

The first 42 nucleotides of sequence are then used to synthesize a unique probe for isolating the gene from which immunoglobulin message was transcribed. This synthetic 42 nucleotide segment of DNA will be referred to below as o-mu.

A Southern blot of DNA, isolated from the Ig expressing cell line and digested individually and in pairwise combinations with several different restriction endonucleases including MluI (MluI is a rare cutting enzyme that cleaves between the J segment and mu CH1), is then probed with the 32-P labelled unique oligonucleotide o-mu. A unique restriction endonuclease site is identified upstream of the rearranged V segment.

DNA from the IG expressing cell line is then cut with MluI and second enzyme. MluI or SpeI adapter linkers are then ligated onto the ends and cut to convert the upstream site to MluI or SpeI. The DNA is then size fractionated by agarose gel electrophoresis, and the fraction including the DNA fragment covering the expressed V segment is cloned directly into the plasmid pGPI. V segment containing clones are isolated using the unique probe o-mu, and the insert is subcloned into MluI or MluI/SpeI cut plasmid pCON2. The resulting plasmid is called pRMGH.

EXAMPLE 9

Deletion of the Mouse Heavy Chain Gene by Homologous Recombination

This example describes the deletion of the endogenous mouse heavy chain gene by homologous recombination in embryonic stem (ES) cells (Zjilstra, et al. (1989), *Nature*, 342, 435–438) followed by the transplantation of those ES cells into a mouse blastocyst embryo such that the ES cells colonize the germline of the resultant chimeric mouse (Teratocarcinomas and embryonic stem cells: a practical approach, E. J. Robertson, ed., IRL Press, Washington, D.C., 1987).

The construction of a DNA sequence that will homologously recombine into the mouse chromosome so as to delete the heavy chain J segments, thus eliminating the possibility of successful gene rearrangement at the heavy chain locus. The design of this construct is outlined below.

Plasmid pGP1 is digested with the restriction endonucleases BamHI and BglII and religated to form the plasmid pGP1d1. This plasmid is then used to build the so-called gene knockout construct.

To obtain sequences homologous to the desired target region of the mouse genome, mouse genomic clones are isolated from a phage library derived from non-lymphoid tissue (such as liver) using the $J_H$ specific oligonucleotide probe:

5' - GGT CTA TGA TAG TGT GAC TAC TTT GAC TAC TGG
      GGC CAA GGC - 3' (SEQ. ID NO: 34)

A 3.5 kb KpnI to EcoRI fragment that hybridizes with this probe is isolated from DNA derived from positive phage clones. This fragment is subcloned into KpnI/EcoRI digested pGP1d1 to form the plasmid pMKO1.

Neomycin resistance (Neo) and Herpes Simplex Virus thymidine kinase (TK) genes for drug selection of recombinants (M. Capecchi (1989), *Science*, 244, 1288–1292) are then isolated as follows. The plasmid pGEM7(KJ1) (M. A. Rudnicki, Mar. 15, 1989) is digested with HindIII and the ends blunted with the klenow form of DNA pol I. The DNA is then cut with EcoRI and the pGKNeo fragment is isolated and cloned into SphI/NaeI cut pMKO1 using the following oligonucleotide as an adapter:

5'-AATTCATG-3'

The resulting-plasmid is designated pMKO2. This plasmid contains the neomycin resistance gene flanked by sequences that flank the mouse $J_H$ segments. This plasmid alone can be used for deletion of the heavy chain gene. Alternatively the Herpes TK gene can be added to the construct to improve the frequency of homologous recombination events in Neo resistant clones (M. Capecchi (1989), *Science*, 244, 1288–1292). This is done as follows. The EcoRI to HindIII PGKTK fragment of pGEM7(TK) (M. A. Rudnicki) is isolated and cloned into the KpnI site of pMKO2 using the following oligonucleotide as adapters:

5'-AATTGTAC-3'
5'-AGCTGTAC-3'

The resulting plasmid is designated pMKO3.

To further improve the overall efficiency of homologous recombination, a large segment of DNA that is homologous to the target sequence is then added to the construct. A 13 kb EcoRI fragment, that hybridizes with the $C\mu$ specific oligonucleotide described below:

5' - GCA TCC TGG AAG GTT CAG ATG AAT ACC
      TTG TAT GCA AAA TCC - 3' (SEQ. ID NO: 35)

This 12 kb fragment includes the $C\mu$ coding exons, or a substantial portion of that fragment which includes the 5' EcoRI end, is isolated from a mouse genomic phage library and subcloned into the EcoRI site of pMKO3. The resultant plasmid is designated pMKO4.

The insert of pMKO4 is isolated by digestion with NotI and electroporated into ES cells. Homologous recombinant clones are isolated used to generate a $J_H$ deleted mouse as described by Zjilstra, et al. (1989), *Nature*, 342, 435–438.

EXAMPLE 10

Deletion of the Mouse Light Chain Gene by Homologous Recombination

This example describes the deletion of the endogenous mouse light chain gene by homologous recombination in embryonic stem cells (see previous Example).

A DNA sequence that homologously recombines into the mouse chromosome to delete the κ light chain constant region exon is constructed. The design of this construct is outlined below.

A 2 kb BamHII to EcoRI thymidine kinase fragment from pGEM7(TK)Sal (M. A. Rudnicki, Whitehead Institute) is isolated and subcloned into the BamHI/SfiI digested pGP1 using the following oligonucleotide adapter:

5'-AATTTTG-3'

The resulting plasmid is designated pKKO1.

To obtain sequences homologous to the desired target region of the mouse genome, mouse genomic clones are isolated from a phage library derived from non-lymphoid tissue (such as liver) using the mouse κ light chain specific oligo designated o-MKC given below:

5' - GGC TGA TGC TGC ACC AAC TGT ATC CAT
      CTT CCC ACC ATC CAG - 3' (SEQ. ID NO: 36)

DNA is isolated from positive clone and a 2.3 kb BglII fragment (P. S. Neumaier and H. G. Zachau (1983), *Nucl. Acids Res.*, 11, 3631–3656) that hybridizes with probe o-MK3 is isolated. The sequence of probe o-MK3 is as follows:

5' - CAT TCT GGG TAT GAA GAG CCC ACG TAT
      CAA AGG TTA CAT TAG - 3' (SEQ. ID NO: 37)

This 2.3 kb BglII fragment is subcloned into BamHI digested pKKO1 such that the 3' end of the fragment is adjacent to the polylinker SfiI site. The resulting plasmid is designated pKKO2.

The 4 kb SphI to HpaI DNA fragment that hybridizes with oligonucleotide o-MKC is isolated from positive phage clone and subcloned into EcoRV to SphI digested plasmid pKKO2. The resulting plasmid is designated pKKO3.

A 2 kb SalI to EcoRI fragment of pGEM7(KJ1)Sal (M. A. Rudnicki, Mar. 15, 1989) is isolated and cloned into the BssHII site of plasmid pKKO3 using linker adapters. This is carried out by first ligating a mixture of the following three oligonucleotides to the 2 kb SalI to EcoRI fragment:

5'-CAGCGCGC-3'

5'-GATCGCGCGCTG-3 (SEQ. ID NO:38)

5'-AATTGCGCGCTG-3' (SEQ. ID NO:39)

The ligation mixture is then digested with the enzyme BssHII and ligated to BssHII digested plasmid pKKO3. The resulting plasmid is designated pKKO4.

The insert of pKKO4 is isolated by digesting with NotI and electroporated into ES cells. Homologous recombinant clones are isolated and used to generate a $C_K$ deleted mouse as described by Zjilstra, et al. (1989), *Nature,* 342, 435–438.

EXAMPLE 11

Inactivation of the Mouse Kappa Light Chain Gene by Homologous Recombination

This example describes the inactivation of the mouse endogenous kappa locus by homologous recombination in embryonic stem (ES) cells followed by introduction of the mutated gene into the mouse germ line by injection of targeted ES cells bearing an inactivated kappa allele into early mouse embryos (blastocysts).

The strategy is to delete $J_K$ and $C_K$ by homologous recombination with a vector containing DNA sequences homologous to the mouse kappa locus in which a 4.5 kb segment of the locus, spanning the $J_K$ gene and $C_K$ segments, is deleted and replaced by the selectable marker neo.

Construction of the kappa targeting vector

The plasmid pGEM7 (KJ1) (M. A. Rudnicki, Whitehead Institute) contains the neomycin resistance gene (neo), used for drug selection of transfected ES cells, under the transcriptional control of the mouse phosphoglycerate kinase (pgk) promoter (XbaI/I/TaqI fragment; Adra, C. N. et al., (1987) *Gene,* 60, 65–74) in the cloning vector pGEM-72f (+). The plasmid also includes a heterologous polyadenylation site for the neo gene, derived from the 3' region of the mouse pgk gene (PvuII/HindIII fragment; Boer, P. H., et al., (1990) *Biochemical Genetics,* 28, 299–308). This plasmid was used as the starting point for construction of the kappa targeting vector. The first step was to insert sequences homologous to the kappa locus 3' of the neo expression cassette.

Mouse kappa chain sequences (FIG. 25a) were isolated from a genomic phage library derived from liver DNA using oligonucleotide probes specific for the CK locus:

5'- GGC TGA TGC TGC ACC AAC TGT ATC CAT CTT
CCC ACC ATC CAG -3' (SEQ. ID NO: 36)

and for the JK5 gene segment:

5'- CTC ACG TTC GGT GCT GGG ACC AAG CTG GAG
CTG AAA CGT AAG -3'.(SEQ. ID NO: 40)

Figure 25:
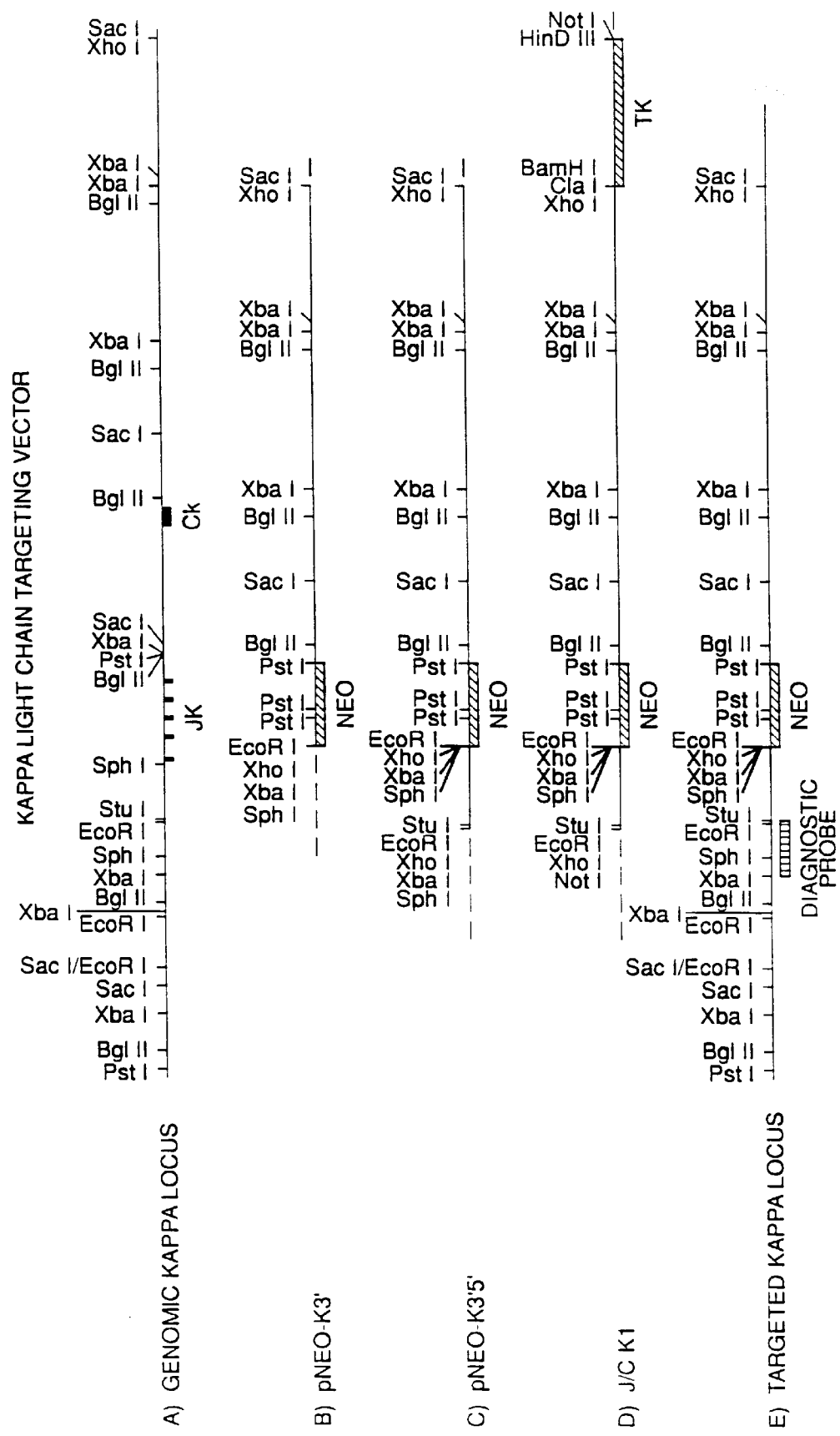
FIGS. 25a through e depict the structure of a kappa light chain targeting vector.

An 8 kb BglII/SacI fragment extending 3' of the mouse $C_K$ segment was isolated from a positive phage clone in two pieces, as a 1.2 kb BglII/SacI fragment and a 6.8 kb SacI fragment, and subcloned into BglII/SacI digested pGEM7 (KJ1) to generate the plasmid pNEO-K3' (FIG. 25b).

A 1.2 kb EcoRI/SphI fragment extending 5' of the $J_K$ region was also isolated from a positive phage clone. An SphI/XbaI/BglII/EcoRI adaptor was ligated to the SphI site of this fragment, and the resulting EcoRI fragment was ligated into EcoRI digested pNEO-K3', in the same 5' to 3' orientation as the neo gene and the downstream 3' kappa sequences, to generate pNEO-K5'3' (FIG. 25c).

The Herpes Simplex Virus (HSV) thymidine kinase (TK) gene was then included in the construct in order to allow for enrichment of ES clones bearing-homologous recombinants, as described by Mansour et al. ((1988) *Nature,* 336, 348–352). The HSV TK cassette was obtained from the plasmid pGEM7 (TK) (M. A. Rudnicki), which contains the structural sequences for the HSV TK gene bracketed by the mouse pgk promoter and polyadenylation sequences as described above for pGEM7 (KJ1). The EcoRI site of pGEM7 (TK) was modified to a BamHI site and the TK cassette was then excised as a BamHI/HindIII fragment and subcloned into pGP1b to generate pGP1b-TK. This plasmid was linearized at the XhoI site and the XhoI fragment from pNEO-K5'3', containing the neo gene flanked by genomic sequences from 5' of JK and 3' of CK, was inserted into pGP1b-TK to generate the targeting vector J/C KI (FIG. 25d). The putative structure of the genomic kappa locus following homologous recombination with J/C K1 is shown in FIG. 25e.

Generation and analysis of ES cells with targeted inactivation of a kappa allele AB-1 ES cells were grown on mitotically inactive SNL76/7 cell feeder layers (McMahon, A. P. and Bradley, A. (1990) *Cell,* 62, 1073–1085) essentially as described (Robertson, E. J. (1987) in *Teratocarcinomas and Embryonic Stem Cells: A Practical Approach*. E. J. Robertson, ed. (Oxford: IRL Press), p. 71–112).

The kappa chain inactivation vector J/C K1 was digested with NotI and electroporated into AB-1 cells by the methods described (Hasty, P. R., et al. (1991) *Nature,* 350, 243–246). Electroporated cells were plated onto 100 mm dishes at a density of 2–5×10$^6$ cells/dish. After 24 hours, G418 (200 µg/ml of active component) and FIAU (0.5 µM) were added to the medium, and drug-resistant clones were allowed to develop over 10–11 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described (Laird, P. W. et al., (1991) *Nucl. Acids Res.,* 19,) digested with XbaI and probed with the 800 bp EcoRI/XbaI fragment indicated in FIG. 25e as the diagnostic probe. This probe detects a 3.7 kb XbaI fragment in the wild type locus, and a diagnostic 1.8 kb band in a locus which has homologously recombined with the targeting vector (see FIG. 25a and e). Of 358 G418 and FIAU resistant clones screened by Southern blot analysis, 4 displayed the 1.8 kb XbaI band indicative of a homologous recombination at the kappa locus. These 4 clones were further digested with the enzymes BglII, SacI, and PstI to verify that the vector integrated homologously into one of the kappa alleles. When probed with the diagnostic 800 bp EcoRI/XbaI fragment, BglII, SacI, and PstI digests of wild type DNA produce fragments of 4.1, 5.4, and 7 kb, respectively, whereas the presence of a targeted kappa allele would be indicated by fragments of 2.4, 7.5, and 5.7 kb, respectively (see FIG. 25a and e). All 4 positive clones detected by the XbaI digest showed the expected BglII, SacI, and PstI restriction fragments diagnostic of a homologous recombination at the kappa light chain.

Generation of mice bearing the inactivated kappa chain

The 4 targeted ES clones described in the previous section were injected into C57Bl/6J blastocysts as described (Bradley, A. (1987) in *Teratocarcinomas and Embryonic Stem Cells: A Practical Approach*. E. J. Robertson, ed.

(Oxford: IRL Press), p. 113–151) and transferred into the uteri of pseudopregnant females to generate chimeric mice representing a mixture of cells derived from the input ES cells and the host blastocyst. Chimeric animals are visually identified by the presence of agouti coat coloration, derived from the ES cell line, on the black C57Bl/6J background. The AB1 ES cells are an XY cell line, thus male chimeras are bred with C57BL/6J females and the offspring monitored for the presence of the dominant agouti coat color. Agouti offspring are indicative of germline transmission of the ES genome. The heterozygosity of agouti offspring for the kappa chain inactivation is verified by Southern blot analysis of DNA from tail biopsies using the diagnostic probe utilized in identifying targeted ES clones. Brother-sister matings of heterozygotes are then carried out to generate mice homozygous for the kappa chain mutation.

EXAMPLE 12

Inactivation of the Mouse Heavy Chain Gene by Homologous Recombination

This example describes the inactivation of the endogenous murine immunoglobulin heavy chain locus by homologous recombination in embryonic stem (ES) cells. The strategy is to delete the endogenous heavy chain J segments by homologous recombination with a vector containing heavy chain sequences from which the $J_H$ region has been deleted and replaced by the gene for the selectable marker neo.

Construction of a heavy chain targeting vector

Mouse heavy chain sequences containing the $J_H$ region (FIG. 26a) were isolated from a genomic phage library derived from the D3 ES cell line (Gossler, et al., (1986) Proc. Natl. Acad. Sci. U.S.A., 83, 9065–9069) using a $J_H4$ specific oligonucleotide probe:

5'-ACT ATG CTA TGG ACT ACT GGG GTC AAG GAA CCT CAG TCA CCG-3' (SEQ. ID NO:41)

Figure 26A:
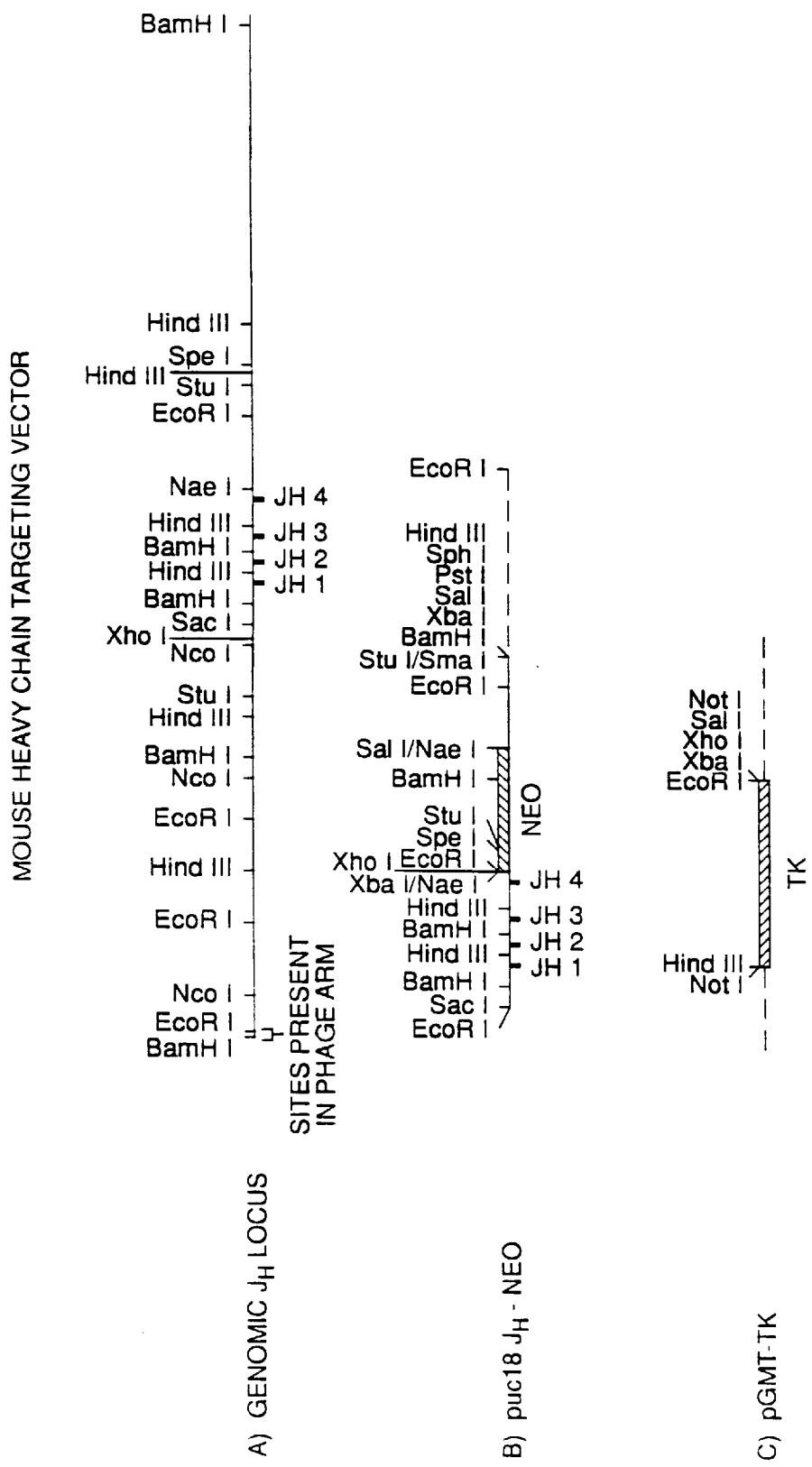
Figure 26B:
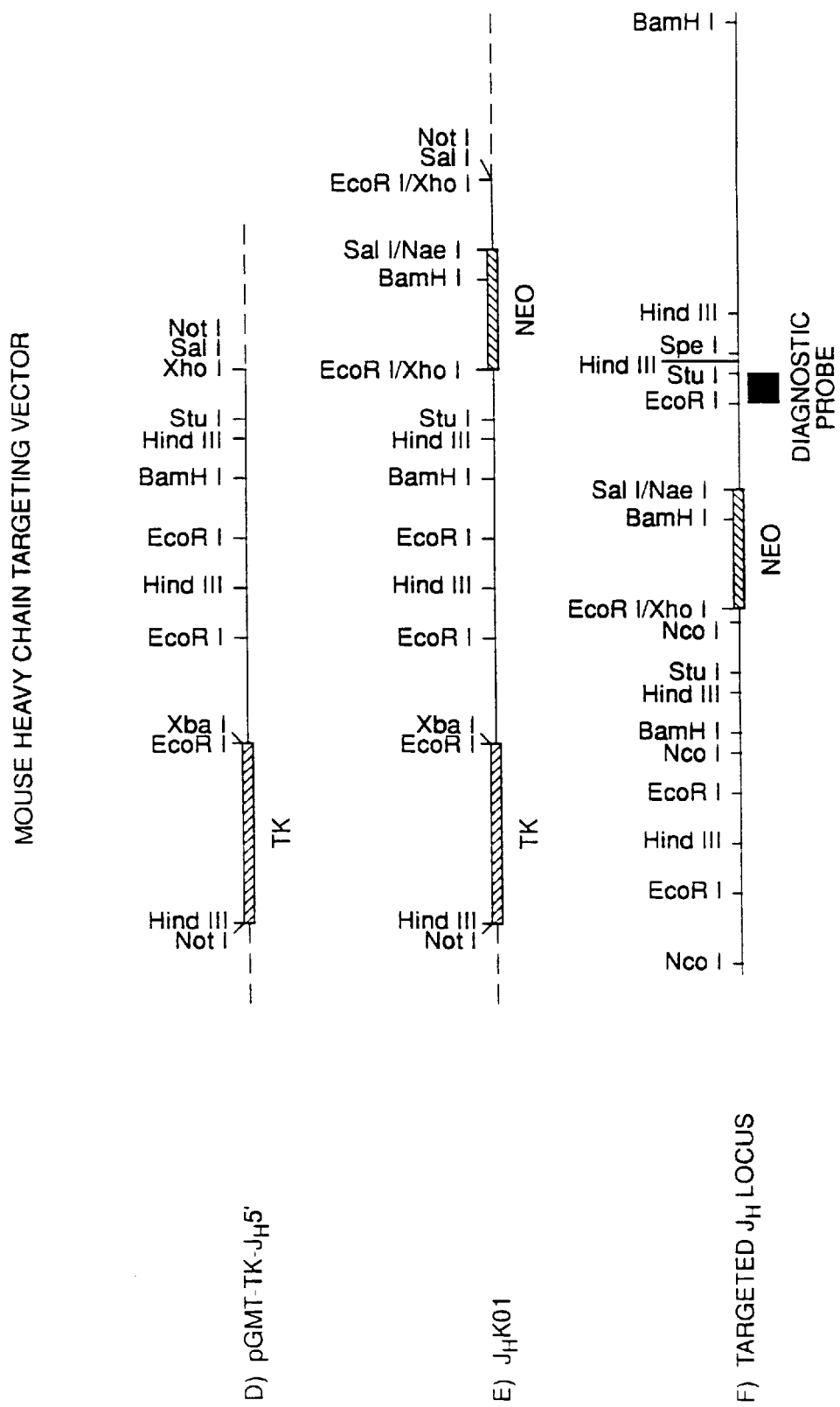

A 3.5 kb genomic SacI/StuI fragment, spanning the $J_H$ region, was isolated from a positive phage clone and subcloned into SacI/SmaI digested puc18. The resulting plasmid was designated puc18 $J_H$. The neomycin resistance gene (neo), used for drug selection of transfected ES cells, was derived from the plasmid pGEM7 (KJ1). The HindIII site in pGEM7 (KJ1) was converted to a SalI site by addition of a synthetic adaptor, and the neo expression cassette excised by digestion with XbaI/SalI. The ends of the neo fragment were then blunted by treatment with the Klenow form of DNA polI, and the neo fragment was subcloned into the NaeI site of puc18 $J_H$, generating the plasmid puc18 $J_H$-neo (FIG. 26b).

Further construction of the targeting vector was carried out in a derivative of the plasmid pGP1b. pGP1b was digested with the restriction enzyme NotI and ligated with the following oligonucleotide as an adaptor:

5'- GGC CGC TCG ACG ATA GCC TCG AGG CTA TAA

ATC TAG AAG AAT TCC AGC AAA GCT TTG GC -3'

(SEQ. ID NO: 42)

The resulting plasmid, called pGMT, was used to build the mouse immunoglobulin heavy chain targeting construct.

The Herpes Simplex Virus (HSV) thymidine kinase (TK) gene was included in the construct in order to allow for enrichment of ES clones bearing homologous recombinants, as described by Mansour et al. ((1988) Nature 336, 348–352). The HSV TK gene was obtained from the plasmid pGEM7 (TK) by digestion with EcoRI and HindIII. The TK DNA fragment was subcloned between the EcoRI and HindIII sites of pGMT, creating the plasmid pGMT-TK (FIG. 26c).

To provide an extensive region of homology to the target sequence, a 5.9 kb genomic XbaI/XhoI fragment, situated 5' of the $J_H$ region, was derived from a positive genomic phage clone by limit digestion of the DNA with XhoI, and partial digestion with XbaI. As noted in FIGS. 26a and 26b, this XbaI site is not present in genomic DNA, but is rather derived from phage sequences immediately flanking the cloned genomic heavy chain insert in the positive phage clone. The fragment was subcloned into XbaI/XhoI digested pGMT-TK, to generate the plasmid pGMT-TK-$J_H5'$ (FIG. 26d).

The final step in the construction involved the excision of the 3 kb EcoRI fragment from puc18 $J_H$-neo which contained the neo gene and flanking genomic sequences. This fragment was blunted by Klenow polymerase and subcloned into the similarly blunted XhoI site of pGMT-TK-$J_H5'$. The resulting construct, $J_H$KO1 (FIG. 26e), contains 6.9 kb of genomic sequences flanking the $J_H$ locus, with a 2.3 kb deletion spanning the $J_H$ region into which has been inserted the neo gene. FIG. 25f shows the structure of an endogenous heavy chain allele after homologous recombination with the targeting construct.

EXAMPLE 13

Generation and analysis of targeted ES cells

AB-1 ES cells (McMahon, A. P. and Bradley, A. (1990) Cell 62, 1073–1085) were grown on mitotically inactive SNL76/7 cell feeder layers essentially as described (Robertson, E. J. (1987) Teratocarcinomas and Embryonic Stem Cells: A Practical Approach. E. J. Robertson, ed. (Oxford: IRL Press), pp. 71–112).

The heavy chain inactivation vector $J_H$KO1 was digested with NotI and electroporated into AB-1 cells by the methods described (Hasty, P. R., et al. (1991) Nature 350, 243–246). Electroporated cells were plated into 100 mm dishes at a density of $2–5\times10^6$ cells/dish. After 24 hours, G418 (200 mg/ml of active component) and FIAU (0.5 mM) were added to the medium, and drug-resistant clones were allowed to develop over 8–10 days. Clones were picked, trypsinized, divided into two portions, and further expanded. Half of the cells derived from each clone were then frozen and the other half analyzed for homologous recombination between vector and target sequences.

DNA analysis is carried out by Southern blot hybridization. DNA is isolated from the clones as described (Laird, P. W. et al., (1991) Nucl. Acids Res., 19.) digested with HindIII and probed with the 500 bp EcoRI/StuI fragment designated as the diagnostic probe in FIG. 26f. This probe detects a HindIII fragment of 2.3 kb in the wild type locus, whereas a 5.3 kb band is diagnostic of a targeted locus which has homologously recombined with the targeting vector (see FIGS. 26a and f). Additional digests with the enzymes SpeI, StuI, and BamHI are carried out to verify the targeted disruption of the heavy chain allele.

EXAMPLE 14

Heavy Chain Minilocus Transgene

A. Construction of plasmid vectors for cloning large DNA sequences 1. pGP1a

The plasmid pBR322 was digested with EcoRI and StyI and ligated with the following oligonucleotides:

oligo-42 5'- caa gag ccc gcc taa tga gcg ggc ttt ttt ttg cat act gcg gcc gct -3' (SEQ. ID NO: 43)

oligo-43 5'- aat tag cgg ccg cag tat gca aaa aaa agc ccg ctc att agg cgg gct -3' (SEQ. ID NO: 44)

The resulting plasmid, pGP1a, is designed for cloning very large DNA constructs that can be excised by the rare cutting restriction enzyme NotI. It contains a NotI restriction site downstream (relative to the ampicillin resistance gene, AmpR) of a strong transcription termination signal derived from the trpA gene (Christie, G. E. et al. (1981) Proc. Natl. Acad. Sci. USA, 78, 4180). This termination signal reduces the potential toxicity of coding sequences inserted into the NotI site by eliminating readthrough transcription from the AmpR gene. In addition, this plasmid is low copy relative to the pUC plasmids because it retains the pBR322 copy number control region. The low copy number further reduces the potential toxicity of insert sequences and reduces the selection against large inserts due to DNA replication.

2. pGP1b pGP1a was digested with NotI and ligated with the following oligonucleotides:

oligo-47 5'- ggc cgc aag ctt act gct gga tcc tta att aat cga tag tga tct cga ggc -3' (SEQ. ID NO: 45)

oligo-48 5'- ggc cgc ctc gag atc act atc gat taa tta agg atc cag cag taa gct tgc -3' (SEQ. ID NO: 46)

The resulting plasmid, pGP1b, contains a short polylinker region flanked by NotI sites. This facilitates the construction of large inserts that can be excised by NotI digestion.

3. pGPe

The following oligonucleotides:

oligo-44 5'- ctc cag gat cca gat atc agt acc tga aac agg gct tgc -3' oligo-45 5'- ctc gag cat gca cag gac ctg gag cac aca cag cct tcc -3' (SEQ. ID NO: 48)

were used to amplify the immunoglobulin heavy chain 3' enhancer (S. Petterson, et al. (1990) Nature, 344, 165–168) from rat liver DNA by the polymerase chain reaction technique.

Figure 27:
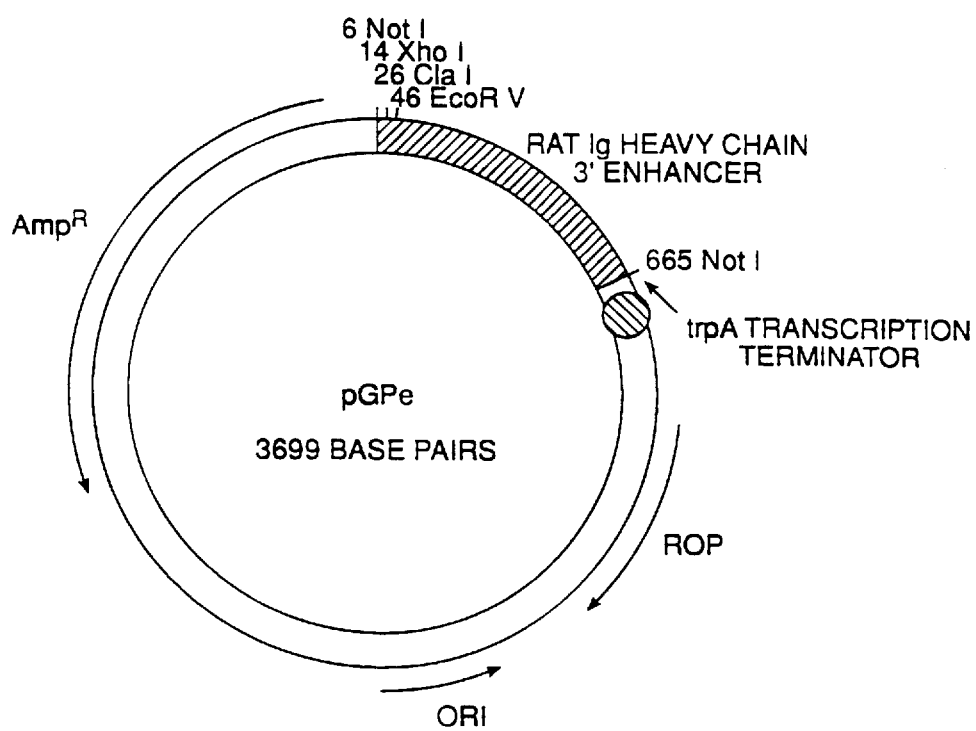
FIG. 27 depicts the map of vector pGPe.

The amplified product was digested with BamHI and SphI and cloned into BamHI/SphI digested pNNO3 (pNNO3 is a pUC derived plasmid that contains a polylinker with the following restriction sites, listed in order: NotI, BamHI, NcoI, ClaI, EcoRV, XbaI, SacI, XhoI, SphI, PstI, BglII, EcoRI, SmaI, KpnI, HindIII, and NotI). The resulting plasmid, pRE3, was digested with BamHI and HindIII, and the insert containing the rat Ig heavy chain 3' enhancer cloned into BamHI/HindIII digested pGP1b. The resulting plasmid, pGPe (FIG. 27 and Table 1), contains several unique restriction sites into which sequences can be cloned and subsequently excised together with the 3' enhancer by NotI digestion.

TABLE 1

Sequence of vector pGPe (SEQ. ID NO: 49).

AATTAGCggccgcctcgagatcactatcgattaattaaggatccagatatcagtacctgaaacagggcttgctcacaaca tctctctctctgtctctctgtctctgtgtgtgtgtctctctctgtctctgtctctctctgtctctctgtctctgtgtgtg tctctctctgtctctctctctgtctctctgtctctctctgtctgtctctgtctctgtctctgtctctctctctctctctc tctctctctctctctcacacacacacacacacacacacacacacctgccgagtgactcactctgtgcagggttggccc tcggggcacatgcaaatggatgtttgttccatgcagaaaaacatgtttctcattctctgagccaaaaatagcatcaatga ttccccaccctgcagctgcaggttcaccccacctggccaggttgaccagctttggggatggggctgggggttccatgac ccctaacggtgacattgaattcagtgttttcccatttatcgacactgctggaatctgaccctaggagggaatgacaggag ataggcaaggtccaaacaccccagggaagtgggagagacaggaaggctgtgtgtgctccaggtcctgtgcatgctgcaga tctgaattcccgggtaccaagcttgcGGCCGCAGTATGCAAAAAAAGCCCGCTCATTAGGCGGGCTCTTGGCAGAACAT

ATCCATCGCGTCCGCCATCTCCAGCAGCCGCACGCGGCGCATCTCGGGCAGCGTTGGGTCCTGGCCACGGGTGCGCATGA

TCGTGCTCCTGTCGTTGAGGACCCGGCTAGGCTGGCGGGGTTGCCTTACTGGTTAGCAGAATGAATCACCGATACGCGAG

CGAACGTGAAGCGACTGCTGCTGCAAAACGTCTGCGACCTGAGCAACAACATGAATGGTCTTCGGTTTCCGTGTTTCGTA

AAGTCTGGAAACGCGGAAGTCAGCGCCCTGCACCATTATGTTCCGGATCTGCATCGCAGGATGCTGCTGGCTACCCTGTG

GAACACCTACATCTGTATTAACGAAGCGCTGGCATTGACCCTGAGTGATTTTCTCTGGTCCCGCCGCATCCATACCGCC

AGTTGTTTACCCTCACAACGTTCCAGTAACCGGGCATGTTCATCATCAGTAACCCGTATCGTGAGCATCCTCTCTCGTTT

CATCGGTATCATTACCCCCATGAACAGAAATTCCCCCTTACACGGAGGCATCAAGTGACCAAACAGGAAAAAACCGCCCT

TAACATGGCCCGCTTTATCAGAAGCCAGACATTAACGCTTCTGGAGAAACTCAACGAGCTGGACGCGGATGAACAGGCAG

ACATCTGTGAATCGCTTCACGACCACGCTGATGAGCTTTACCGCAGCTGCCTCGCGCGTTTCGGTGATGACGGTGAAAAC

CTCTGACACATGCAGCTCCCGGAGACGGTCACAGCTTGTCTGTAAGCGGATGCCGGGAGCAGACAAGCCCGTCAGGGCGC

GTCAGCGGGTGTTGGCGGGTGTCGGGGCGCAGCCATGACCCAGTCACGTAGCGATAGCGGAGTGTATACTGGCTTAACTA

TABLE 1-continued

Sequence of vector pGPe (SEQ. ID NO: 49).

TGCGGCATCAGAGCAGATTGTACTGAGAGTGCACCATATGCGGTGTGAAATACCGCACAGATGCGTAAGGAGAAAATACC

GCATCAGGCGCTCTTCCGCTTCCTCGCTCACTGACTCGCTGCGCTCGGTCGTTCGGCTGCGGCGAGCGGTATCAGCTCAC

TCAAAGGCGGTAATACGGTTATCCACAGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCCTGACGAGCATCACAAAAATCGACGCT

CAAGTCAGAGGTGGCGAAACCCGACAGGACTATAAAGATACCAGGCGTTTCCCCCTGGAAGCTCCCTCGTGCGCTCTCCT

GTTCCGACCCTGCCGCTTACCGGATACCTGTCCGCCTTTCTCCCTTCGGGAAGCGTGGCGCTTTCTCATAGCTCACGCTG

TAGGTATCTCAGTTCGGTGTAGGTCGTTCGCTCCAAGCTGGGCTGTGTGCACGAACCCCCCGTTCAGCCCGACCGCTGCG

CCTTATCCGGTAACTATCGTCTTGAGTCCAACCCGGTAAGACACGACTTATCGCCACTGGCAGCAGCCACTGGTAACAGG

ATTAGCAGAGCGAGGTATGTAGGCGGTGCTACAGAGTTCTTGAAGTGGTGGCCTAACTACGGCTACACTAGAAGGACAGT

ATTTGGTATCTGCGCTCTGCTGAAGCCAGTTACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAAAAAAGGATCTCAAGAAGATCCTTTGATCTTT

TCTACGGGGTCTGACGCTCAGTGGAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTAAACTTGGTCTGACAGTTACCAAT

GCTTAATCAGTGAGGCACCTATCTCAGCGATCTGTCTATTTCGTTCATCCATAGTTGCCTGACTCCCCGTCGTGTAGATA

ACTACGATACGGGAGGGCTTACCATCTGGCCCCAGTGCTGCAATGATACCGCGAGACCCACGCTCACCGGCTCCAGATTT

ATCAGCAATAAACCAGCCAGCCGGAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTGTTGCCATTGCTGCAGGCATCGTG

GTGTCACGCTCGTCGTTTGGTATGGCTTCATTCAGCTCCGGTTCCCAACGATCAAGGCGAGTTACATGATCCCCCATGTT

GTGCAAAAAAGCGGTTAGCTCCTTCGGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTGACTGGTGAGTACTCAACCAAGTCA

TTCTGAGAATAGTGTATGCGGCGACCGAGTTGCTCTTGCCCGGCGTCAACACGGGATAATACCGCGCCACATAGCAGAAC

TTTAAAAGTGCTCATCATTGGAAAACGTTCTTCGGGGCGAAAACTCTCAAGGATCTTACCGCTGTTGAGATCCAGTTCGA

TGTAACCCACTCGTGCACCCAACTGATCTTCAGCATCTTTTACTTTCACCAGCGTTTCTGGGTGAGCAAAAACAGGAAGG

CAAAATGCCGCAAAAAAGGGAATAAGGGCGACACGGAAATGTTGAATACTCATACTCTTCCTTTTTCAATATTATTGAAG

CATTTATCAGGGTTATTGTCTCATGAGCGGATACATATTTGAATGTATTTAGAAAAATAAACAAATAGGGGTTCCGCGCA

CATTTCCCCGAAAAGTGCCACCTGACGTCTAAGAAACCATTATTATCATGACATTAACCTATAAAAATAGGCGTATCACG

AGGCCCTTTCGTCTTCAAG

B. Construction of IgM expressing minilocus transgene, pIGM1

1. Isolation of J-μ constant region clones and construction of pJM1

A human placental genomic DNA library cloned into the phage vector λEMBL3/SP6/T7 (Clonetech Laboratories, Inc., Palo Alto, Calif.) was screened with the human heavy chain J region specific oligonucleotide:

oligo-1  5'- gga ctg tgt ccc tgt gtg atg ctt ttg atg tct ggg
gcc aag -3' (SEQ. ID NO: 12)

and the phage clone λ1.3 isolated. A 6 kb HindIII/KpnI fragment from this clone, containing all six J segments as well as D segment DHQ52 and the heavy chain J-μ intronic enhancer, was isolated. The same library was screened with the human μ specific oligonucleotide:

oligo-2  5'- cac caa gtt gac ctg cct ggt cac aga cct gac cac
cta tga -3' (SEQ. ID NO: 13)

and the phage clone λ2.1 isolated. A 10.5 kb HindIII/XhoI fragment, containing the μ switch region and all of the μ constant region exons, was isolated from this clone. These two fragments were ligated together with KpnI/XhoI digested pNNO3 to obtain the plasmid pJM1.

2. pJM2

Figure 28:
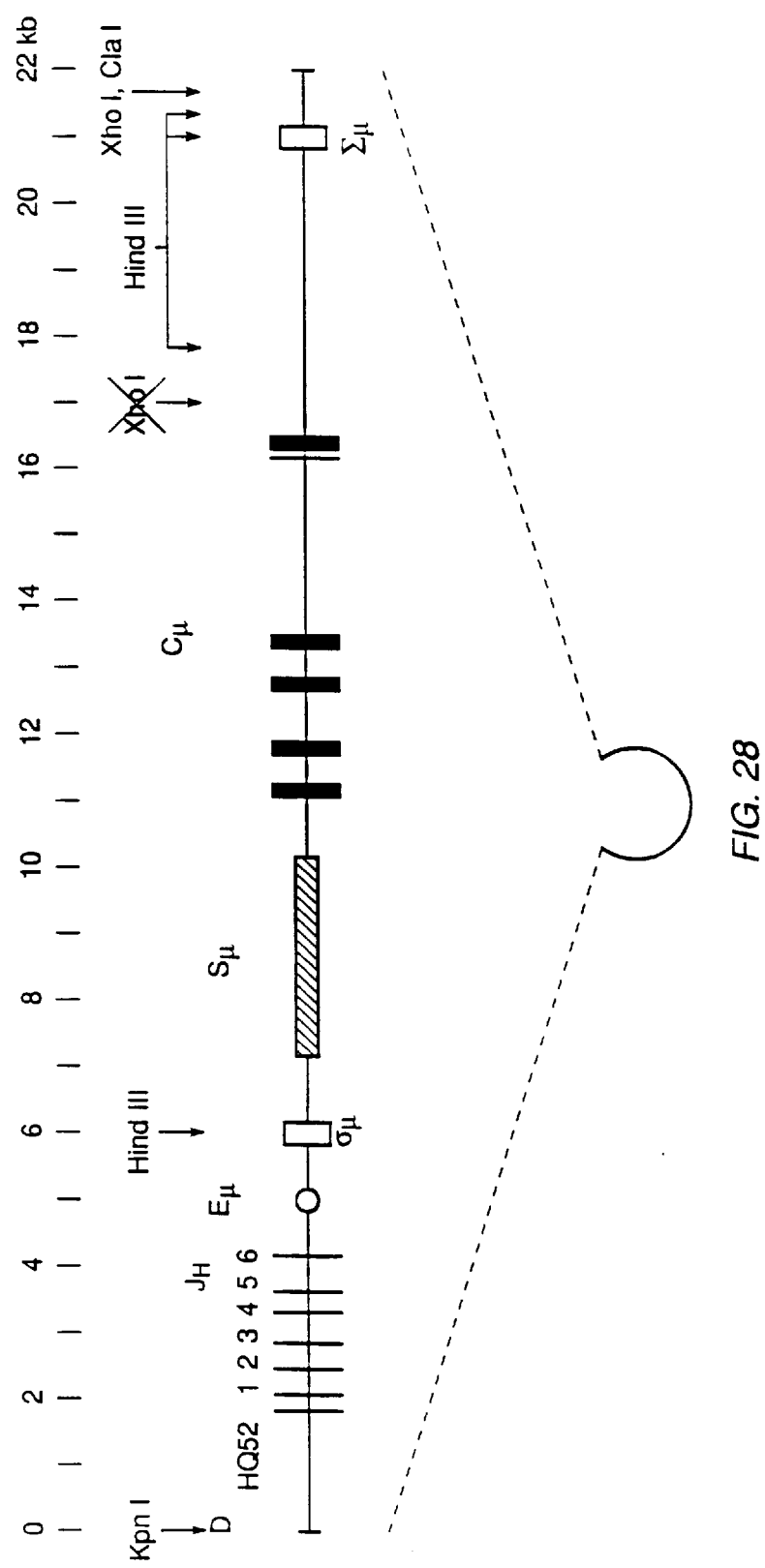
FIG. 28 depicts the structure of vector pJM2.

A 4 kb XhoI fragment was isolated from phage clone λ2.1 that contains sequences immediately downstream of the sequences in pJM1, including the so called Σμ element involved in μ deletion in certain IgD expressing B-cells (H. Yasui et al. (1989) *Eur. J. Immunol.* 19, 1399). This fragment was treated with the Klenow fragment of DNA polymerase I and ligated to XhoI cut, Klenow treated, pJM1. The resulting plasmid, pJM2 (FIG. 28), had lost the internal XhoI site but retained the 3' XhoI site due to incomplete reaction by the Klenow enzyme. pJM2 contains the entire human J region, the heavy chain J-μ intronic enhancer, the μ switch region and all of the μ constant region exons, as well as the two 0.4 kb direct repeats, σμ and Σμ, involved in μ deletion.

3. Isolation of D region clones and construction of pDH1

The following human D region specific oligonucleotide:

oligo-4  5'- tgg tat tac tat ggt tcg ggg agt tat tat aac cac agt gtc -3' (SEQ. ID NO: 16)

was used to screen the human placenta genomic library for D region clones. Phage clones λ4.1 and λ4.3 were isolated. A 5.5 kb XhoI fragment, that includes the D elements $D_{K1}$, $D_{N1}$, and $D_{M2}$ (Y. Ichihara et al. (1988) *EMBO J.*, 7, 4141), was isolated from phage clone λ4.1. An adjacent upstream 5.2 kb XhoI fragment, that includes the D elements $D_{LR1}$, $D_{XP1}$, $D_{XP'1}$, and $D_{A1}$, was isolated from phage clone λ4.3. Each of these D region XhoI fragments were cloned into the SalI site of the plasmid vector pSP72 (Promega, Madison, Wis.) so as to destroy the XhoI site linking the two sequences. The upstream fragment was then excised with XhoI and SmaI, and the downstream fragment with EcoRV and XhoI. The resulting isolated fragments were ligated together with SalI digested pSP72 to give the plasmid pDH1. pDH1 contains a 10.6 kb insert that includes at least 7 D segments and can be excised with XhoI (5') and EcoRV (3').

4. pCOR1

Figure 29:
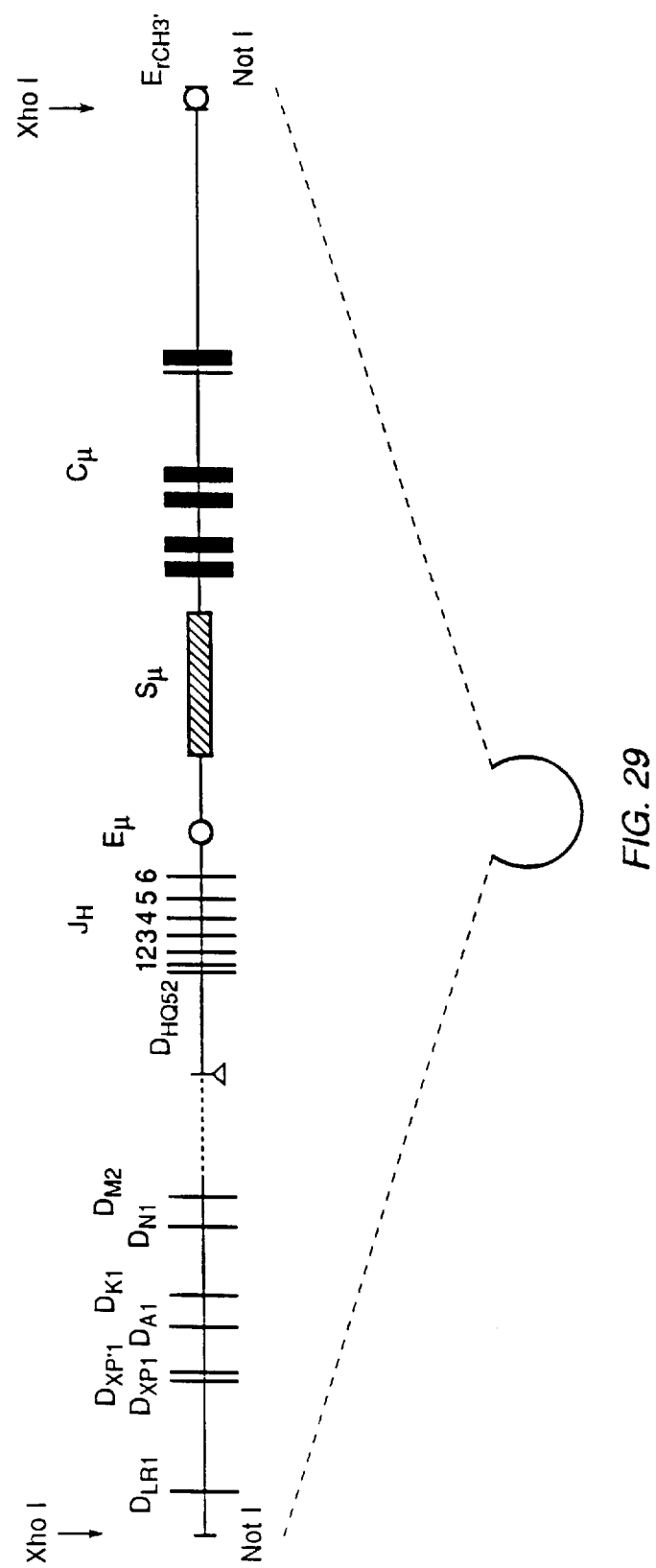
FIG. 29 depicts the structure of vector pCOR1.

The plasmid pJM2 was digested with Asp718 (an isoschizomer of KpnI) and the overhang filled in with the Klenow fragment of DNA polymerase I. The resulting DNA was then digested with ClaI and the insert isolated. This insert was ligated to the XhoI/EcoRV insert of pDH1 and XhoI/ClaI digested pGPe to generate pCOR1 (FIG. 29).

5. pVH251

A 10.3 kb genomic HindIII fragment containing the two human heavy chain variable region segments $V_H251$ and $V_H105$ (C. G. Humphries et al. (1988) *Nature* 331, 446) was subcloned into pSP72 to give the plasmid pVH251.

6. pIGM1

Figure 30:
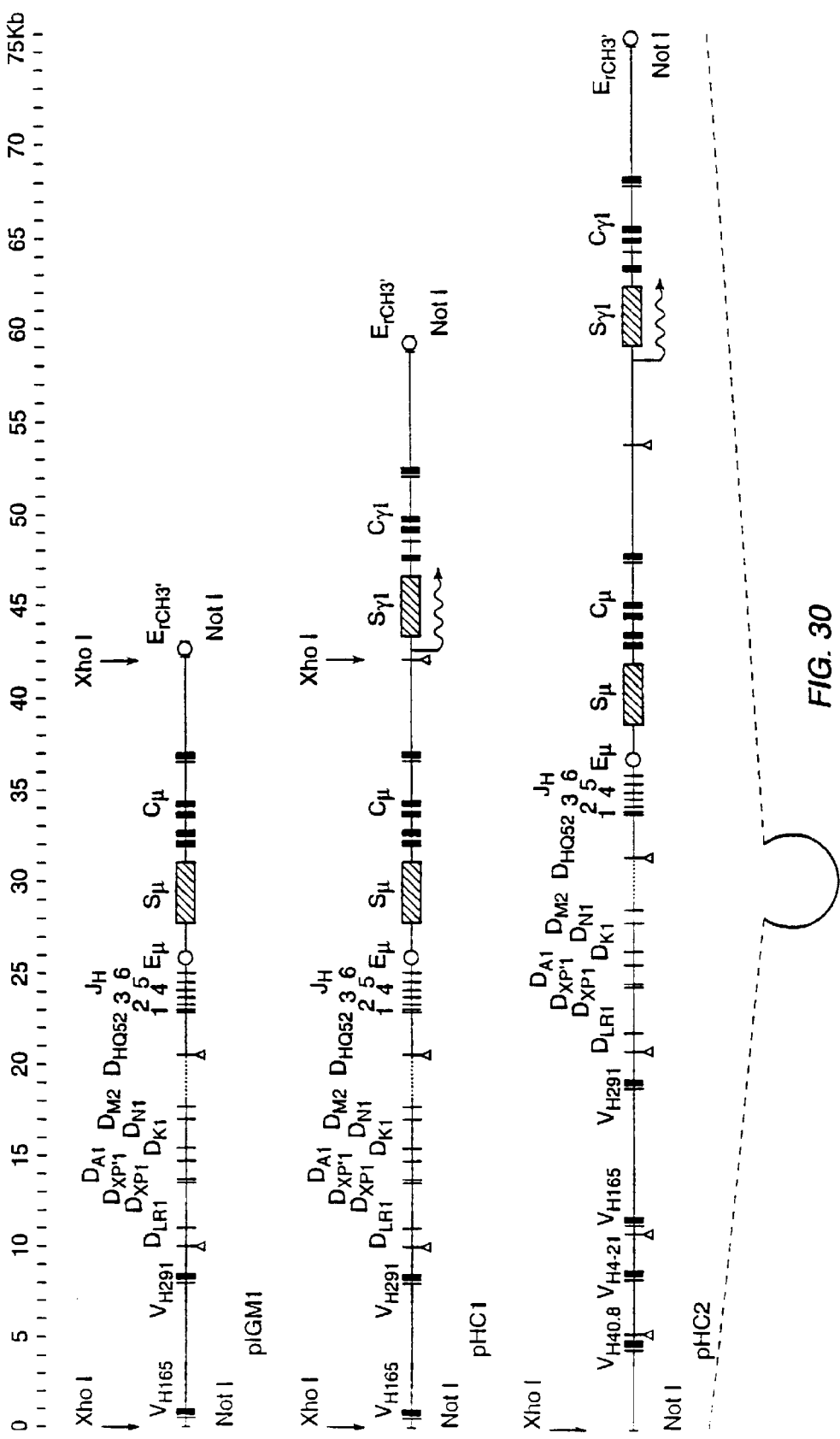
FIG. 30 depicts the transgene constructs for pIGM1, pHC1 and pHC2.

The plasmid pCOR1 was partially digested with XhoI and the isolated XhoI/SalI insert of pVH251 cloned into the upstream XhoI site to generate the plasmid pIGM1 (FIG. 30). pIGM1 contains 2 functional human variable region segments, at least 8 human D segments all 6 human $J_H$ segments, the human J-μ enhancer, the human σμ element, the human μ switch region, all of the human μ coding exons, and the human Σμ element, together with the rat heavy chain 3' enhancer, such that all of these sequence elements can be isolated on a single fragment, away from vector sequences, by digestion with NotI and microinjected into mouse embryo pronuclei to generate transgenic animals.

C. Construction of IgM and IgG expressing minilocus transgene, pHC1

1. Isolation of γ constant region clones

The following oligonucleotide, specific for human Ig g constant region genes:

oligo-29  5'- cag cag gtg cac acc caa tgc cca tga gcc cag aca ctg gac -3' (SEQ. ID NO: 50)

was used to screen the human genomic library. Phage clones 129.4 and λ29.5 were isolated. A 4 kb HindIII fragment of phage clone λ29.4, containing a γ switch region, was used to probe a human placenta genomic DNA library cloned into the phage vector lambda FIX™ II (Stratagene, La Jolla, Calif.). Phage clone λSg1.13 was isolated. To determine the subclass of the different γ clones, dideoxy sequencing reactions were carried out using subclones of each of the three phage clones as templates and the following oligonucleotide as a primer:

oligo-67  5'-tga gcc cag aca ctg gac-3' (SEQ. ID NO:51)

Phage clones λ29.5 and λSγ1.13 were both determined to be of the γ1 subclass.

2. pγe1

A 7.8 kb HindIII fragment of phage clone λ29.5, containing the γ1 coding region was cloned into pUC18. The resulting plasmid, pLT1, was digested with XhoI, Klenow treated, and religated to destroy the internal XhoI site. The resulting clone, pLT1xk, was digested with HindIII and the insert isolated and cloned into pSP72 to generate the plasmid clone pLT1xks. Digestion of pLT1xks at a polylinker XhoI site and a human sequence derived BamHI site generates a 7.6 kb fragment containing the γ1 constant region coding exons. This 7.6 kb XhoI/BamHI fragment was cloned together with an adjacent downstream 4.5 kb BamHI fragment from phage clone λ29.5 into XhoI/BamHI digested pGPe to generate the plasmid clone pλe1. pγe1 contains all of the γ1 constant region coding exons, together with 5 kb of downstream sequences, linked to the rat heavy chain 3' enhancer.

3. pγe2

Figure 31:
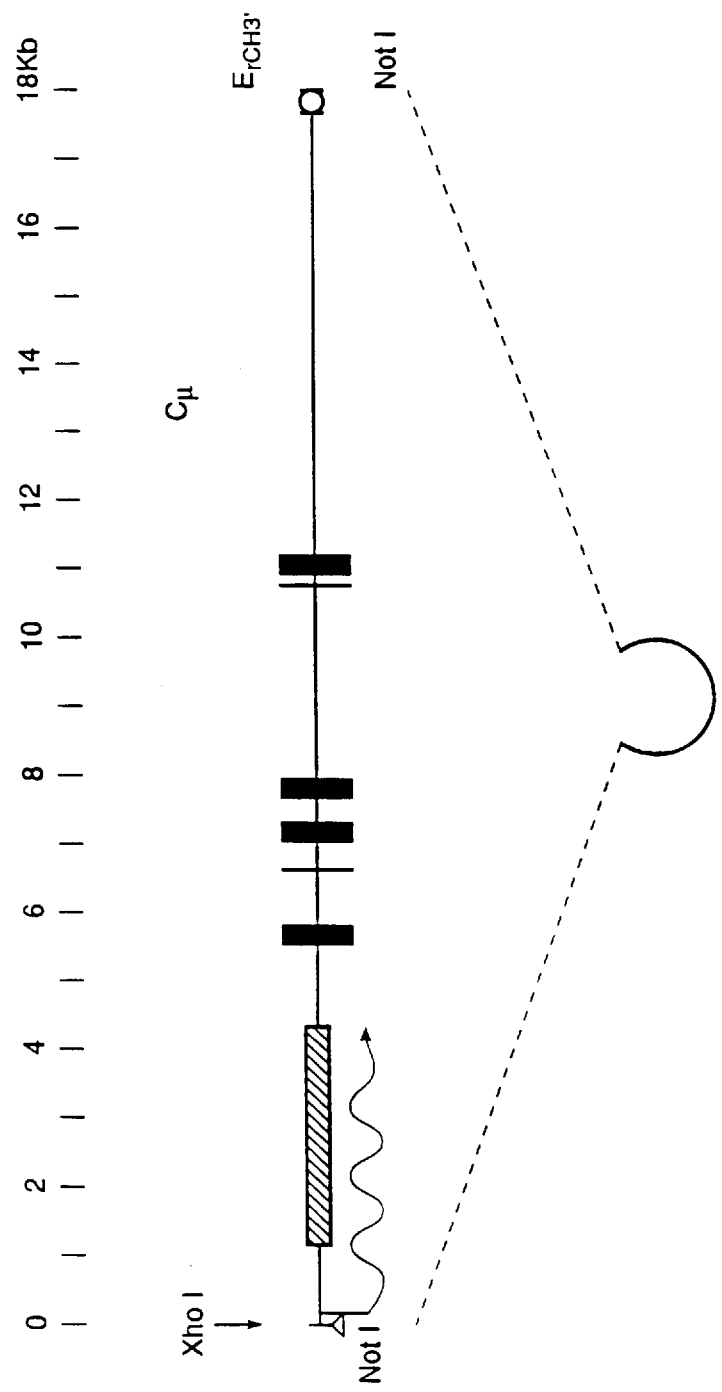
FIG. 31 depicts the structure of pγe2.

A 5.3 kb HindIII fragment containing the γ1 switch region and the first exon of the pre-switch sterile transcript (P. Sideras et al. (1989) *International Immunol.* 1, 631) was isolated from phage clone λSγ1.13 and cloned into pSP72 with the polylinker XhoI site adjacent to the 5' end of the insert, to generate the plasmid clone λSγ1s. The XhoI/SalI insert of pSγ1s was cloned into XhoI digested pγe1 to generate the plasmid clone pγe2 (FIG. 31). pγe2 contains all of the γ1 constant region coding exons, and the upstream switch region and sterile transcript exons, together with 5 kb of downstream sequences, linked to the rat heavy chain 3' enhancer. This clone contains a unique XhoI site at the 5' end of the insert. The entire insert, together with the XhoI site and the 3' rat enhancer can be excised from vector sequences by digestion with NotI.

4. pHC1

The plasmid pIGM1 was digested with XhoI and the 43 kb insert isolated and cloned into XhoI digested pge2 to generate the plasmid pHC1 (FIG. 30). pHC1 contains 2 functional human variable region segments, at least 8 human D segments all 6 human $J_H$ segments, the human J-μ enhancer, the human σμ element, the human μ switch region, all of the human μ coding exons, the human Σμ element, and the human γ1 constant region, including the associated switch region and sterile transcript associated exons, together with the rat heavy chain 3' enhancer, such that all of these sequence elements can be isolated on a single fragment, away from vector sequences, by digestion with NotI and microinjected into mouse embryo pronuclei to generate transgenic animals.

D. Construction of IgM and IgG expressing minilocus transgene, pHC2

1. Isolation of human heavy chain V region gene VH49.8

The human placental genomic DNA library lambda, FIX™ II, Stratagene, La Jolla, Calif.) was screened with the following human VH1 family specific oligonucleotide:

oligo-49  5'- gtt aaa gag gat ttt att cac ccc tgt gtc ctc tcc aca ggt gtc -3' (SEQ. ID NO: 52)

Phage clone λ49.8 was isolated and a 6.1 kb XbaI fragment containing the variable segment VH49.8 subcloned into pNNO3 (such that the polylinker ClaI site is downstream of VH49.8 and the polylinker XhoI site is upstream) to generate the plasmid pVH49.8. An 800 bp region of this insert was sequenced, and VH49.8 found to have an open reading frame and intact splicing and recombination signals, thus indicating that the gene is functional (Table 2).

TABLE 2

Sequence of human V_H I family gene V_H 49.8 (SEQ. ID NOS: 53, 54, 55)

| | | | | | |
|---|---|---|---|---|---|
| TTCCTCAGGC | AGGATTTAGG | GCTTGGTCTC | TCAGCATCCC | ACACTTGTAC | 50 |
| AGCTGATGTG | GCATCTGTGT | TTTCTTTCTC | ATCCTAGATC | AAGCTTTGAG | 100 |
| CTGTGAAATA | CCCTGCCTCA | TGAATATGCA | AATAATCTGA | GGTCTTCTGA | 150 |
| GATAAATATA | GATATATTGG | TGCCCTGAGA | GCATCACATA | ACAACCAGAT | 200 |
| TCCTCCTCTA | AAGAAGCCCC | TGGGAGCACA | GCTCATCACC | ATGGACTGGA | 250 |
| | | | | Met Asp Trp T | |
| CCTGGAGGTT | CCTCTTTGTG | GTGGCAGCAG | CTACAGgt a a | ggggcttcct | 300 |
| hr Trp Arg Ph | e Leu Phe Val | Val Ala Ala A | la Thr | | |
| agtcctaagg | ctgaggaagg | gatcctggtt | tagttaaaga | ggattttatt | 350 |
| caccoctgtg | tcctctccac | agGTGTCCAG | TCCCAGGTCC | AGCTGGTGCA | 400 |
| | | Gly Val Gln | Ser Gln Val G | ln Leu Val Gl | |
| GTCTGGGGCT | GAGGTGAAGA | AGCCTGGGTC | CTCGGTGAAG | GTCTCCTGCA | 450 |
| n Ser Gly Ala | Glu Val Lys L | ys Pro Gly Se | r Ser Val Lys | Val Ser Cys L | |
| AGGCTTCTGG | AGGCACCTTC | AGCAGCTATG | CTATCAGCTG | GGTGCGACAG | 500 |
| ys Ala Ser Gl | y Gly Thr Phe | Ser Ser Tyr A | la Ile Ser Tr | p Val Arg Gln | |
| GCCCCTGGAC | AAGGGCTTGA | GTGGATGGGA | AGGATCATCC | CTATCCTTGG | 550 |
| Ala Pro Gly G | ln Gly Leu Gl | u Trp Met Gly | Arg Ile Ile P | ro Ile Leu Gl | |
| TATAGCAAAC | TACGCACAGA | AGTTCCAGGG | CAGAGTCACG | ATTACCGCGG | 600 |
| y Ile Ala Asn | Tyr Ala Gln L | ys Phe Gln Gl | y Arg Val Thr | Ile Thr Ala A | |
| ACAAATCCAC | GAGCACAGCC | TACATGGAGC | TGAGCAGCCT | GAGATCTGAG | 650 |
| sp Lys Ser Th | r Ser Thr Ala | Tyr Met Glu L | eu Ser Ser Le | u Arg Ser Glu | |
| GACACGGCCG | TGTATTACTG | TGCGAGAGAC ACAGTG | TGAA | AACCCACATC | 700 |
| Asp Thr Ala V | al Tyr Tyr Cy | s Ala Arg | | | |
| CTGAGAGTG T CAGAAACC | CT | GAGGGAGAAG | GCAGCTGTGC | CGGGCTGAGG | 750 |
| AGAT GACAGG | GTTTATTAGG | TTTAAGGCTG | TTTACAAAAT | GGGTTATATA | 800 |
| TTTGAGAAAA | AA | | | | 812 |

2. pV2

A 4 kb XbaI genomic fragment containing the human V_HIV family gene V_H4-21 (I. Sanz et al. (1989) *EMBO J.*, 8, 3741), subcloned into the plasmid pUC12, was excised with SmaI and HindIII, and treated with the Klenow fragment of polymerase I. The blunt ended fragment was then cloned into ClaI digested, Klenow treated, pVH49.8. The resulting plasmid, pV2, contains the human heavy chain gene VH49.8 linked upstream of VH4-21 in the same orientation, with a unique SalI site at the 3' end of the insert and a unique XhoI site at the 5' end.

3. pSγ1-5'

A 0.7 kb XbaI/HindIII fragment (representing sequences immediately upstream of, and adjacent to, the 5.3 kb γ1 switch region containing fragment in the plasmid pγe2) together with the neighboring upstream 3.1 kb XbaI fragment were isolated from the phage clone λSg1.13 and cloned into HindIII/XbaI digested pUC18 vector. The resulting plasmid, pSγ1-5', contains a 3.8 kb insert representing sequences upstream of the initiation site of the sterile transcript found in B-cells prior to switching to the γ1 isotype (P. Sideras et al. (1989) *International Immunol.*, 1, 631). Because the transcript is implicated in the initiation of isotype switching, and upstream cis-acting sequences are often important for transcription regulation, these sequences are included in transgene constructs to promote correct expression of the sterile transcript and the associated switch recombination.

4. pVGE1

The pSγ1-5' insert was excised with SmaI and HindIII, treated with Klenow enzyme, and ligated with the following oligonucleotide linker:

5'-ccg gtc gac cgg-3' (SEQ. ID NO:56)

Figure 32:
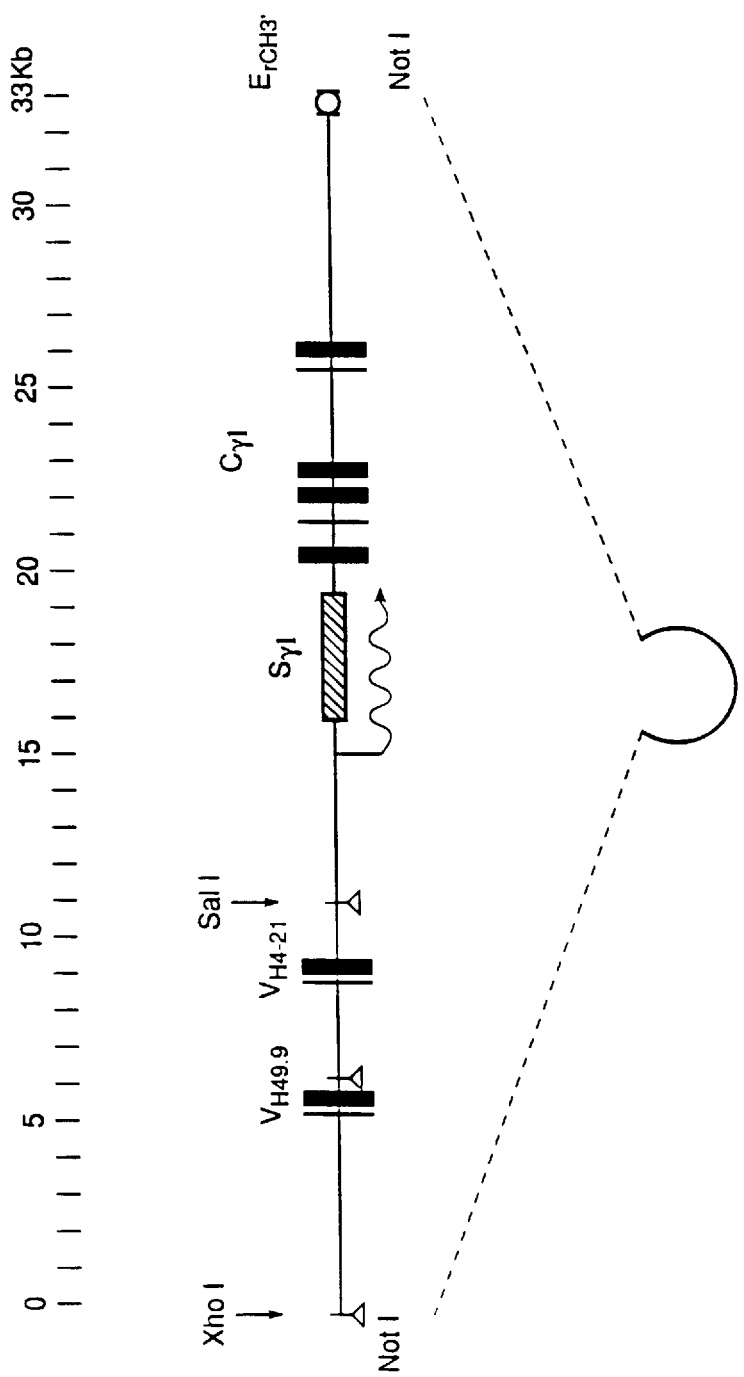
FIG. 32 depicts the structure of pVGE1.

The ligation product was digested with SalI and ligated to SalI digested pV2. The resulting plasmid, pVP, contains 3.8 kb of γ1 switch 5' flanking sequences linked downstream of the two human variable gene segments VH49.8 and VH4–21 (see Table 2). The pVP insert is isolated by partial digestion with SalI and complete digestion with XhoI, followed by purification of the 15 kb fragment on an agarose gel. The insert is then cloned into the XhoI site of pγe2 to generate the plasmid clone pVGE1 (FIG. 32). pVGE1 contains two human heavy chain variable gene segments upstream of the human γ1 constant gene and associated switch region. A unique SalI site between the variable and constant regions can be used to clone in D, J, and μ gene segments. The rat heavy chain 3' enhancer is linked to the 3' end of the γ1 gene and the entire insert is flanked by NotI sites.

5. pHC2

The plasmid clone pVGE1is digested with SalI and the XhoI insert of pIGM1 is cloned into it. The resulting clone, pHC2 (FIG. 30), contains 4 functional human variable region segments, at least 8 human D segments all 6 human J_H segments, the human J-m enhancer, the human Oμ element, the human μ switch region, all of the human μ coding exons, the human Σμ element, and the human γ1 constant region, including the associated switch region and sterile transcript associated exons, together with 4 kb flanking sequences upstream of the sterile transcript initiation site. These human sequences are linked to the rat heavy chain 3' enhancer, such that all of the sequence elements can be isolated on a single fragment, away from vector sequences, by digestion with NotI and microinjected into mouse embryo pronuclei to generate transgenic animals. A unique XhoI site at the 5' end of the insert can be used to clone in additional human variable gene segments to further expand the recombinational diversity of this heavy chain minilocus.

E. Transgenic mice

Figure 33:
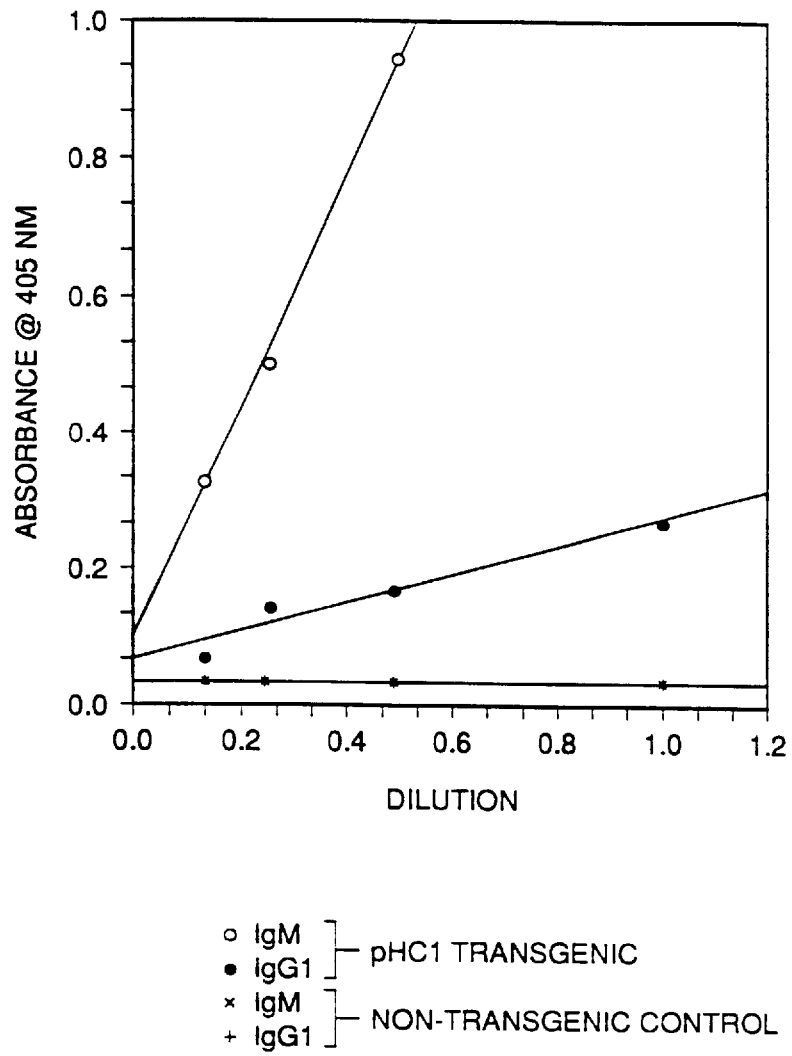
FIG. 33 depicts the assay results of human Ig expression in a pHC1 transgenic mouse.

The NotI inserts of plasmids pIGM1 and pHC1 were isolated from vector sequences by agarose gel electrophoresis. The purified inserts were microinjected into the pronuclei of fertilized (C57BL/6×CBA)F2 mouse embryos and transferred the surviving embryos into pseudopregnant females as described by Hogan et al. (B. Hogan, F. Costantini, and E. Lacy, Methods of Manipulating the Mouse Embryo, 1986, Cold Spring Harbor Laboratory, New York). Mice that developed from injected embryos were analyzed for the presence of transgene sequences by Southern blot analysis of tail DNA. Transgene copy number was estimated by band intensity relative to control standards containing known quantities of cloned DNA. At 3 to 8 weeks of age, serum was isolated from these animals and assayed for the presence of transgene encoded human IgM and IgG1 by ELISA as described by Harlow and Lane (E. Harlow and D. Lane. Antibodies: A Laboratory Manual, 1988, Cold Spring Harbor Laboratory, New York). Microtiter plate wells were coated with mouse monoclonal antibodies specific for human IgM (clone AF6, #0285, AMAC, Inc. Westbrook, Me.) and human IgG1 (clone JL512, #0280, AMAC, Inc. Westbrook, Me.). Serum samples were serially diluted into the wells and the presence of specific immunoglobulins detected with affinity isolated alkaline phosphatase conjugated goat anti-human Ig (polyvalent) that had been pre-adsorbed to minimize cross-reactivity with mouse immunoglobulins. FIG. 33 shows the results of an ELISA assay for the presence of human IgM and IgG1 in the serum of two animals that developed from embryos injected with the transgene insert of plasmid pHC1. One of the animals (#18) was negative for the transgene by Southern blot analysis, and showed no detectable levels of human IgM or IgG1. The second animal (#38) contained approximately 5 copies of the transgene, as assayed by Southern blotting, and showed detectable levels of both human IgM and IgG1. The results of ELISA assays for 11 animals that developed from transgene injected embryos is summarized in the table below (Table 3).

TABLE 3

Detection of human IgM and IgG1 in the serum of transgenic animals by ELISA assay

| animal # IgG1 | injected transgene | approximate transgene copy # (per cell) | human IgM | human |
|---|---|---|---|---|
| 6 | pIGM1 | 1 | ++ | – |
| 7 | pIGM1 | 0 | – | – |
| 9 | pIGM1 | 0 | – | – |
| 10 | pIGM1 | 0 | – | – |
| 12 | pIGM1 | 0 | – | – |
| 15 | pIGM1 | 10 | ++ | – |
| 18 | pHC1 | 0 | – | – |

TABLE 3-continued

Detection of human IgM and IgG1 in the serum of transgenic animals by ELISA assay

| animal # IgG1 | injected transgene | approximate transgene copy # (per cell) | human IgM | human |
|---|---|---|---|---|
| 19 | pHC1 | 1 | – | – |
| 21 | pHC1 | <1 | – | – |
| 26 | pHC1 | 2 | ++ | + |
| 38 | pHC1 | 5 | ++ | + |

Table 3 shows a correlation between the presence of integrated transgene DNA and the presence of transgene encoded immunoglobulins in the serum. Two of the animals that were found to contain the pHC1 transgene did not express detectable levels of human immunoglobulins. These were both low copy animals and may not have contained complete copies of the transgenes, or the animals may have been genetic mosaics (indicated by the <1 copy per cell estimated for animal #21), and the transgene containing cells may not have populated the hematopoetic lineage. Alternatively, the transgenes may have integrated into genomic locations that are not conducive to their expression. The detection of human IgM in the serum of pIGM1 transgenics, and human IgM and IgG1 in pHC1 transgenics, indicates that the transgene sequences function correctly in directing VDJ joining, transcription, and isotype switching.

EXAMPLE 15

Rearranged Heavy Chain Transgenes

A. Isolation of Rearranged Human Heavy Chain VDJ segments

Two human leukocyte genomic DNA libraries cloned into the phage vector lEMBL3/SP6/T7 (Clonetech Laboratories, Inc., Palo Alto, Calif.) are screened with a 1 kb PacI/HindIII fragment of λ1.3 containing the human heavy chain J-μ intronic enhancer. Positive clones are tested for hybridization with a mixture of the following $V_H$ specific oligonucleotides:

oligo-7  5'- tca gtg aag gtt tcc tgc aag gca tct gga tac acc ttc acc -3' (SEQ. ID NO: 57)

oligo-8  5'- tcc ctg aga ctc tcc tgt gca gcc tct gga ttc acc ttc agt -3' (SEQ. ID NO: 58)

Clones that hybridized with both V and Jμ probes are isolated and the DNA sequence of the rearranged VDJ segment determined.

B. Construction of rearranged human heavy chain transgenes Fragments containing functional VJ segments (open reading frame and splice signals) are subcloned into the plasmid vector pSP72 such that the plasmid derived XhoI site is adjacent to the 5' end of the insert sequence. A subclone containing a functional VDJ segment is digested with XhoI and PacI (PacI, a rare-cutting enzyme, recognizes a site near the J-m intronic enhancer), and the insert cloned into XhoI/PacI digested pHC2 to generate a transgene construct with a functional VDJ segment, the J-μ intronic enhancer, the μ switch element, the μ constant region coding exons, and the γ1 constant region, including the sterile transcript associated sequences, the γ1 switch, and the coding exons. This transgene construct is excised with NotI and microinjected into the pronuclei of mouse embryos to generate transgenic animals as described above.

EXAMPLE 16

Light Chain Transgenes

A. Construction of Plasmid vectors

1. Plasmid vector pGP1c

Plasmid vector pGP1a is digested with NotI and the following oligonucleotides ligated in:

oligo-81 5'-ggc cgc atc ccg ggt ctc gag gtc gac aag ctt tcg agg atc cgc-3' (SEQ. ID NO: 59)

oligo-82 5'-ggc cgc gga tcc tcg aaa gct tgt cga cct cga gac ccg gga tgc-3' (SEQ. ID NO: 60)

The resulting plasmid, pGP1c, contains a polylinker with XmaI, XhoI, SalI, HindIII, and BamHI restriction sites flanked by NotI sites.

2. Plasmid vector pGP1d

Plasmid vector pGP1a is digested with NotI and the following oligonucleotides ligated in:

oligo-87 5'-ggc cgc tgt cga caa gct tat cga tgg atc ctc gag tgc -3' (SEQ. ID NO: 61)

oligo-88 5'-ggc cgc act cga gga tcc atc gat aag ctt gtc gac agc -3' (SEQ. ID NO: 62)

The resulting plasmid, pGP1d, contains a polylinker with SalI, HindIII, ClaI, BamHI, and XhoI restriction sites flanked by NotI sites.

B. Isolation of Jκ and Cκ clones

A human placental genomic DNA library cloned into the phage vector λEMBL3/SP6/T7 (Clonetech Laboratories, Inc., Palo Alto, Calif.) was screened with the human kappa light chain J region specific oligonucleotide:

oligo-36 5'- cac ctt cgg cca agg gac acg act gga gat taa acg taa gca -3' (SEQ. ID NO: 63)

and the phage clones 136.2 and 136.5 isolated. A 7.4 kb XhoI fragment that includes the Jκ1 segment was isolated from 136.2 and subcloned into the plasmid pNNO3 to generate the plasmid clone p36.2. A neighboring 13 kb XhoI fragment that includes Jk segments 2 through 5 together with the Cκ gene segment was isolated from phage clone 136.5 and subcloned into the plasmid pNNO3 to generate the plasmid clone p36.5. Together these two clones span the region beginning 7.2 kb upstream of Jκ1 and ending 9 kb downstream of Cκ.

C. Construction of rearranged light chain transgenes 1. pCK1, a Cκ vector for expressing rearranged variable segments The 13 kb XhoI insert of plasmid clone p36.5 containing the Cκ gene, together with 9 kb of downstream sequences, is cloned into the SalI site of plasmid vector pGP1c with the 5' end of the insert adjacent to the plasmid XhoI site. The resulting clone, pCK1 can accept cloned fragments containing rearranged VJκ segments into the unique 5' XhoI site. The transgene can then be excised with NotI and purified from vector sequences by gel electrophoresis. The resulting transgene construct will contain the human J-Cκ intronic enhancer and may contain the human 3' κ enhancer.

2. pCK2, a Cκ vector with heavy chain enhancers for expressing rearranged variable segments A 0.9 kb XbaI fragment of mouse genomic DNA containing the mouse heavy chain J-µ intronic enhancer (J. Banerji et al. (1983) Cell 33, 729–740) was subcloned into pUC18 to generate the plasmid pJH22.1. This plasmid was linearized with SphI and the ends filled in with klenow enzyme. The klenow treated DNA was then digested with HindIII and a 1.4 kb MluI(klenow)/HindIII fragment of phage clone λ1.3 (previous example), containing the human heavy chain J-µ intronic enhancer (A. Hayday et al. (1984) Nature 307, 334–340), to it. The resulting plasmid, pMHE1, consists of the mouse and human heavy chain J-µ intronic enhancers ligated together into pUC18 such that they are excised on a single BamHI/HindIII fragment. This 2.3 kb fragment is isolated and cloned into pGP1c to generate pMHE2. pMHE2 is digested with SalI and the 13 kb XhoI insert of p36.5 cloned in. The resulting plasmid, pCK2, is identical to pCK1, except that the mouse and human heavy chain J-µ intronic enhancers are fused to the 3' end of the transgene insert. To modulate expression of the final transgene, analogous constructs can be generated with different enhancers, i.e. the mouse or rat 3' kappa or heavy chain enhancer (K. Meyer and M. S. Neuberger, (1989) EMBO J., 8, 1959–1964; S. Petterson, et al. (1990) Nature, 344, 165–168).

2. Isolation of rearranged kappa light chain variable segments

Two human leukocyte genomic DNA libraries cloned into the phage vector λEMBL3/SP6/T7 (Clonetech Laboratories, Inc., Palo Alto, Calif.) were screened with the human kappa light chain J region containing 3.5 kb XhoI/SmaI fragment of p36.5. Positive clones were tested for hybridization with the following Vκ specific oligonucleotide:

oligo-65 5'-agg ttc agt ggc agt ggg tct ggg aca gac ttc act ctc acc atc agc-3' (SEQ. ID NO: 64)

Clones that hybridized with both V and J probes are isolated and the DNA sequence of the rearranged VJκ segment determined.

3. Generation of transgenic mice containing rearranged human light chain constructs.

Fragments containing functional VJ segments (open reading frame and splice signals) are subcloned into the unique XhoI sites of vectors pCK1 and pCK2 to generate rearranged kappa light chain transgenes. The transgene constructs are isolated from vector sequences by digestion with NotI. Agarose gel purified insert is microinjected into mouse embryo pronuclei to generate transgenic animals. Animals expressing human kappa chain are bred with heavy chain minilocus containing transgenic animals (EXAMPLE 14) to generate mice expressing fully human antibodies.

Because not all VJκ combinations may be capable of forming stable heavy-light chain complexes with a broad spectrum of different heavy chain VDJ combinations, several different light chain transgene constructs are generated, each using a different rearranged VJk clone, and transgenic mice that result from these constructs are bred with heavy chain minilocus transgene expressing mice. Peripheral blood, spleen, and lymph node lymphocytes are isolated from double transgenic (both heavy and light chain constructs) animals, stained with fluorescent antibodies specific for human and mouse heavy and light chain immunoglobulins (Pharmingen, San Diego, Calif.) and analyzed by flow cytometry using a FACScan analyzer (Becton Dickinson, San Jose, Calif.). Rearranged light chain transgenes constructs that result in the highest level of human heavy/light chain complexes on the surface of the highest number of B cells, and do not adversely affect the immune cell compartment (as assayed by flow cytometric analysis with B and T cell subset specific antibodies), are selected for the generation of human monoclonal antibodies.

Figure 34:
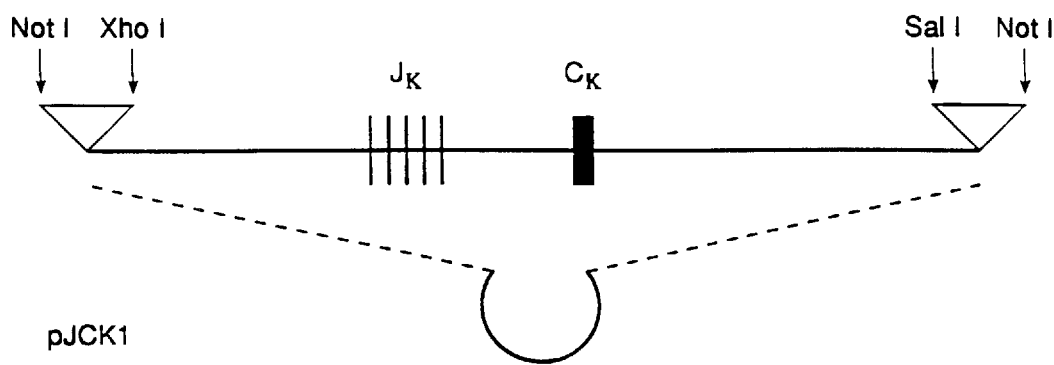
FIG. 34 depicts the structure of pJCK1.

D. Construction of unrearranged light chain minilocus transgenes 1. pJCK1, a Jκ, Cκ containing vector for constructing minilocus transgenes The 13 kb Cκ containing XhoI insert of p36.5 is treated with klenow enzyme and cloned into HindIII digested, klenow treated, plasmid pGP1d. A plasmid clone is selected such that the 5' end of the insert is adjacent to the vector derived ClaI site. The resulting plasmid, p36.5-1d, is digested with ClaI and klenow treated. The Jκ1 containing 7.4 kb XhoI insert of p36.2 is then klenow treated and cloned into the ClaI, klenow treated p36.5-1d. A clone is selected in which the p36.2 insert is in the same orientation as the p36.5 insert. This clone, pJCK1 (FIG. 34), contains the entire human Jκ region and Cκ, together with 7.2 kb of upstream sequences and 9 kb of downstream sequences. The insert also contains the human J-Cκ intronic enhancer and may contain a human 3' κ enhancer. The insert is flanked by a unique 3' SalI site for the purpose of cloning additional 3' flanking sequences such as heavy chain or light chain enhancers. A unique XhoI site is located at the 5' end of the insert for the purpose of cloning in unrearranged Vκ gene segments. The unique SalI and XhoI sites are in turn flanked by NotI sites that are used to isolate the completed transgene construct away from vector sequences.

2. Isolation of unrearranged Vκ gene segments and generation of transgenic animals expressing human Ig light chain protein The Vκ specific oligonucleotide, oligo-65 (discussed above), is used to probe a human placental genomic DNA library cloned into the phage vector lEMBL3/SP6/T7 (Clonetech Laboratories, Inc., Palo Alto, Calif.). Variable gene segments from the resulting clones are sequenced, and clones that appear functional are selected. Criteria for judging functionality include: open reading frames, intact splice acceptor and donor sequences, and intact recombination sequence. DNA fragments containing selected variable gene segments are cloned into the unique XhoI site of plasmid pJCK1 to generate minilocus constructs. The resulting clones are digested with NotI and the inserts isolated and injected into mouse embryo pronuclei to generate transgenic animals. The transgenes of these animals will undergo V to J joining in developing B-cells. Animals expressing human kappa chain are bred with heavy chain minilocus containing transgenic animals (EXAMPLE 14) to generate mice expressing fully human antibodies.

Figure 35:
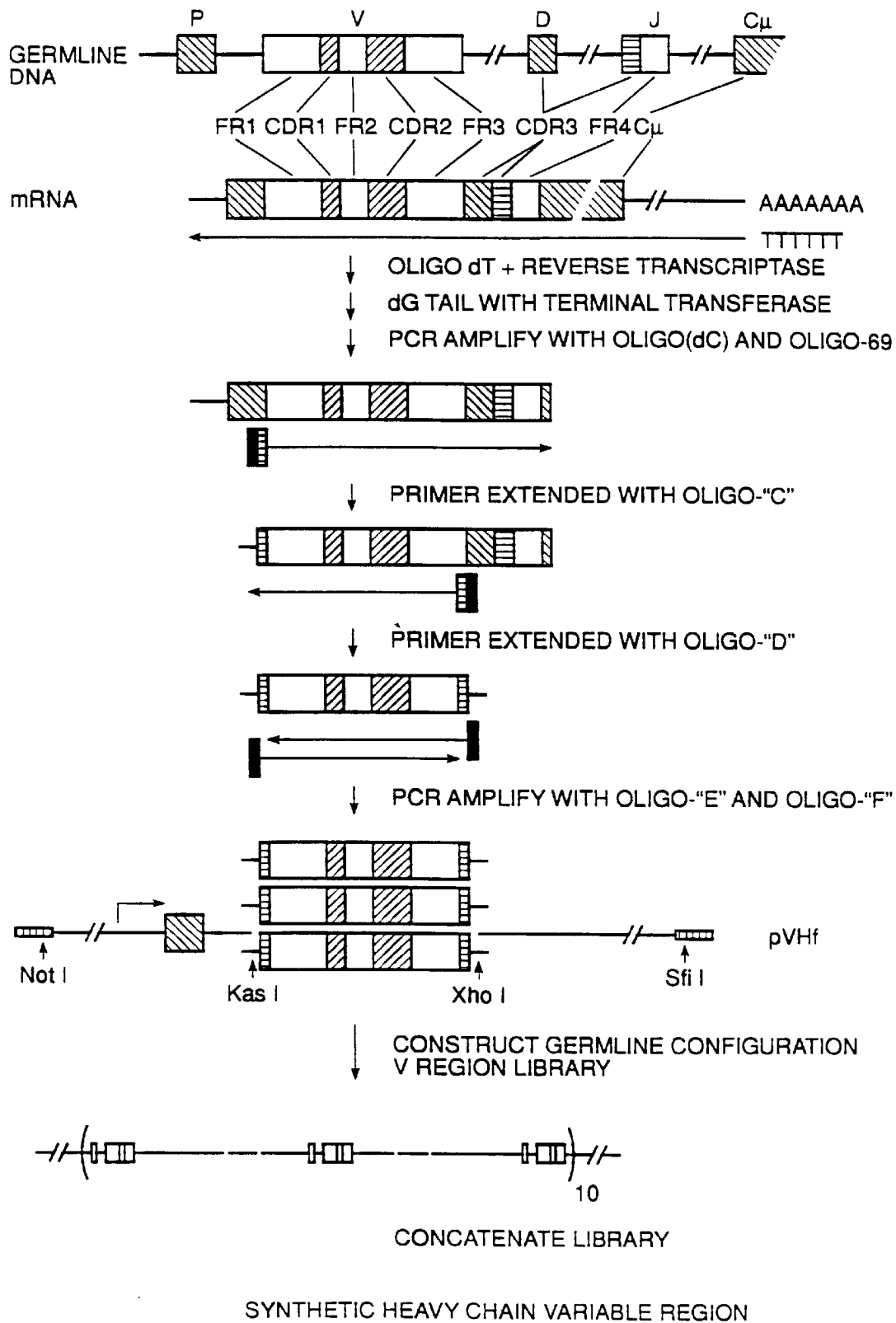
FIG. 35 depicts the construction of a synthetic heavy chain variable region.

EXAMPLE 17
Synthetic Heavy Chain Variable Region
This example is outlined in FIG. 35.
A. Construction of Cloning Vector pVHf
1. pGP1f The plasmid pGP1a (previous example) is digested with NotI and the following oligonucleotides are ligated to it:
oligo-"a"5'-ggc cgc atg cta ctc gag tgc aag ctt ggc cat cca-3' (SEQ. ID NO:65)
oligo-"b"5'-ggc ctg gat ggc caa gct tgc act cga gta gca tgc-3' (SEQ. ID NO:66)

The resulting plasmid, pGP1f, contains SphI, XhoI, and HindIII sites flanked by NotI and SfiI sites.
2. pVHf The human V$_H$-V family variable gene segment V$_H$251 (C. G. Humphries et al. (1988) *Nature*, 331, 446) together with approximately 2.4 kb of 5' flanking sequences and approximately 1.4 kb of 3' flanking sequences was isolated on a 4.2 kb SphI/HindIII fragment from the plasmid clone pVH251 (previous example) and cloned into the plasmid vector pSelect™-1 (Promega Corp., Madison, Wis.). The 5' flanking sequences, together with the promoter, first exon and first intron of V$_H$251, are amplified by polymerase chain reaction (PCR) from this template using the following oligonucleotides:

oligo-83 5'-cag ctc gag ctc ggc aca ggc gcc tgt ggg-3' (SEQ. ID NO:67)
oligo-84 5'-ctc tag agt cga cct gca ggc-3' (SEQ. ID NO:68)
The 3' flanking sequences are amplified by PCR using the following oligonucleotides:
oligo-85 5'-agc ctc gag ccc gtc taa aac cct cca cac-3' (SEQ. ID NO:69)
oligo-86 5'-ggt gac act ata gaa tac tca agc-3' (SEQ. ID NO: 70)

The amplified 5' sequences are digested with SphI and XhoI, and the 3' sequences digested with HindIII and XhoI. The resulting fragments are cloned together into the plasmid pGP1f to generate plasmid pVHf. Plasmid pVHf contains the cis acting regulatory elements that control transcription of V$_H$251, together with the signal sequence encoding first exon. pVHf is used as an expression cassette for heavy chain variable sequences. Such sequences are cloned into the KasI/XhoI digested plasmid as described below.

B. Isolation of Variable Gene Coding Sequences
1. Amplification of expressed V$_H$ gene cDNA sequences Poly(A)$^+$ RNA is isolated from human peripheral blood lymphocytes (PBL). First strand cDNA is synthesized with reverse transcriptase, using oligo-(dT) as a primer. The first strand cDNA is isolated and tailed with oligo (dG) using terminal transferase. The 5' sequences of IgM transcripts are then specifically amplified by a modification of the method of Frohman et al. (1988, *Proc. Natl. Acad. Sci. USA*, 85, 8998). Oligo-(dC)$_{13}$ and the following oligonucleotide:
oligo-69 5'-gga att ctc aca gga gac gag-3' (SEQ. ID NO:71)
are used as 5' and 3' primers, respectively, in a polymerase chain reaction with dG-tailed first strand PBL cDNA. Oligo-69 is complimentary to sequences encoding amino acids 11–17 of the IgM constant domain. Therefore these primers will amplify DNA fragments of approximately 0.6 kb that include expressed V$_H$ gene sequences.

2. Back-conversion of cDNA sequences into germline form
The following oligonucleotide:

oligo-"c" 5'-ctg acg act ctg tat ggc gcc (ct)a(cg) t(cg)(ct)
(cg)ag (ag)t(cg) ca(ag) ct(gt) gtg (cg)a(ag) tc(gt)
gg(gt)-3' (SEQ. ID NO: 72)

is annealed to denatured, PCR amplified, IgM 5' sequences. Oligo-"c" includes a 21 nucleotide nondegenerate sequence that includes a KasI site, followed by a 30 nucleotide degenerate sequence that is homologous to the 5' end of the second exon of many human V$_H$ segments (Genbank; Los Alamos, N. Mex.). The primer is extended with DNA polymerase and the product isolated from unused primer by size fractionation. The product is then denatured and annealed to the following oligonucleotide:

oligo-"d" 5'-ggg ctc gag gct ggt ttc tct cac tgt gtg t(cgt)t
(acgt) (ag) (ct) aca gta ata ca(ct) (ag)g(ct)-3' (SEQ. ID NO: 73)

oligo-"d" includes a 30 nucleotide nondegenerate sequence that includes an XhoI site and part of the V to DJ recombination sequence, followed by a 21 nucleotide degenerate sequence that is complimentary to the sequence encoding the last seven amino acids in framework region three of many human variable gene segments. The annealed oligonucleotide is then extended with DNA polymerase and the product isolated from unused primer by size fractionation. Single rounds of DNA synthesis followed by removal of primers are carried out to ensure the sequence integrity of individual variable gene fragments. The product of oligo- "d" primer extension is amplified by PCR using the following two oligonucleotides as primers:

oligo-"e"5'-ctg acg act ctg tat ggc gcc-3' (SEQ. ID NO: 74)

oligo-"f"5'-ggg ctc gag gct ggt ttc tct-3' (SEQ. ID NO: 75)

The resulting 0.36 kb PCR product is purified by gel electrophoresis and digested with the restriction enzymes KasI and XhoI. Digestion products are then cloned into KasI/XhoI digested pVHf to generate a library of expressed variable gene sequences in germline configuration. Ligation into the KasI site of pVHf recreates the splice acceptor site at the 5' end of the second exon, while ligation into the XhoI site recreates the recombination signal at the 3' end of the variable gene segment. Alternative versions of degenerate oligonucleotides "c" and "d" are used to amplify different populations of variable genes, and generate germline-configuration libraries representing those different populations (Genbank; Los Alamos, N. Mex.).

C. Construction of Synthetic Locus

The entire library of synthetic germline-configuration $V_H$ genes is grown up together and plasmid DNA isolated. The medium copy plasmid pVHf, which includes a strong transcription terminator between the ampicillin resistance gene and the cloning site, is designed to minimize the expansion of particular clones within the library. Plasmid DNA is digested with SfiI, treated with calf intestinal phosphatase to remove 5' phosphate groups, and then digested with NotI. The calf intestinal phosphatase is removed prior to NotI digestion so that only the SfiI ends are dephosphorylated. The digested DNA is then isolated from vector sequences by agarose gel electrophoresis and ligated to the following oligonucleotides:

oligo-"g"5'-ggc cta act gag cgt ccc ata ttg aga acc tcc -3' (SEQ. ID NO: 76)

oligo-"h"5'-ggt tct caa tat ggg acg ctc agt ta-3' (SEQ. ID NO: 77)

Oligo-"h" is kinased while oligo-"g" is left unphosphorylated. The ligation reaction is carried out with a large molar excess of oligonucleotides so that all of the V gene fragment NotI ends will be ligated to oligonucleotides and not other V region fragments. Because the SfiI ends are not self compatible, the V segments will concatenate in the same orientation such that each V segment is separated by a single oligonucleotide spacer unit from the next V segment.

Large concatomers are sized by electrophoresis and isolated from agarose gels. The size fractionated concatomers are then directly coinjected into mouse embryo pronuclei together with D-J-C containing DNA fragments (such as the pHC1 or pHC2 inserts) to generate transgenic animals with large primary repertoires. Alternatively, the concatomers are cloned into a plasmid vector such as pGPf.

EXAMPLE 18

Generation of Lymphoid Cell Receptor Subset Specific Antibodies

The inoculation of mice with xenogeneic (i.e. human) immunoglobulins (B-cell receptors) or T-cell receptors leads predominantly to the generation of mouse antibodies directed against particular epitopes (dominant epitopes) that shared by all or most immunoglobulins or T-cell receptors of a given species, but differ between species. It is therefore difficult to isolate antibodies that distinguish particular subsets of B or T cell receptors (e.g., idiotypes or variable region families). However, the transgenic mouse expressing human immunoglobulins (described in the above examples) will be immunologically tolerant of those shared B-cell epitopes and will therefore be useful for generating antibodies that distinguish subsets of human immunoglobulins. This concept is extended by generating transgenic mice expressing human T-cell receptor coding sequences and breeding these mice with the human immunoglobulin transgenic mice. Such mice are inoculated with isolates containing human T-cell receptor proteins and monoclonal antibodies are generated that recognize T-cell receptor subsets.

Studies have demonstrated that there is a limited variability of T cell antigen receptors involved in certain autoimmune diseases (T. F. Davies et al. (1991) *New England J. Med.*, 325, 238). Because of this limited variability, it is possible to generate human monoclonal antibodies that specifically recognize that subset of human T cells which is auto-reactive.

A. Generation of B-cell subset specific antibodies

Human immunoglobulin expressing transgenic mice are inoculated with immunoglobulins isolated from a healthy donor or from a patient with a B-cell malignancy expressing a high level of a single immunoglobulin type (Miller et al. (1982) New Eng. J. Med. 306, 517–522). Monoclonal antibody secreting hybridomas are generated as described by Harlow and Lane (E. Harlow and D. Lane. Antibodies: A Laboratory Manual. 1988. Cold Spring Harbor Laboratory, New York). Individual hybridomas that secrete human antibodies that specifically recognize B-cell subsets are selected.

B. Transgenic mice expressing human T-cell receptor sequences

DNA fragments-containing intact and fully rearranged human T-cell receptor (TCR) α and β genes are coinjected into mouse embryo pronuclei to generate transgenic animals. Transgenic animals are assayed by FACS analysis for the expression of both transgenes on the surface of their T-cells. Animals are selected that express only low levels of the human α and β TCR chains on a fraction of their T-cells. Only low level expression is required to obtain immunological tolerance, and high level expression will disturb the animal's immune system and interfere with the ability to mount an immune response required for the generation monoclonal antibodies. Alternatively, because correct tissue or cell type specific expression is not required to obtain immunologic tolerance, TCR α and β chain cDNA clones are inserted into transgene expression cassettes (T. Choi et al. (1991) *Mol. Cell. Biol.*, 11, 3070–3074) under the control of non-TCR transcription signals. TCR α and β chain cDNA transgene constructs are coinjected into mouse embryo pronuclei to generate transgenic animals. Ectopic expression of the TCR chains will not result in cell surface expression because the TCR is a multichain complex (H. Clevers et al. 1988 *Ann. Rev. Immunol.*, 6, 629–662); however, cell surface expression is not required for antigen presentation (Townsend et al. (1986) *Nature*, 324, 575–577) and tolerance induction.

T-cell receptor a and a chain transgenic mice are bred with human immunoglobulin expressing transgenic mice to generate mice that are useful for generating human monoclonal antibodies that recognize specific subsets of human T-cells. Such mice are inoculated with T-cell derived proteins isolated from a healthy donor or from a patient with a T-cell malignancy expressing a single TCR type. Monoclonal antibody secreting hybridomas are generated and individual hybridomas that secrete human antibodies that specifically recognize B-cell subsets are selected.

EXAMPLE 19

Genomic Heavy Chain Human Ig Transgene

This Example describes the cloning of a human genomic heavy chain immunoglobulin transgene which is then introduced into the murine germline via microinjection into zygotes or integration in ES cells.

Nuclei are isolated from fresh human placental tissue as described by Marzluff, W. F., et al. (1985), *Transcription and Translation: A Practical Approach*, B. D. Hammes and S. J. Higgins, eds., pp. 89–129, IRL Press, Oxford). The isolated nuclei (or PBS washed human spermatocytes) are embedded in 0.5% low melting point agarose blocks and lysed with 1 mg/ml proteinase K in 500 mM EDTA, 1% SDS for nuclei, or with 1 mg/ml proteinase K in 500 mM EDTA, 1% SDS, 10 mM DTT for spermatocytes at 50° C. for 18 hours. The proteinase K is inactivated by incubating the blocks in 40 μg/ml PMSF in TE for 30 minutes at 50° C., and then washing extensively with TE. The DNA is then digested in the agarose with the restriction enzyme NotI as described by M. Finney in *Current Protocols in Molecular Biology* (F. Ausubel et al., eds. John Wiley & Sons, Supp. 4, 1988, e.g., Section 2.5.1).

The NotI digested DNA is then fractionated by pulsed field gel electrophoresis as described by Anand, R. et al. (1989), *Nuc. Acids Res.*, 17, 3425–3433.Fractions enriched for the NotI fragment are assayed by Southern hybridization to detect one or more of the sequences encoded by this fragment. Such sequences include the heavy chain D segments, J segments, and γ1constant regions together with representatives of all 6 $V_H$ families (although this fragment is identified as 670 kb fragment from HeLa cells by Berman et al. (1988), supra., we have found it to be an 830 kb fragment from human placental and sperm DNA). Those fractions containing this NotI fragment (see FIG. 4) are ligated into the NotI cloning site of the vector pYACNN as described (McCormick, M. et al. (1990), *Technique* 2, 65–71). Plasmid pYACNN is prepared by digestion of pYACneo (Clontech) with EcoRI and ligation in the presence of the oligonucleotide 5'-AAT TGC GGC CGC-3'.

YAC clones containing the heavy chain NotI fragment are isolated as described by Traver et al. (1989), *Proc. Natl. Acad. Sci. USA*, 86, 5898–5902. The cloned NotI insert is isolated from high molecular weight yeast DNA by pulse field gel electrophoresis as described by M. Finney, op. cit. The DNA is condensed by the addition of 1 mM spermine and microinjected directly into the nucleus of single cell embryos previously described. Alternatively, the DNA is isolated by pulsed field gel electrophoresis and introduced into ES cells by lipofection (Gnirke et al. (1991), *EMBO J.*, 10, 1629–1634), or the YAC is introduced into ES cells by spheroplast fusion.

EXAMPLE 20

Discontinuous Genomic Heavy Chain Ig Transgene

An 85 kb SpeI fragment of human genomic DNA, containing $V_H6$, D segments, J segments, the μ constant region and part of the γ constant region (see FIG. 4), has been isolated by YAC cloning essentially as described in Example 1. A YAC carrying a fragment from the germline variable region, such as a 570 kb NotI fragment upstream of the 670–830 kb NotI fragment described above containing multiple copies of $V_1$ through $V_5$ is isolated as described. (Berman et al. (1988), supra. detected two 570 kb NotI fragments, each containing multiple V segments.) The two fragments are coinjected into the nucleus of a mouse single cell embryo as described in Example 1.

Typically, coinjection of two different DNA fragments result in the integration of both fragments at the same insertion site within the chromosome. Therefore, approximately 50% of the resulting transgenic animals that contain at least one copy of each of the two fragments will have the V segment fragment inserted upstream of the constant region containing fragment. Of these animals, about 50% will carry out V to DJ joining by DNA inversion and about 50% by deletion, depending on the orientation of the 570 kb NotI fragment relative to the position of the 85 kb SpeI fragment. DNA is isolated from resultant transgenic animals and those animals found to be containing both transgenes by Southern blot hybridization (specifically, those animals containing both multiple human V segments and human constant region genes) are tested for their ability to express human immunoglobulin molecules in accordance with standard techniques.

EXAMPLE 21

Joining Overlapping YAC Fragments

Two YACs carrying a region of overlap are joined in yeast by meiotic recombination as described by Silverman et al. (1990), *Proc. Natl. Acad. Sci. USA*, 87, 9913–9917, to derive a single, large YAC carrying sequences from both smaller YACs. The two YACs are aligned with respect to the arms, such that the joined YAC will contain one centromeric vector arm and one non-centromeric vector arm. If necessary, the insert is recloned in the vector using unique restriction sites at the ends of the insert. If the insert is not a unique restriction fragment, unique sites are inserted into the vector arms by oligonucleotide transformation of yeast, as described by Guthrie and Fink, op. cit. To join YACs carrying noncontiguous sequences which do not overlap, an overlap is created as follows. The 3' terminal region of the 5' YAC and the 5' terminal region of the 3' YAC are subcloned, joined in vitro to create a junction fragment, and reintroduced into one or both YACs by homologous recombination (Guthrie and Fink, op cit). The two YACs are then meiotically recombined as described by Silverman et al., op cit). The joined YAC is introduced into mice, e.g., as in Example 1.

EXAMPLE 22

Genomic κ Light Chain Human Ig Transgene

A map of the human κ light chain has been described in Lorenz, W. et al. (1987), *Nucl. Acids Res.*, 15, 9667–9677 and is depicted in FIG. 11. A 450 kb XhoI to NotI fragment that includes all of Cκ, the 3' enhancer, all J segments, and at least five different V segments (a), or a 750 kb MluI to NotI fragment that includes all of the above plus at least 20 more V segments (b) is isolated and introduced into zygotes or ES cells as described in Example 1.

EXAMPLE 23

Genomic κ Light Chain Human Ig Transgene Formed by In Vivo Homologous Recombination The 750 kb MluI to NotI fragment is digested with BssHII to produce a fragment of about 400 kb (c). The 450 kb XhoI to NotI fragment (a) plus the approximately 400 kb MluI to BssHII fragment (c) have sequence overlap defined by the BssHII and XhoI restriction sites shown in FIG. 11. Homologous recombination of these two fragments upon microinjection of a mouse zygote results in a transgene containing at least an additional 15–20 V segments over that found in the 450 kb XhoI/NotI fragment (Example 22).

EXAMPLE 24

Identification of functionally rearranged variable region sequences in transgenic B cells An antigen of interest is used to immunize (see Harlow and Lane, *Antibodies: A Laboratory Manual*, Cold Spring Harbor, N.Y. (1988)) a mouse with the following genetic traits: homozygosity at the endogenous having chain locus for a deletion of $J_H$ (Examples 9 and 12), hemizygous for a single copy of unrearranged human heavy chain minilocus transgene (examples 5 and 14); and hemizygous for a single copy of a rearranged human kappa light chain transgene (Examples 7 and 16).

Following the schedule of immunization, the spleen is removed, and spleen cells used to generate hybridomas. Cells from an individual hybridoma clone that secretes antibodies reactive with the antigen of interest are used to prepare genomic DNA. A sample of the genomic DNA is digested with several different restriction enzymes that recognize unique six base pair sequences, and fractionated on an agarose gel. Southern blot hybridization is used to identify two DNA fragments in the 2–10 kb range, one of which contains the single copy of the rearranged human heavy chain VDJ sequences and one of which contains the single copy of the rearranged human light chain VJ sequence. These two fragments are size fractionated on agarose gel and cloned directly into pUC18. The cloned inserts are then subcloned respectively into heavy and light chain expression cassettes that contain constant region sequences.

The plasmid clone pγe1 (Example 14) is used as a heavy chain expression cassette and rearranged VDJ sequences are cloned into the XhoI site. The plasmid clone pCK1 is used as a light chain expression cassette and rearranged VJ sequences are cloned into the XhoI site. The resulting clones are used together to transfect $SP_0$ cells to produce antibodies that react with the antigen of interest (M.S. Co. et al. (1991) *Proc. Natl. Acad. Sci.* U.S.A. 88:2869).

Alternatively, mRNA is isolated from the cloned hybridoma cells described above, and used to synthesize cDNA. The expressed human heavy and light chain VDJ and VJ sequence are then amplified by PCR and cloned (J. W. Larrich et al. (1989) *Biol. Technology,* 7:934–938). After the nucleotide sequence of these clones has been determined, oligonucleotides are synthesized that encode the same polypeptides, and synthetic expression vectors generated as described by C. Queen et al. (1989) *Proc. Natl. Acad. Sci. USA.,* 84:5454–5458.

The foregoing description of the preferred embodiments of the present invention has been presented for purposes of illustration and description. They are not intended to be exhaustive or to limit the invention to the precise form disclosed, and many modifications and variations are possible in light of the above teaching.

All publications and patent applications herein are incorporated by reference to the same extent as if each individual publication or patent application was specifically and individually indicated to be incorporated by reference.

Such modifications and variations which may be apparent to a person skilled in the art are intended to be within the scope of this invention.

---

What is claimed is:

1. A transgene comprising, in operable linkage for expression of human immunoglobulin heavy chains, a plurality of human heavy chain VH gene segments, a plurality of human heavy chain D gene segments, a plurality of human heavy chain J gene segments, a mu constant region comprised of a mu switch region located upstream from a mu coding segment, and a gamma constant region comprised of a gamma switch region located upstream from a human gamma coding segment, wherein the gamma constant region is in closer proximity to the mu constant region than in a naturally occurring human immunoglobulin heavy chain gene locus.

2. A transgene comprising, in operable linkage for expression of human immunoglobulin heavy chains, a plurality of human VH gene segments, a plurality of human D gene segments, a plurality of human JH gene segments, an immunoglobulin heavy chain enhancer, a mu constant region comprised of a mu switch region located upstream from a mu constant gene segment, a gamma constant region comprised of a gamma switch region located upstream from a human gamma constant gene segment, wherein said transgene has at least one discontinuity of at least 2 kb between said mu and gamma gene segments as compared to a human germline heavy chain locus.

3. The transgene of claim 2, wherein the gamma switch region comprises an approximately 5.3 kb HindIII fragment.

4. The transgene of claim 2, wherein the gamma switch region comprises an approximately 4 kb HindIII fragment.

5. A transgene comprising in operable linkage a plurality of human VH gene segments, a plurality of human D gene segments, a plurality of human JH gene segments, a human mu CH gene, at least two different non-mu human CH genes and associated isotype switching sequences, wherein human mu and human gamma switch sequences are located in closer proximity to each other than in a naturally occurring human immunoglobulin locus.

6. The transgene of claim 5, wherein the gamma switch sequences are contained within an approximately 5.3 kb HindIII fragment.

7. The transgene of claim 5, wherein the gamma switch sequences are contained within an approximately 4 kb HindIII fragment.

* * * * *

SEQUENCE LISTING ( 1 ) GENERAL INFORMATION:

( i i i ) NUMBER OF SEQUENCES: 77

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
A A T T G C G G C C   G C                                                                                          1 2
```

( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
C T T G A G C C C G   C C T A A T G A G C   G G G C T T T T T T   T T G C A T A C T G   C G G C C              4 5
```

( 2 ) INFORMATION FOR SEQ ID NO:3:

( i ) SEQUENCE CHARACTERISTICS:

(A) LENGTH: 51 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

GCAATGGCCT GGATCCATGG CGCGCTAGCA TCGATATCTA GAGCTCGAGC A     51

(2) INFORMATION FOR SEQ ID NO:4:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

TGCAGATCTG AATTCCCGGG TACCAAGCTT ACGCGTACTA GTGCGGCCGC T     51

(2) INFORMATION FOR SEQ ID NO:5:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

AATTAGCGGC CGCACTAGTA CGCGTAAGCT TGGTACCCGG GAATT     45

(2) INFORMATION FOR SEQ ID NO:6:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

CAGATCTGCA TGCTCGAGCT CTAGATATCG ATGCTAGCGC GCCATGGATC C     51

(2) INFORMATION FOR SEQ ID NO:7:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

AGGCCATTGC GGCCGCAGTA TGCAAAAAAA AGCCCGCTCA TTAGGCGGGC T     51

(2) INFORMATION FOR SEQ ID NO:8:

(i) SEQUENCE CHARACTERISTICS:
(A) LENGTH: 19 base pairs
(B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:8:

CGCGTGGCCG CAATGGCCA                                                                                    19

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CTAGTGGCCA TTGCGGCCA                                                                                    19

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CAGGATCCAG ATATCAGTAC CTGAAACAGG GCTTGC                                                                  36

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GAGCATGCAC AGGACCTGGA GCACACACAG CCTTCC                                                                  36

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGACTGTGTC CCTGTGTGAT GCTTTTGATG TCTGGGGCCA AG                                                           42

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CACCAAGTTG ACCTGCCTGG TCACAGACCT GACCACCTAT GA                                                           42

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCTGTGGACC ACCGCCTCCA CCTTCATCGT CCTCTTCCTC CT     42

( 2 ) INFORMATION FOR SEQ ID NO:15:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TGAGCCACGA AGACCCTGAG GTCAAGTTCA ACTGGTACGT GG     42

( 2 ) INFORMATION FOR SEQ ID NO:16:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TGGTATTACT ATGGTTCGGG GAGTTATTAT AACCACAGTG TC     42

( 2 ) INFORMATION FOR SEQ ID NO:17:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GCCTGAAATG GAGCCTCAGG GCACAGTGGG CACGGACACT GT     42

( 2 ) INFORMATION FOR SEQ ID NO:18:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GCAGGGAGGA CATGTTTAGG ATCTGAGGCC GCACCTGACA CC     42

( 2 ) INFORMATION FOR SEQ ID NO:19:

( i ) SEQUENCE CHARACTERISTICS:

( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

GATCCTGGTT TAGTTAAAGA GGATTTTATT CACCCCTGTG TC  42

( 2 ) INFORMATION FOR SEQ ID NO:20:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

GATCCAAGCA GT  12

( 2 ) INFORMATION FOR SEQ ID NO:21:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

CTAGACTGCT TG  12

( 2 ) INFORMATION FOR SEQ ID NO:22:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

CGCGTCGAAC TA  12

( 2 ) INFORMATION FOR SEQ ID NO:23:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

AGCTTAGTTC GA  12

( 2 ) INFORMATION FOR SEQ ID NO:24:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

GAATGGGAGT GAGGCTCTCT CATACCCTAT TCAGAACTGA CT  42

( 2 ) INFORMATION FOR SEQ ID NO:25:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GAACTGTGGC TGCACCATCT GTCTTCATCT TCCCGCCATC TG  42

( 2 ) INFORMATION FOR SEQ ID NO:26:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GAGGTACACT GACATACTGG CATGCCCCCC CCCCCC  36

( 2 ) INFORMATION FOR SEQ ID NO:27:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GTACGCCATA TCAGCTGGAT GAAGTCATCA GATGGCGGGA AGATGAAGAC AGATGGTGCA  60

( 2 ) INFORMATION FOR SEQ ID NO:28:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

TCATCAGATG GCGGGAAGAT GAAGACAGAT GGTGCA  36

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GTACGCCATA TCAGCTGGAT GAAG  24

( 2 ) INFORMATION FOR SEQ ID NO:30:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:30:

GAGGTACACT GACATACTGG CATG                                    24

( 2 ) INFORMATION FOR SEQ ID NO:31:

( i ) SEQUENCE CHARACTERISTICS:
      ( A ) LENGTH: 60 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:31:

GTACGCCATA TCAGCTGGAT GAAGACAGGA GACGAGGGGG AAAAGGGTTG GGGCGGATGC       60

( 2 ) INFORMATION FOR SEQ ID NO:32:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:32:

ACAGGAGACG AGGGGGAAAA GGGTTGGGGC GGATGC                        36

( 2 ) INFORMATION FOR SEQ ID NO:33:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:33:

GTACTCCATA TCAGCTGGAT GAAG                                    24

( 2 ) INFORMATION FOR SEQ ID NO:34:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:34:

GGTCTATGAT AGTGTGACTA CTTTGACTAC TGGGGCCAAG GC                 42

( 2 ) INFORMATION FOR SEQ ID NO:35:

( i ) SEQUENCE CHARACTERISTICS:

(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

GCATCCTGGA AGGTTCAGAT GAATACCTTG TATGCAAAAT CC 42

(2) INFORMATION FOR SEQ ID NO:36:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

GGCTGATGCT GCACCAACTG TATCCATCTT CCCACCATCC AG 42

(2) INFORMATION FOR SEQ ID NO:37:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

CATTCTGGGT ATGAAGAGCC CACGTATCAA AGGTTACATT AG 42

(2) INFORMATION FOR SEQ ID NO:38:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

GATCGCGCGC TG 12

(2) INFORMATION FOR SEQ ID NO:39:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:39:

AATTGCGCGC TG 12

(2) INFORMATION FOR SEQ ID NO:40:

(i) SEQUENCE CHARACTERISTICS:
(A) LENGTH: 42 base pairs
(B) TYPE: nucleic acid
(C) STRANDEDNESS: single
(D) TOPOLOGY: linear 5,874,299

81

82

-continued ( i i ) MOLECULE TYPE: DNA (genomic)

( x i ) SEQUENCE DESCRIPTION: SEQ ID NO:40:

CTCACGTTCG GTGCTGGGAC CAAGCTGGAG CTGAAACGTA AG　　　　　　　　　42

( 2 ) INFORMATION FOR SEQ ID NO:41:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:41:

ACTATGCTAT GGACTACTGG GGTCAAGGAA CCTCAGTCAC CG　　　　　　　　　42

( 2 ) INFORMATION FOR SEQ ID NO:42:

( i ) SEQUENCE CHARACTERISTICS:
      ( A ) LENGTH: 59 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:42:

GGCCGCTCGA CGATAGCCTC GAGGCTATAA ATCTAGAAGA ATTCCAGCAA AGCTTTGGC　　59

( 2 ) INFORMATION FOR SEQ ID NO:43:

( i ) SEQUENCE CHARACTERISTICS:
      ( A ) LENGTH: 48 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:43:

CAAGAGCCCG CCTAATGAGC GGGCTTTTTT TTGCATACTG CGGCCGCT　　　　　　48

( 2 ) INFORMATION FOR SEQ ID NO:44:

( i ) SEQUENCE CHARACTERISTICS:
      ( A ) LENGTH: 48 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:44:

AATTAGCGGC CGCAGTATGC AAAAAAAGC CCGCTCATTA GGCGGGCT　　　　　　　48

( 2 ) INFORMATION FOR SEQ ID NO:45:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:45:

GGCCGCAAGC TTACTGCTGG ATCCTTAATT AATCGATAGT GATCTCGAGG C　　　　　51

( 2 ) INFORMATION FOR SEQ ID NO:46:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

```
GGCCGCCTCG AGATCACTAT CGATTAATTA AGGATCCAGC AGTAAGCTTG C                51
```

( 2 ) INFORMATION FOR SEQ ID NO:47:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

```
CTCCAGGATC CAGATATCAG TACCTGAAAC AGGGCTTGC                               39
```

( 2 ) INFORMATION FOR SEQ ID NO:48:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

```
CTCGAGCATG CACAGGACCT GGAGCACACA CAGCCTTCC                               39
```

( 2 ) INFORMATION FOR SEQ ID NO:49:

( i ) SEQUENCE CHARACTERISTICS:
        ( A ) LENGTH: 3698 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

```
AATTAGCGGC CGCCTCGAGA TCACTATCGA TTAATTAAGG ATCCAGATAT CACTACCTGA        60
AACAGGGCTT GCTCACAACA TCTCTCTCTC TGTCTCTCTG TCTCTGTGTC TGTGTCTCTC       120
TCTGTCTCTG TCTCTCTCTG TCTCTCTGTC TCTGTGTGTG TCTCTCTCTG TCTCTCTCTC       180
TGTCTCTCTG TCTCTCTGTC TGTCTCTGTC TCTGTCTCTG TCTCTCTCTC TCTCTCTCTC       240
TCTCTCTCTC TCTCTCTCAC ACACACACAC ACACACACAC ACACCTGC CGAGTGACTC         300
ACTCTGTGCA GGGTTGGCCC TCGGGGCACA TGCAAATGGA TGTTTGTTCC ATGCAGAAAA       360
ACATGTTTCT CATTCTCTGA GCCAAAAATA GCATCAATGA TTCCCCCACC CTGCAGCTGC       420
AGGTTCACCC CACCTGGCCA GGTTGACCAG CTTTGGGGAT GGGGCTGGGG GTTCCATGAC       480
CCCTAACGGT GACATTGAAT TCAGTGTTTT CCCATTTATC GACACTGCTG GAATCTGACC       540
CTAGGAGGGA ATGACAGGAG ATAGGCAAGG TCCAAACACC CCAGGGAAGT GGGAGAGACA       600
GGAAGGCTGT GTGTGCTCCA GGTCCTGTGC ATGCTGCAGA TCTGAATTCC CGGCTACCAA       660
```

```
GCTTGCGGCC  GCAGTATGCA  AAAAAAAGCC  CGCTCATTAG  GCGGGCTCTT  GGCAGAACAT    720
ATCCATCGCG  TCCGCCATCT  CCAGCAGCCG  CACGCGGCGC  ATCTCGGGCA  GCGTTGGGTC    780
CTGGCCACGG  GTGCGCATGA  TCGTGCTCCT  GTCGTTGAGG  ACCCGGCTAG  GCTGGCGGGG    840
TTGCCTTACT  GGTTAGCAGA  ATGAATCACC  GATACGCGAG  CGAACGTGAA  GCGACTGCTG    900
CTGCAAAACG  TCTGCGACCT  GAGCAACAAC  ATGAATGGTC  TTCGGTTTCC  GTGTTTCGTA    960
AAGTCTGGAA  ACGCGGAAGT  CAGCGCCCTG  CACCATTATG  TTCCGGATCT  GCATCGCAGG   1020
ATGCTGCTGG  CTACCCTGTG  GAACACCTAC  ATCTGTATTA  ACGAAGCGCT  GGCATTGACC   1080
CTGAGTGATT  TTTCTCTGGT  CCCGCCGCAT  CCATACCGCC  AGTTGTTTAC  CCTCACAACG   1140
TTCCAGTAAC  CGGGCATGTT  CATCATCAGT  AACCCGTATC  GTGAGCATCC  TCTCTCGTTT   1200
CATCGGTATC  ATTACCCCCA  TGAACAGAAA  TTCCCCCTTA  CACGGAGGCA  TCAAGTGACC   1260
AAACAGGAAA  AAACCGCCCT  TAACATGGCC  CGCTTTATCA  GAAGCCAGAC  ATTAACGCTT   1320
CTGGAGAAAC  TCAACGAGCT  GGACGCGGAT  GAACAGGCAG  ACATCTGTGA  ATCGCTTCAC   1380
GACCACGCTG  ATGAGCTTTA  CCGCAGCTGC  CTCGCGCGTT  TCGGTGATGA  CGGTGAAAAC   1440
CTCTGACACA  TGCAGCTCCC  GGAGACGGTC  ACAGCTTGTC  TGTAAGCGGA  TGCCGGGAGC   1500
AGACAAGCCC  GTCAGGGCGC  GTCAGCGGGT  GTTGGCGGGT  GTCGGGCGC  AGCCATGACC   1560
CAGTCACGTA  GCGATAGCGG  AGTGTATACT  GGCTTAACTA  TGCGGCATCA  GAGCAGATTG   1620
TACTGAGAGT  GCACCATATG  CGGTGTGAAA  TACCGCACAG  ATGCGTAAGG  AGAAAATACC   1680
GCATCAGGCG  CTCTTCCGCT  TCCTCGCTCA  CTGACTCGCT  GCGCTCGGTC  GTTCGGCTGC   1740
GGCGAGCGGT  ATCAGCTCAC  TCAAAGGCGG  TAATACGGTT  ATCCACAGAA  TCAGGGGATA   1800
ACGCAGGAAA  GAACATGTGA  GCAAAAGGCC  AGCAAAAGGC  CAGGAACCGT  AAAAAGGCCG   1860
CGTTGCTGGC  GTTTTTCCAT  AGGCTCCGCC  CCCCTGACGA  GCATCACAAA  AATCGACGCT   1920
CAAGTCAGAG  GTGGCGAAAC  CCGACAGGAC  TATAAAGATA  CCAGGCGTTT  CCCCCTGGAA   1980
GCTCCCTCGT  GCGCTCTCCT  GTTCCGACCC  TGCCGCTTAC  CGGATACCTG  TCCGCCTTTC   2040
TCCCTTCGGG  AAGCGTGGCG  CTTTCTCATA  GCTCACGCTG  TAGGTATCTC  AGTTCGGTGT   2100
AGGTCGTCGC  TCCAAGCTGG  GCTGTGTGCA  CGAACCCCCC  GTTCAGCCCG  ACCGCTGCGC   2160
CTTATCCGGT  AACTATCGTC  TTGAGTCCAA  CCCGGTAAGA  CACGACTTAT  CGCCACTGGC   2220
AGCAGCCACT  GGTAACAGGA  TTAGCAGAGC  GAGGTATGTA  GGCGGTGCTA  CAGAGTTCTT   2280
GAAGTGGTGG  CCTAACTACG  GCTACACTAG  AAGGACAGTA  TTTGGTATCT  GCGCTCTGCT   2340
GAAGCCAGTT  ACCTTCGGAA  AAAGAGTTGG  TAGCTCTTGA  TCCGGCAAAC  AAACCACCGC   2400
TGGTAGCGGT  GGTTTTTTTG  TTTGCAAGCA  GCAGATTACG  CGCAGAAAAA  AAGGATCTCA   2460
AGAAGATCCT  TTGATCTTTT  CTACGGGGTC  TGACGCTCAG  TGGAACGAAA  ACTCACGTTA   2520
AGGGATTTTG  GTCATGAGAT  TATCAAAAAG  GATCTTCACC  TAGATCCTTT  TAAATTAAAA   2580
ATGAAGTTTT  AAATCAATCT  AAAGTATATA  TGAGTAAACT  TGGTCTGACA  GTTACCAATG   2640
CTTAATCAGT  GAGGCACCTA  TCTCAGCGAT  CTGTCTATTT  CGTTCATCCA  TAGTTGCCTG   2700
ACTCCCCGTC  GTGTAGATAA  CTACGATACG  GGAGGGCTTA  CCATCTGGCC  CCAGTGCTGC   2760
AATGATACCG  CGAGACCCAC  GCTCACCGGC  TCCAGATTTA  TCAGCAATAA  ACCAGCCAGC   2820
CGGAAGGGCC  GAGCGCAGAA  GTGGTCCTGC  AACTTTATCC  GCCTCCATCC  AGTCTATTAA   2880
TTGTTGCCGG  GAAGCTAGAG  TAAGTAGTTC  GCCAGTTAAT  AGTTTGCGCA  ACGTTGTTGC   2940
CATTGCTGCA  GGCATCGTGG  TGTCACGCTC  GTCGTTTGGT  ATGGCTTCAT  TCAGCTCCGG   3000
TTCCCAACGA  TCAAGGCGAG  TTACATGATC  CCCCATGTTG  TGCAAAAAAG  CGGTTAGCTC   3060
```

| | | | | | | |
|---|---|---|---|---|---|---|
| CTTCGGTCCT | CCGATCGTTG | TCAGAAGTAA | GTTGGCCGCA | GTGTTATCAC | TCATGGTTAT | 3120 |
| GGCAGCACTG | CATAATTCTC | TTACTGTCAT | GCCATCCGTA | AGATGCTTTT | CTGTGACTGG | 3180 |
| TGAGTACTCA | ACCAAGTCAT | TCTGAGAATA | GTGTATGCGG | CGACCGAGTT | GCTCTTGCCC | 3240 |
| GGCGTCAACA | CGGGATAATA | CCGCGCCACA | TAGCAGAACT | TTAAAAGTGC | TCATCATTGG | 3300 |
| AAAACGTTCT | TCGGGGCGAA | AACTCTCAAG | GATCTTACCG | CTGTTGAGAT | CCAGTTCGAT | 3360 |
| GTAACCCACT | CGTGCACCCA | ACTGATCTTC | AGCATCTTTT | ACTTTCACCA | GCGTTTCTGG | 3420 |
| GTGAGCAAAA | ACAGGAAGGC | AAAATGCCGC | AAAAAAGGGA | ATAAGGGCGA | CACGGAAATG | 3480 |
| TTGAATACTC | ATACTCTTCC | TTTTTCAATA | TTATTGAAGC | ATTTATCAGG | GTTATTGTCT | 3540 |
| CATGAGCGGA | TACATATTTG | AATGTATTTA | GAAAAATAAA | CAAATAGGGG | TTCCGCGCAC | 3600 |
| ATTTCCCCGA | AAAGTGCCAC | CTGACGTCTA | AGAAACCATT | ATTATCATGA | CATTAACCTA | 3660 |
| TAAAAATAGG | CGTATCACGA | GGCCCTTTCG | TCTTCAAG | | | 3698 |

( 2 ) INFORMATION FOR SEQ ID NO:50:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

| | | | | |
|---|---|---|---|---|
| CAGCAGGTGC | ACACCCAATG | CCCATGAGCC | CAGACACTGG | AC | 42 |

( 2 ) INFORMATION FOR SEQ ID NO:51:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

TGAGCCCAGA CACTGGAC      18

( 2 ) INFORMATION FOR SEQ ID NO:52:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

GTTAAAGAGG ATTTTATTCA CCCCTGTGTC CTCTCCACAG GTGTC      45

( 2 ) INFORMATION FOR SEQ ID NO:53:

( i ) SEQUENCE CHARACTERISTICS:
        ( A ) LENGTH: 812 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:

( A ) NAME/KEY: Exon
( B ) LOCATION: 241..335
( D ) OTHER INFORMATION: Codes for peptide of SEQ ID NO 54

( i x ) FEATURE:
( A ) NAME/KEY: Exon
( B ) LOCATION: 372..677
( D ) OTHER INFORMATION: Codes for peptide of SEQ ID NO 55

( x i ) SEQUENCE DESCRIPTION: SEQ ID NO:53:

| | | | | | |
|---|---|---|---|---|---|
| TTCCTCAGGC | AGGATTTAGG | GCTTGGTCTC | TCAGCATCCC | ACACTTGTAC | AGCTGATGTG | 60
| GCATCTGTGT | TTTCTTTCTC | ATCCTAGATC | AAGCTTTGAG | CTGTGAAATA | CCCTGCCTCA | 120
| TGAATATGCA | AATAATCTGA | GGTCTTCTGA | GATAAATATA | GATATATTGG | TGCCCTGAGA | 180
| GCATCACATA | ACAACCAGAT | TCCTCCTCTA | AAGAAGCCCC | TGGGAGCACA | GCTCATCACC | 240
| ATGGACTGGA | CCTGGAGGTT | CCTCTTTGTG | GTGGCAGCAG | CTACAGGTAA | GGGGCTTCCT | 300
| AGTCCTAAGG | CTGAGGAAGG | GATCCTGGTT | TAGTTAAAGA | GGATTTTATT | CACCCCTGTG | 360
| TCCTCTCCAC | AGGTGTCCAG | TCCCAGGTCC | AGCTGGTGCA | GTCTGGGGCT | GAGGTGAAGA | 420
| AGCCTGGGTC | CTCGGTGAAG | GTCTCCTGCA | AGGCTTCTGG | AGGCACCTTC | AGCAGCTATG | 480
| CTATCAGCTG | GGTGCGACAG | GCCCCTGGAC | AAGGGCTTGA | GTGGATGGGA | AGGATCATCC | 540
| CTATCCTTGG | TATAGCAAAC | TACGCACAGA | AGTTCCAGGG | CAGAGTCACG | ATTACCGCGG | 600
| ACAAATCCAC | GAGCACAGCC | TACATGGAGC | TGAGCAGCCT | GAGATCTGAG | GACACGGCCG | 660
| TGTATTACTG | TGCGAGAGAC | ACAGTGTGAA | AACCCACATC | CTGAGAGTGT | CAGAAACCCT | 720
| GAGGGAGAAG | GCAGCTGTGC | CGGGCTGAGG | AGATGACAGG | GTTTATTAGG | TTTAAGGCTG | 780
| TTTACAAAAT | GGGTTATATA | TTTGAGAAAA | AA | | | 812

( 2 ) INFORMATION FOR SEQ ID NO:54:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:54:

Met Asp Trp Thr Trp Arg Phe Leu Phe Val Val Ala Ala Ala Thr
1               5                   10                  15

( 2 ) INFORMATION FOR SEQ ID NO:55:

( i ) SEQUENCE CHARACTERISTICS:
( A ) LENGTH: 102 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:55:

Gly Val Gln Ser Gln Val Gln Leu Val Gln Ser Gly Ala Glu Val Lys
1               5                   10                  15

Lys Pro Gly Ser Ser Val Lys Val Ser Cys Lys Ala Ser Gly Gly Thr
                20                  25                  30

Phe Ser Ser Tyr Ala Ile Ser Trp Val Arg Gln Ala Pro Gly Gln Gly
                35                  40                  45

Leu Glu Trp Met Gly Arg Ile Ile Pro Ile Leu Gly Ile Ala Asn Tyr
            50                  55                  60

| Ala | Gln | Lys | Phe | Gln | Gly | Arg | Val | Thr | Ile | Thr | Ala | Asp | Lys | Ser | Thr |
| 65 | | | | 70 | | | | | 75 | | | | | | 80 |

| Ser | Thr | Ala | Tyr | Met | Glu | Leu | Ser | Ser | Leu | Arg | Ser | Glu | Asp | Thr | Ala |
| | | | | 85 | | | | | 90 | | | | | 95 | |

| Val | Tyr | Tyr | Cys | Ala | Arg |
| | | | | 100 | |

( 2 ) INFORMATION FOR SEQ ID NO:56:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

CCGGTCGACC GG                          12

( 2 ) INFORMATION FOR SEQ ID NO:57:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

TCAGTGAAGG TTTCCTGCAA GGCATCTGGA TACACCTTCA CC        42

( 2 ) INFORMATION FOR SEQ ID NO:58:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

TCCCTGAGAC TCTCCTGTGC AGCCTCTGGA TTCACCTTCA GT        42

( 2 ) INFORMATION FOR SEQ ID NO:59:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

GGCCGCATCC CGGGTCTCGA GGTCGACAAG CTTTCGAGGA TCCGC        45

( 2 ) INFORMATION FOR SEQ ID NO:60:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

GGCCGCGGAT CCTCGAAAGC TTGTCGACCT CGAGACCCGG GATGC 45

( 2 ) INFORMATION FOR SEQ ID NO:61:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

GGCCGCTGTC GACAAGCTTA TCGATGGATC CTCGAGTGC 39

( 2 ) INFORMATION FOR SEQ ID NO:62:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

GGCCGCACTC GAGGATCCAT CGATAAGCTT GTCGACAGC 39

( 2 ) INFORMATION FOR SEQ ID NO:63:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

CACCTTCGGC CAAGGGACAC GACTGGAGAT TAAACGTAAG CA 42

( 2 ) INFORMATION FOR SEQ ID NO:64:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

AGGTTCAGTG GCAGTGGGTC TGGGACAGAC TTCACTCTCA CCATCAGC 48

( 2 ) INFORMATION FOR SEQ ID NO:65:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

GGCCGCATGC TACTCGAGTG CAAGCTTGGC CATCCA 36

( 2 ) INFORMATION FOR SEQ ID NO:66:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:66:

GGCCTGGATG GCCAAGCTTG CACTCGAGTA GCATGC     36

( 2 ) INFORMATION FOR SEQ ID NO:67:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:67:

CAGCTCGAGC TCGGCACAGG CGCCTGTGGG     30

( 2 ) INFORMATION FOR SEQ ID NO:68:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:68:

CTCTAGAGTC GACCTGCAGG C     21

( 2 ) INFORMATION FOR SEQ ID NO:69:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:69:

AGCCTCGAGC CCGTCTAAAA CCCTCCACAC     30

( 2 ) INFORMATION FOR SEQ ID NO:70:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:70:

GGTGACACTA TAGAATACTC AAGC     24

( 2 ) INFORMATION FOR SEQ ID NO:71:

( i ) SEQUENCE CHARACTERISTICS:
    ( A ) LENGTH: 21 base pairs
    ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:71:

GGAATTCTCA CAGGAGACGA G  21

( 2 ) INFORMATION FOR SEQ ID NO:72:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:72:

CTGACGACTC TGTATGGCGC CYASTSYSAG RTSCARCTKG TGSARTCKGG K  51

( 2 ) INFORMATION FOR SEQ ID NO:73:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:73:

GGGCTCGAGG CTGGTTTCTC TCACTGTGTG TBTNRYACAG TAATACAYRG Y  51

( 2 ) INFORMATION FOR SEQ ID NO:74:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:74:

CTGACGACTC TGTATGGCGC C  21

( 2 ) INFORMATION FOR SEQ ID NO:75:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:75:

GGGCTCGAGG CTGGTTTCTC T  21

( 2 ) INFORMATION FOR SEQ ID NO:76:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

-continued ( x i ) SEQUENCE DESCRIPTION: SEQ ID NO:76:

GGCCTAACTG AGCGTCCAT ATTGAGAACC TCC                33

( 2 ) INFORMATION FOR SEQ ID NO:77:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

GGTTCTCAAT ATGGGACGCT CAGTTA                26